(12) United States Patent
Li et al.

(10) Patent No.: US 9,795,694 B2
(45) Date of Patent: Oct. 24, 2017

(54) IMAGING BETA-AMYLOID PEPTIDES AGGREGATION

(71) Applicant: Hong Kong Baptist University, Hong Kong (HK)

(72) Inventors: Yinhui Li, Hong Kong (HK); Di Xu, Hong Kong (HK); See-Lok Ho, Hong Kong (HK); Chung-Yan Poon, Hong Kong (HK); Hei-Nga Chan, Hong Kong (HK); Hung Wing Li, Hong Kong (HK); Ricky M. S. Wong, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 70 days.

(21) Appl. No.: 15/049,126

(22) Filed: Feb. 21, 2016

(65) Prior Publication Data

US 2016/0243264 A1    Aug. 25, 2016

Related U.S. Application Data

(63) Continuation-in-part of application No. 14/231,724, filed on Mar. 31, 2014, now Pat. No. 9,403,794.

(51) Int. Cl.

| | |
|---|---|
| *A61K 49/00* | (2006.01) |
| *A61K 49/10* | (2006.01) |
| *A61M 5/00* | (2006.01) |
| *A61K 49/08* | (2006.01) |
| *C07D 401/06* | (2006.01) |
| *A61K 47/48* | (2006.01) |
| *G01R 33/56* | (2006.01) |

(52) U.S. Cl.
CPC ............ *A61K 49/106* (2013.01); *A61K 47/48* (2013.01); *A61K 49/0002* (2013.01); *A61K 49/0021* (2013.01); *A61K 49/0026* (2013.01); *A61K 49/0052* (2013.01); *A61K 49/085* (2013.01); *A61K 49/10* (2013.01); *A61M 5/007* (2013.01); *C07D 401/06* (2013.01); *G01R 33/5601* (2013.01)

(58) Field of Classification Search
CPC ............................ A61K 49/00; A61K 49/106
See application file for complete search history.

(56) References Cited

U.S. PATENT DOCUMENTS 7,700,616 B2 *    4/2010    Tamagnan ......... A61K 31/4184
                                                        514/299

* cited by examiner

*Primary Examiner* — Michael G Hartley
*Assistant Examiner* — Jagadishwar Samala
(74) *Attorney, Agent, or Firm* — Spruson & Ferguson (HK)

(57) ABSTRACT

The present invention is in the field of pharmaceuticals and chemical industries. In particular, one aspect of the present invention relates to methods for labeling, imaging and detecting the beta-amyloid (Aβ) peptides, oligomers, and fibrils in vitro and in vivo via magnetic resonance and florescence imaging by using modified carbazole-based fluorophores. A further aspect of the present invention relates to a method of reducing and preventing aggregation of beta-amyloid peptides for Alzheimer's disease (AD) as well as of treating and/or preventing Alzheimer's disease by using the modified carbazole-based fluorophore. The modified carbazole-based fluorophore according to an embodiment of the present invention is prepared by conjugating a carbazole-based fluorophore with magnetic nanoparticles to form a conjugate which is permeable to blood brain barrier of a subject being introduced therewith.

21 Claims, 56 Drawing Sheets

(17 of 56 Drawing Sheet(s) Filed in Color)

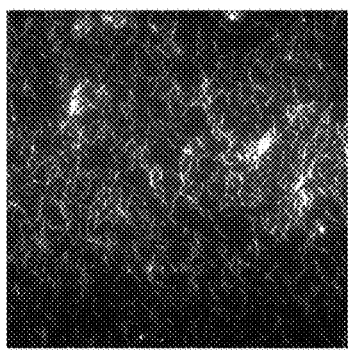 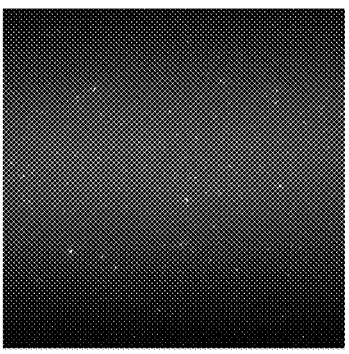 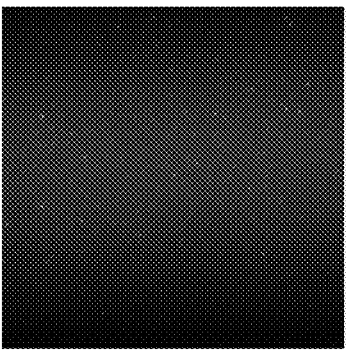
Figure 7A    Figure 7B    Figure 7C
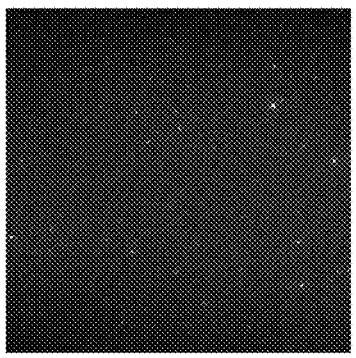 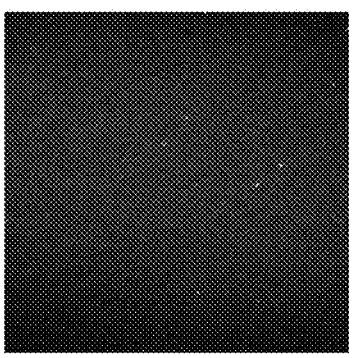 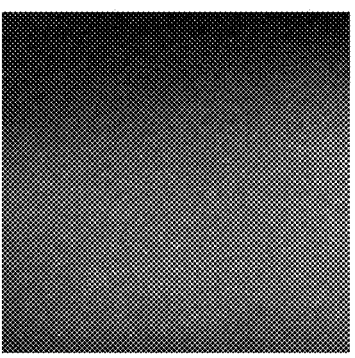
Figure 7D    Figure 7E    Figure 7F

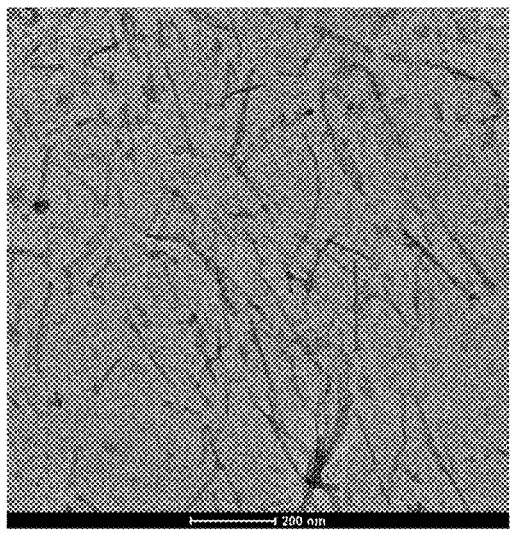 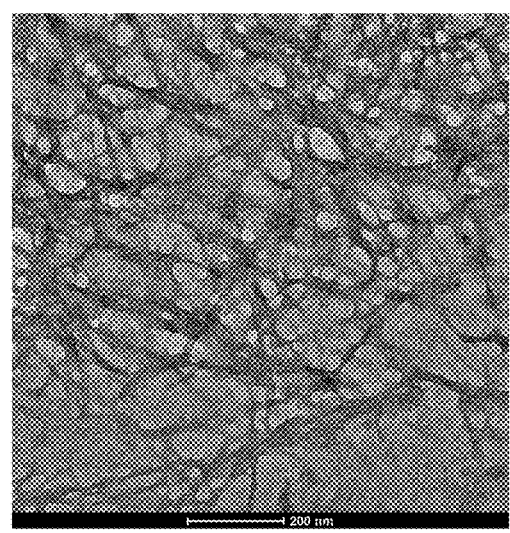
Figure 8A                    Figure 8B

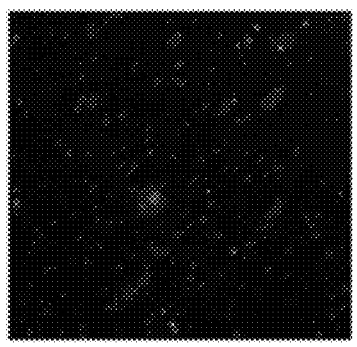
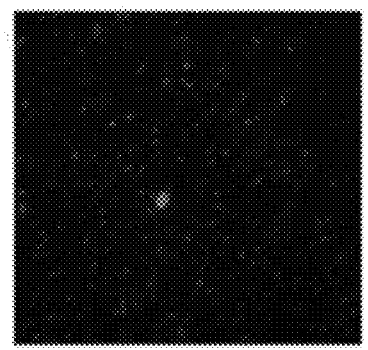
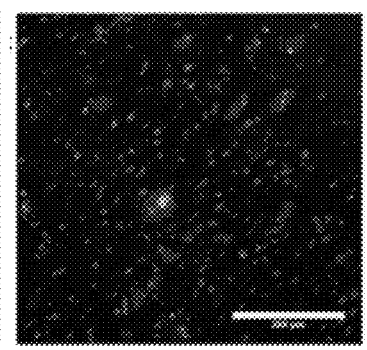
Figure 12A          Figure 12B          Figure 12C
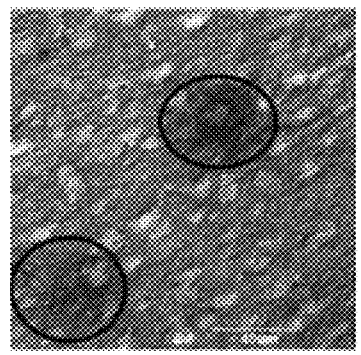
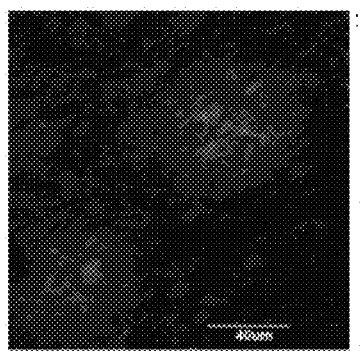
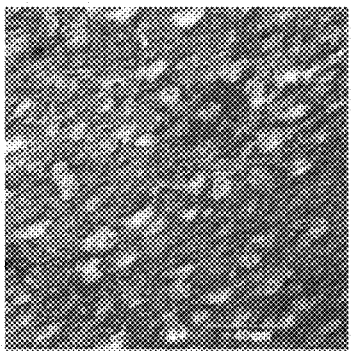
Figure 12D          Figure 12E          Figure 12F

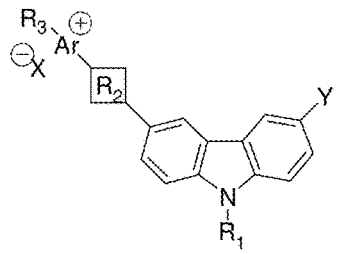

S series

Ar = heteroaromatic ring
such as

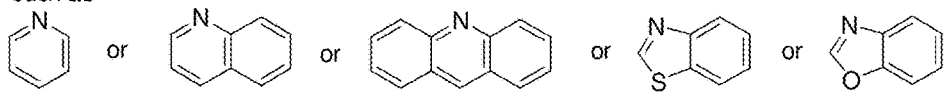

$R_1$ = polyethylene glycol chain
such as $(CH_2CH_2O)_2CH_3$ or
alkyl chain such as methyl, hexyl or
peptide chain or
glycosidic group or
$\underset{\underset{O}{\|}}{C}NHCH((CH_2CH_2O)_2CH_3)_2$ $\boxed{R_2}$ = HC=CH or
C≡C or
N=N or
HC=N X = anion such as
F⁻ or
Cl⁻ or
Br⁻ or
I⁻ or
$HSO_4^-$ or
$HPO_4^-$ or
$HCO_3^-$ or
OTs⁻ or
OMs⁻

$R_3$ = alkyl or
alkyl-OH or
alkyl-SH or
alkyl-NH$_2$ or
alkyl-NHalkyl or
alkyl-COOalkyl or
alkyl-CONHalkyl or
alkyl-CONH$_2$ or
alkyl-COOH or
alkyl-COO or
alkyl-N(alkyl)$_3^+$ or
alkyl-P(Ph)$_3^+$ or
polyethylene glycol chain Y = H or
F or
Cl or
OH or
OCH$_3$

Figure 14

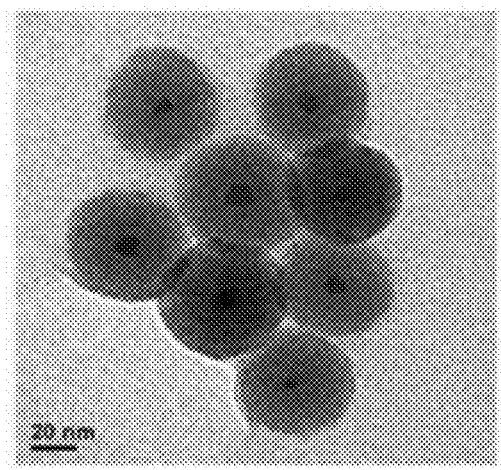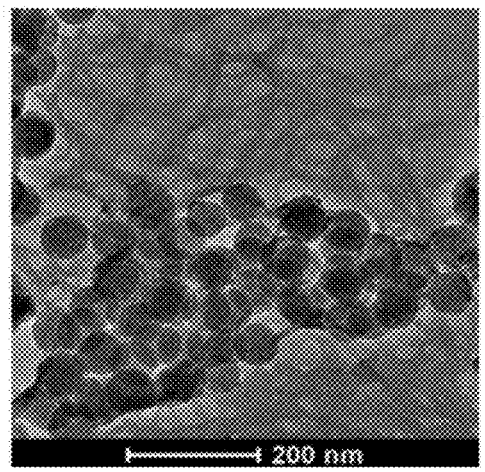
Figure 23A                    Figure 23B

IMAGING BETA-AMYLOID PEPTIDES AGGREGATION

CROSS-REFERENCE TO RELATED APPLICATIONS

The present application is a continuation-in-part application of the U.S. non-provisional patent application Ser. No. 14/231,724 filed Mar. 31, 2014, which claims priority of U.S. non-provisional patent application Ser. No. 13/447,127 filed Apr. 13, 2012, which further claims priority of U.S. provisional application No. 61/477,614 filed Apr. 21, 2011, and which the disclosures are hereby incorporated by reference in their entirety.

FIELD OF INVENTION

The present invention relates to methods of detecting and monitoring aggregation of beta-amyloid peptides which are associated with neurodegenerative diseases as well as treating and/or preventing the neurodegenerative diseases by using modified carbazole-based fluorophores. In particular, the present invention provides methods for labeling and imaging the beta-amyloid (Aβ) peptides, oligomers, and fibrils in vitro and/or in vivo via magnetic resonance and florescence imaging, as well as treating and/or preventing Alzheimer's disease by using the modified carbazole-based fluorophores of the present invention.

BACKGROUND OF INVENTION

Loss of memory and cognitive functions are often associated with aging. This is the result of neurodegeneration. However, in some cases, this process of neurodegeneration becomes accelerated due to premature cell death in the brain, leading to a variety of cognitive impairments or dementia. Among these neurodegenerative disorders, Alzheimer's disease (AD) is most prevalent in recent years. It has also attracted considerable attention locally because Prof. Charles K. Kao, former president of the Chinese University of Hong Kong and Nobel Laureate in Physics, 2009, was stricken with this devastating disease.

More than 36 million people worldwide were estimated to suffer from Alzheimer's disease (AD) in 2009 and the patient number was expected to increase to 115 million in 2050. The incidence rate of AD is known to increase with age. At age over 65, the incidence rate is about 5% in the general population. At age over 80, the incidence rate increases to about 20%, i.e., one in five. Current drug treatments can only improve symptoms and produce no profound cure. In recent years, several approaches aimed at inhibiting disease progression have advanced to clinical trials. Among them, strategies targeting the production and clearance of the Aβ peptide, which is thought to be a critical protein involved in the pathogenesis of the disease, are the most advanced.

Aβ peptide is the principal protein component of the Aβ plaques, which are found in the brains of AD patients during autopsy. The occurrence of the Aβ plaques, considered a cardinal feature of AD, provides the only confirmed diagnosis of the disease. Extensive researches in past decades have indicated a central role for the Aβ peptide in the disease process where the Aβ peptides assemble (aggregate) into Aβ fibrils which exert a cytotoxic effect towards the neurons and initiate the pathogenic cascade. Recent studies showed that oligomeric, prefibrillar and diffusible assemblies of Aβ peptides are also deleterious. The ability of this peptide to form Aβ fibrils seems to be largely sequence-independent, and many proteins can form structures with the characteristic cross-β stacking perpendicular to the long axis of the fiber. Although a consensus mechanism for the pathogenic oligomeric assembly has yet to emerge, the idea of finding some brain-penetrating small molecules that can interfere with the interactions among the Aβ peptide monomers and thus inhibit the formation of the neurotoxic oligomers and the resulting Aβ plaques is an attractive approach to treating/preventing the disease. The use of agents that stabilize the monomer, interfere with the aggregation process (amyloidogenesis) and allow for the isolation of the intermediate species will help to elucidate the molecular mechanism of Aβ fibril formation. In addition, imaging agents that can specifically bind Aβ fibrils and plaques in vitro and in vivo are of paramount importance for studying the pathological events of the disease, disease diagnosis and monitoring of therapeutic treatment.

The present inventors have previously shown that carbazole-based fluorophores are highly sensitive fluorescent light-up probe for double strand DNA and strongly active two-photon absorption dyes for two-photon excited bioimaging, the disclosure of which is incorporated by reference herein. Recently, the mono-cyanine fluorophore has also been found to exhibit binding affinity towards beta amyloid (Aβ) peptide concomitant with strong fluorescent enhancement. These findings provide us with the lead molecular structure to design and synthesize novel functional carbazole-based fluorophores for imaging and inhibition the aggregation of Aβ peptides.

Citation or identification of any reference in this section or any other section of this application shall not be construed as an admission that such reference is available as prior art for the present application.

SUMMARY OF INVENTION

Accordingly, the first objective of the presently claimed invention relates to a method of reducing and preventing aggregation of beta-amyloid peptides for Alzheimer's disease (AD) as well as of treating and/or preventing Alzheimer's disease by using carbazole-based fluorophores.

In the first aspect of the present invention there is provided a method for treatment and/or prevention of beta-amyloid (Aβ) peptides aggregation-associated diseases by using carbazole-based fluorophores comprising a formula S series:

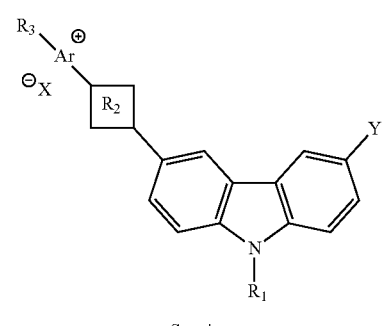

S series wherein said method comprising:
binding said carbazole-based fluorophores to Aβ peptides, oligomers and/or fibrils thereof;

inhibiting the growth and/or aggregation of said Aβ peptides, oligomers and/or fibrils upon said binding; and protecting neuronal cells against the neurotoxic activities of the Aβ oligomers and/or fibrils;

wherein Ar is a heteraromatic ring selected from the group consisting of pyridinyl, substituted pyridinyl, quinolinyl, substituted quinolinyl, acridinyl, substituted acridinyl, benzothiazolyl, substituted benzothiazolyl, benzoxazolyl, and substituted benzoxazolyl;

$R_1$ is a radical selected from the group consisting of polyethylene glycol chain, alkyl, substituted alkyl, peptide chain, glycosidyl, and $C(O)NHCH((CH_2CH_2O)_2CH_3)_2$;

$R_2$ is selected from the group consisting of ethenyl, ethynyl, azo and azomethinyl.

$R_3$ is a radical selected from the group consisting of alkyl, HO-alkyl, HS-alkyl, $H_2N$-alkyl, HNalkyl-alkyl, alkyl-COOalkyl, alkyl-$CONH_2$, alkyl-CONHalkyl, alkyl-COOH, alkyl-$COO^-$, $(alkyl)_3N^+$-alkyl, and $(Ph)_3P^+$-alkyl, and polyethylene glycol chain;

X is an anion selected from the group consisting of F, Cl, Br, I, $HSO_4$, $H_2PO_4$, $HCO_3$, tosylate, and mesylate;

Y is selected from the group consisting of H, F, Cl, OH, $OCH_3$ and $R_2$—Ar—$R_3$, wherein Ar is a heteraromatic ring selected from the group consisting of pyridinyl, substituted pyridinyl, quinolinyl, substituted quinolinyl, acridinyl, substituted acridinyl, benzothiazolyl, substituted benzothiazolyl, benzoxazolyl, and substituted benzoxazolyl; $R_2$ is selected from the group consisting of ethenyl, ethynyl, azo and azomethinyl; $R_3$ is a radical selected from the group consisting of alkyl, HO-alkyl, HS-alkyl, $H_2N$-alkyl, HNalkyl-alkyl, alkyl-COOalkyl, alkyl-$CONH_2$, alkyl-CONHalkyl, alkyl-COOH, alkyl-$COO^-$, $(alkyl)_3N^+$-alkyl, and $(Ph)_3P^+$-alkyl, and polyethylene glycol chain.

In a first embodiment of the first aspect of the present invention there is provided a method wherein Ar is selected from a quinolinyl or substituted quinolinyl; said $R_1$ is a 2-(2-methoxyethoxy)ethoxy; said $R_2$ is an ethenyl; $R_3$ is a 2-hydroxyethyl or acetamide or acetate or 2-(2-methoxyethoxy)ethoxy; said X is a chloride or bromide or iodide and said Y is a H or F which is represented by the formula F-SLOH, SLAD, SLAce, and SLG:

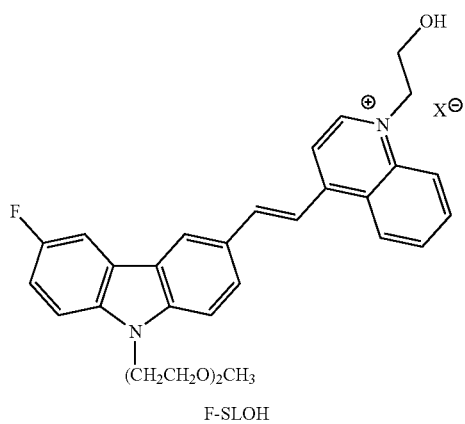

F-SLOH

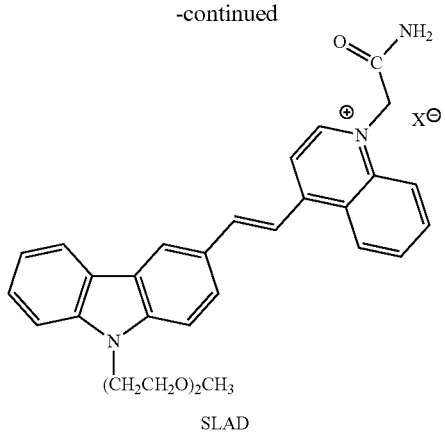

SLAD

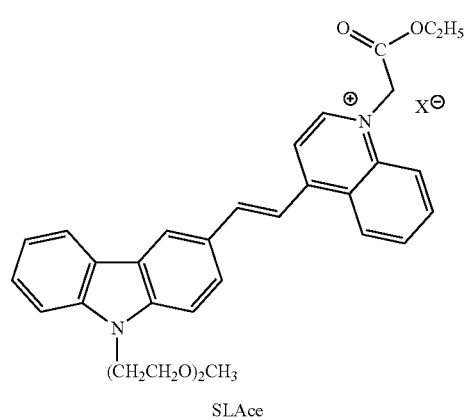

SLAce

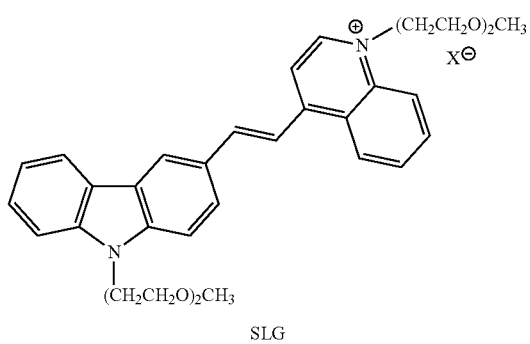

SLG

In a second embodiment of the first aspect of the present invention there is provided a method wherein the carbazole-based fluorophores are non-toxic and/or are able to pass through the blood-brain barrier.

In a third embodiment of the first aspect of the present invention there is provided a method wherein the carbazole-based fluorophores are administered in vitro and/or in vivo.

In a second aspect of the present invention there is provided a method for imaging and detection of beta-amyloid (Aβ) peptides aggregation via magnetic resonance imaging (MRI) and/or fluorescence imaging by using carbazole-based fluorophores comprising a formula S series or a formula V series:

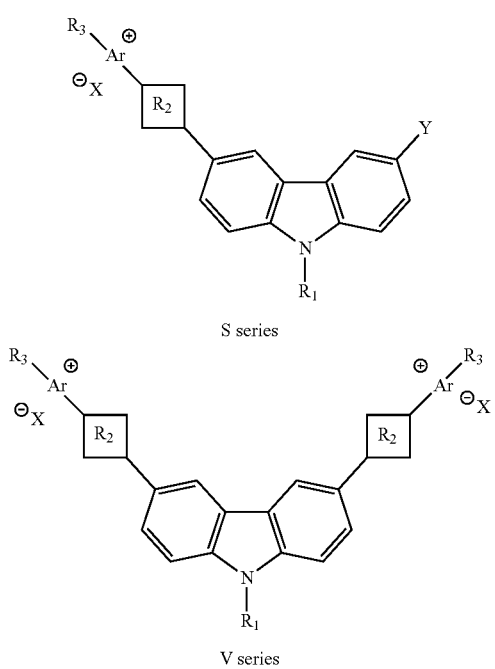

S series

V series said method comprising:
conjugating said carbazole-based fluorophores to magnetic nanoparticles to form a carbazole-based flurophores magnetic nanoparticles conjugate;
introducing the carbazole-based fluorophores magnetic nanoparticles conjugate to a subject with beta-amyloid (Aβ) peptides aggregation; and
applying MRI and/or fluorescence imaging to image and detect the conjugate of the carbazole-based fluorophores and magnetic nanoparticles bound to the beta-amyloid (Aβ) peptides aggregation in said subject;
wherein Ar is a heteroaromatic ring selected from the group consisting of pyridinyl, substituted pyridinyl, quinolinyl, substituted quinolinyl, acridinyl, substituted acridinyl, benzothiazolyl, substituted benzothiazolyl, benzoxazolyl, and substituted benzoxazolyl;
$R_1$ is a radical selected from the group consisting of polyethylene glycol chain, alkyl, substituted alkyl, peptide chain, glycosidyl, and $C(O)NHCH((CH_2CH_2O)_2CH_3)_2$;
$R_2$ is selected from the group consisting of ethenyl, ethynyl, azo and azomethinyl.
$R_3$ is a radical selected from the group consisting of alkyl, HO-alkyl, HS-alkyl, $H_2N$-alkyl, HNalkyl-alkyl, alkyl-COOalkyl, alkyl-$CONH_2$, alkyl-CONHalkyl, alkyl-COOH, alkyl-$COO^-$, $(alkyl)_3N^+$-alkyl, and $(Ph)_3P^+$-alkyl, and polyethylene glycol chain;
X is an anion selected from the group consisting of F, Cl, Br, I, $HSO_4$, $H_2PO_4$, $HCO_3$, tosylate, and mesylate;
Y is selected from the group consisting of H, F, Cl, OH, $OCH_3$, and $R_2$—Ar—$R_3$,
wherein Ar is a heteroaromatic ring selected from the group consisting of pyridinyl, substituted pyridinyl, quinolinyl, substituted quinolinyl, acridinyl, substituted acridinyl, benzothiazolyl, substituted benzothiazolyl, benzoxazolyl, and substituted benzoxazolyl; $R_2$ is selected from the group consisting of ethenyl, ethynyl, azo and azomethinyl; $R_3$ is a radical selected from the group consisting of alkyl, HO-alkyl, HS-alkyl, $H_2N$-alkyl, HNalkyl-alkyl, alkyl-COOalkyl, alkyl-$CONH_2$, alkyl-CONHalkyl, alkyl-COOH, alkyl-$COO^-$, $(alkyl)_3N^+$-alkyl, and $(Ph)_3P^+$-alkyl, and polyethylene glycol chain.

In a first embodiment of the second aspect of the present invention there is provided a method, wherein said carbazole-based fluorophores is represented by the formula SLCOOH and its derivatives by the formula SLCOOH-n, wherein n=2 to 20:

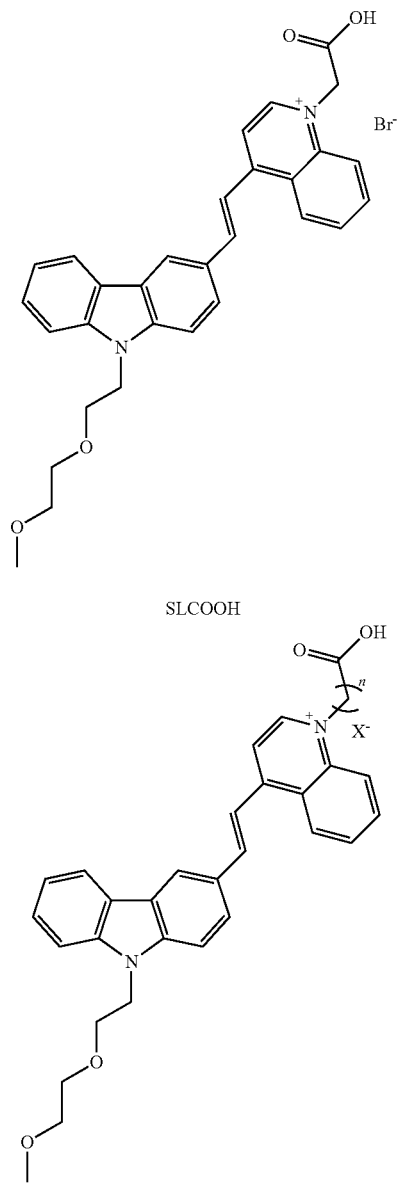

SLCOOH

SLCOOH-n

X = Cl, Br or I n = 2-20

In the formula S series, when Ar=quinolinyl, $R_1$=polyethylene glycol chain, $R_2$=ethenyl, $R_3$=alkyl-COOH, X=Br, Cl, or I, and Y=H, said carbazole-based fluorophores is represented by the formula SLCOOH and its derivatives SLCOOH-n, wherein n=2 to 20. In addition, when Y is substituted by $R_2$—Ar—$R_3$ which becomes the formula V series, wherein Ar=quinolinyl, $R_2$=ethenyl, $R_3$=alkyl-COOH, the resulting derivative has a replicate side chain as in SLCOOH or SLCOOH-n which possesses similar or even better effect on imaging and detection of the aggregation of Aβ peptides or the like.

In a second embodiment of the second aspect of the present invention there is provided a method, wherein the carbazole-based fluorophores magnetic nanoparticles conjugate is non-toxic.

In a third embodiment of the second aspect of the present invention there is provided a method, wherein the carbazole-based fluorophores magnetic nanoparticles conjugate is able to pass through the blood-brain barrier.

In a fourth embodiment of the second aspect of the present invention there is provided a method, wherein the magnetic nanoparticles are superparamagnetic and anti-ferromagnetic.

In a fifth embodiment of the second aspect of the present invention there is provided a method, wherein the magnetic nanoparticles comprising $SiO_2@Fe_3O_4$. In addition, the magnetic nanoparticles can be gold-coated or silver-coated iron-oxide nanoparticles. In this embodiment, when the magnetic nanoparticles are $SiO_2@Fe_3O_4$ which are conjugated with the carbazole-based fluorophores having the formula of SLCOOH or SLCOOH-n according to the first embodiment of the second aspect of the present invention, said conjugate is represented by one of the following formulae:

In a sixth embodiment of the second aspect of the present invention there is provided a method, said method further comprising introducing the carbazole-based fluorophores magnetic nanoparticles conjugate to Aβ peptides, oligomers and/or fibrils thereof in vitro.

In a seventh embodiment of the second aspect of the present invention there is provided a method, said method further comprising administering said conjugate of the carbazole-based fluorophores and the magnetic nanoparticles in vivo.

In an eighth embodiment of the second aspect of the present invention there is provided a method, wherein said beta-amyloid (Aβ) peptides aggregation is associated with Alzheimer's disease.

In a ninth embodiment of the second aspect of the present invention there is provided a method, wherein the carbazole-based fluorophores magnetic nanoparticles conjugate is introduced to a subject with beta-amyloid (Aβ) peptides aggregation via intravenous injection.

In a tenth embodiment of the second aspect of the present invention there is provided a method, wherein the carbazole-based fluorophores magnetic nanoparticles conjugate is introduced in vivo at about 10 mg/kg to body weight of said subject and said subject can be human.

Throughout this specification, unless the context requires otherwise, the word "include" or "comprise" or variations such as "includes" or "comprises" or "comprising", will be understood to imply the inclusion of a stated integer or group of integers but not the exclusion of any other integer or group of integers. It is also noted that in this disclosure and particularly in the claims and/or paragraphs, terms such as "included", "comprises", "comprised", "comprising" and the like can have the meaning attributed to it in U.S. Patent law; e.g., they can mean "includes", "included", "includ-

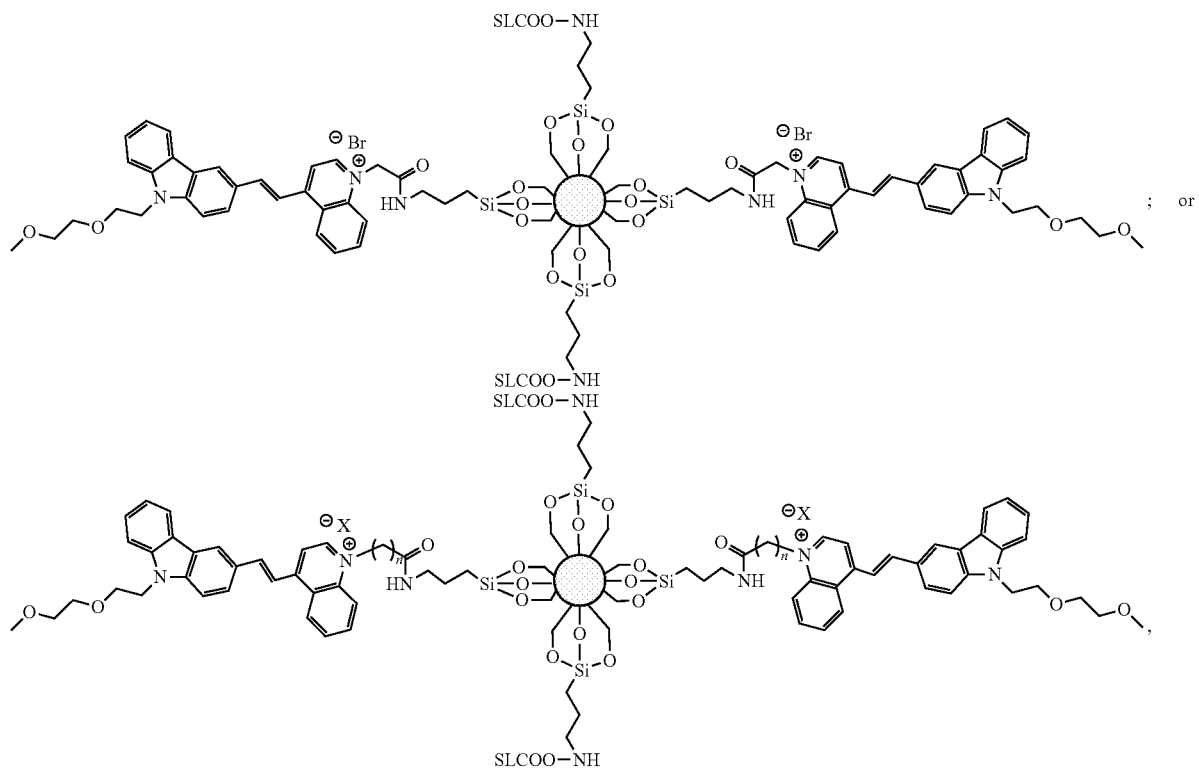

wherein

represents said $SiO_2@Fe_3O_4$; X represents Br, I, or Cl.

ing", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the present invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the present invention and apply throughout. Unless otherwise defined, all other technical terms used herein have the same meaning as commonly understood to one of ordinary skill in the art to which the present invention belongs.

Other aspects and advantages of the present invention will be apparent to those skilled in the art from a review of the ensuing description.

BRIEF DESCRIPTION OF DRAWINGS

The patent or application file contains at least one drawing executed in color. Copies of this patent or patent application publication with color drawing(s) will be provided by the Office upon request and payment of the necessary fee. The above and other objects and features of the present invention will become apparent from the following description of the present invention, when taken in conjunction with the accompanying drawings, in which:

The following figures show the fluorescence spectra of SPM, SPOH, SLM, SLOH, SLE, SLOH-Pr, Me-SLM, SAM, and SAOH (1 µM) in phosphate buffer upon addition of various concentrations of Aβ(1-40) fibrils prepared from $A\beta_{40}$ with seed incubated at 37° C. for an hour in buffer (left column)

The following figures shows the fluorescence spectra of SPM, SPOH, SLM and SLOH in phosphate buffer (1 µM) upon addition of various concentrations of Aβ(1-40) and Aβ(1-42), respectively.

FIG. 7A shows TIRFM images of Aβ fibrils; FIG. 7B shows TIRFM images of Aβ peptide after incubation with the carbazole-based fluorophore, SLOH; FIG. 7C shows TIRFM images of Aβ peptide after incubation with the carbazole-based fluorophore, SAOH; FIG. 7D shows TIRFM images of Aβ peptide after incubation with the carbazole-based fluorophore, SLE; FIG. 7E shows TIRFM images of Aβ peptide after incubation with the carbazole-based fluorophore, SLOH-Pr; and FIG. 7F shows TIRFM images of Aβ peptide after incubation with the carbazole-based fluorophore, Me-SLM. FIGS. 7B, 7C, 7E and 7F show an inhibition of Aβ fibril formation from the Aβ monomer by SLOH and SAOH. These images were obtained by an addition of ThT dye excited at 445 nm.

FIG. 8A shows TEM images of Aβ fibril growth from Aβ peptide (50 µM) seeded for 1 hr at 37° C. in the absence of SLOH; and FIG. 8B shows TEM images Aβ fibril growth from Aβ peptide (50 µM) seeded for 1 hr at 37° C. of the presence of SLOH.

Figure 10A:
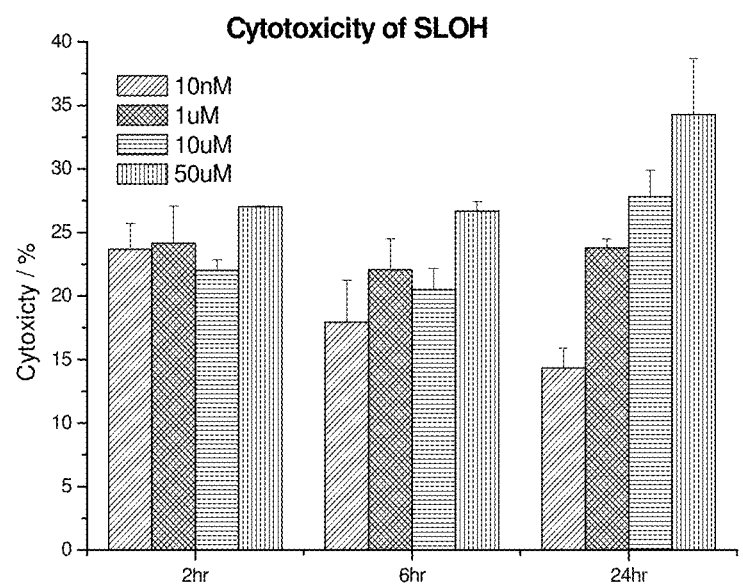
Figure 10B:
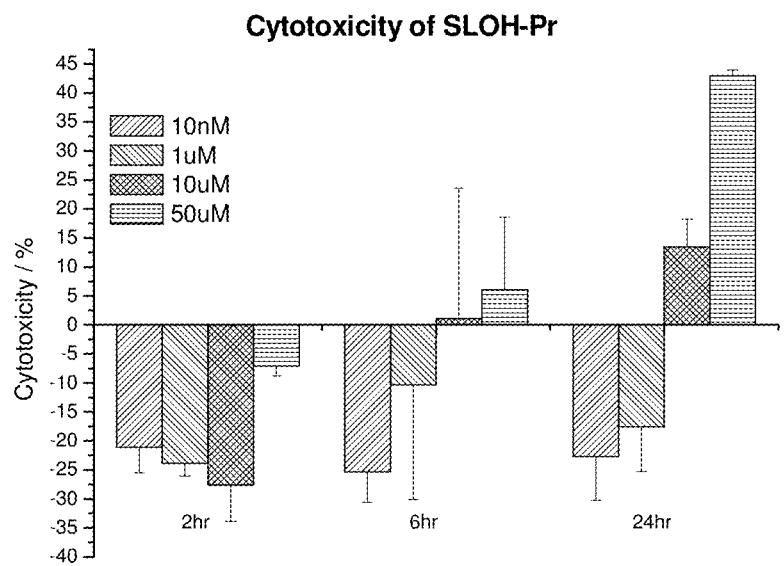
Figure 10C:
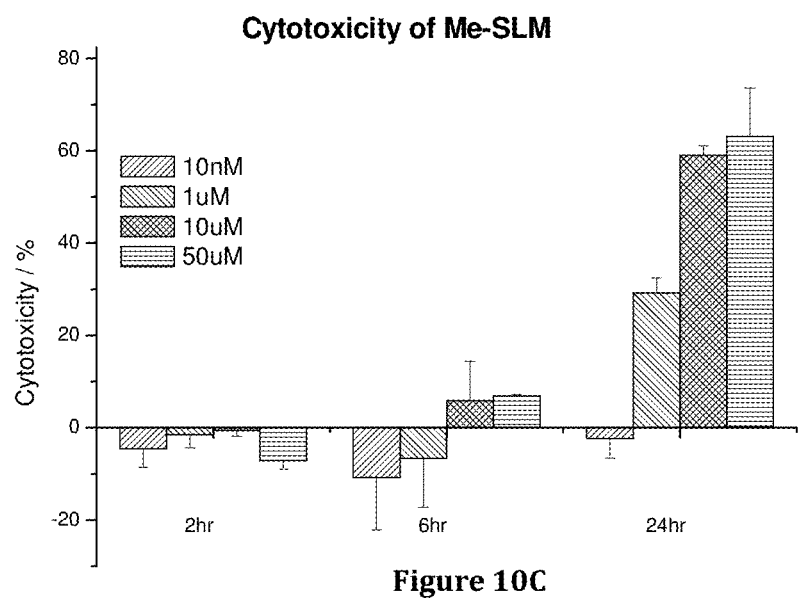
Figure 10D:
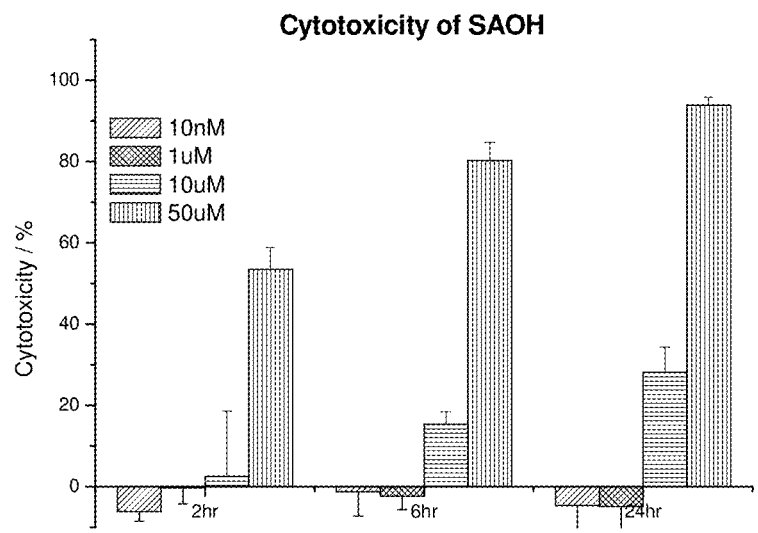

FIG. 10A shows cytotoxicities of the carbazole-based SLOH towards the SH-SY5Y neuronal cell with MTT assays; FIG. 10B shows cytotoxicities of the carbazole-based SLOH-Pr towards the SH-SY5Y neuronal cell with MTT assays; FIG. 10C shows cytotoxicities of the carbazole-based Me-SLM towards the SH-SY5Y neuronal cell with MTT assays; FIG. 10D shows cytotoxicities of the carbazole-based and SAOH towards the SH-SY5Y neuronal cell with MTT assays.

Figure 11A:
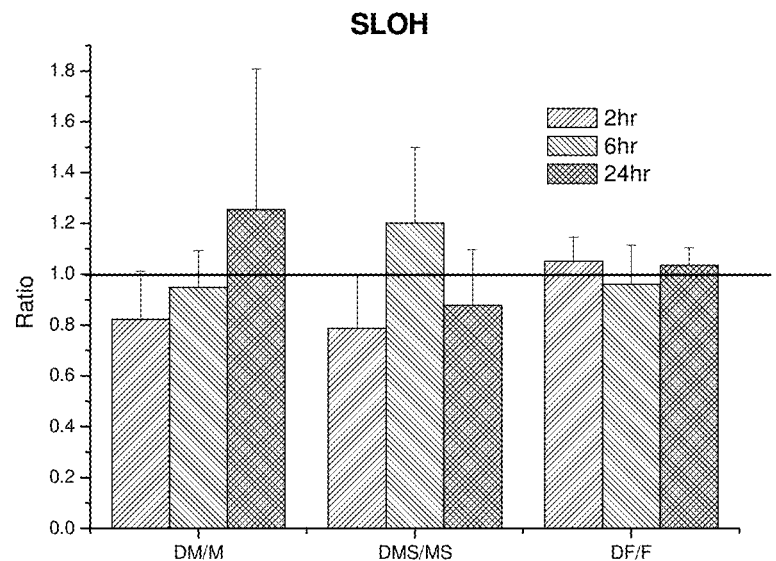
Figure 11B:
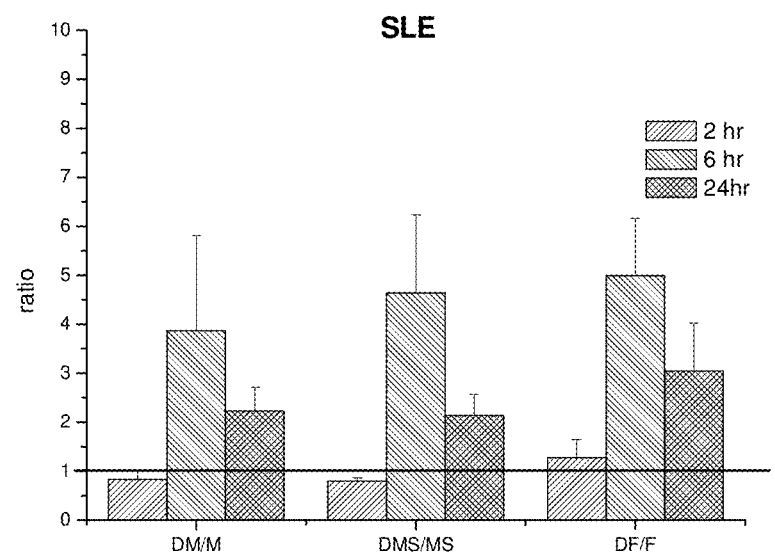
Figure 11C:
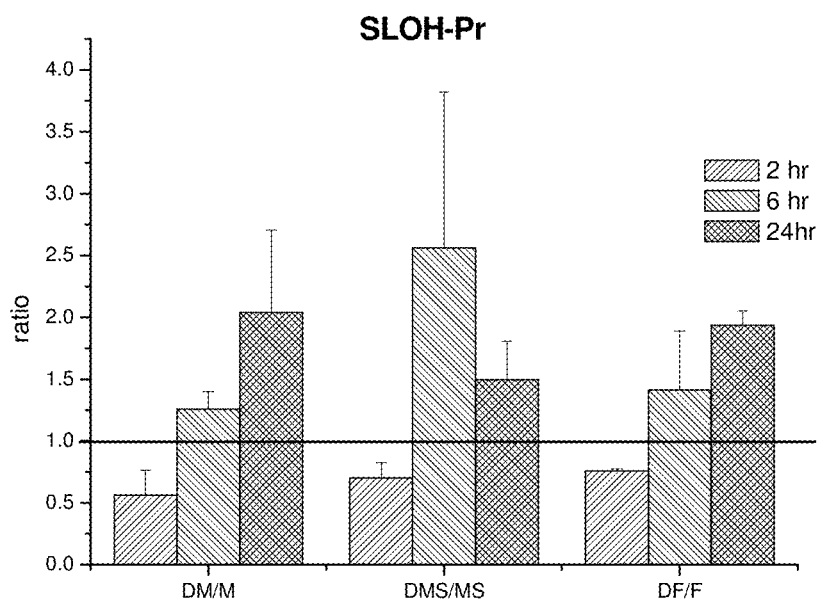
Figure 11D:
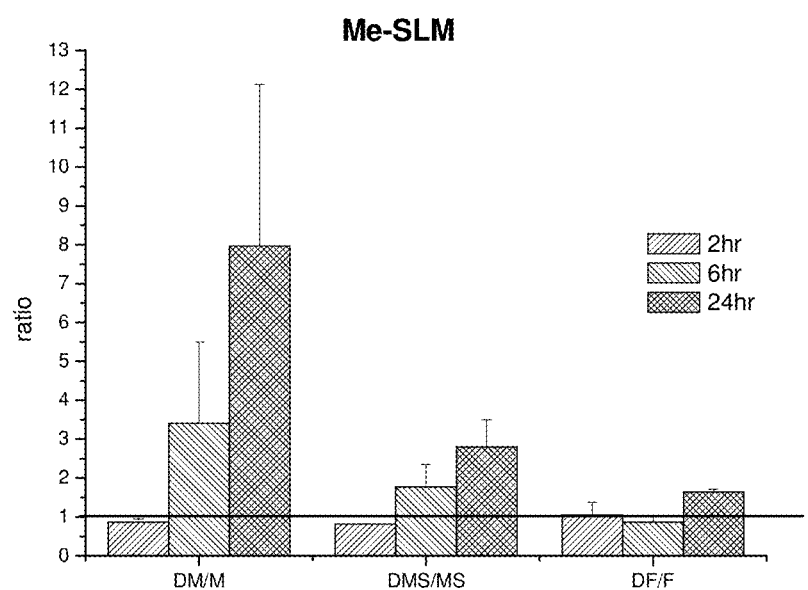

FIG. 11A shows cytotoxicities of Aβ peptide monomer (DM/M), oligomers (DM S/MS) and fibrils (DF/F) towards the SH-SY5Y neuronal cell in the absence and the presence of SLOH (50 μM) after 2 hr, 6 hr, and 24 hr incubations; FIG. 11B shows cytotoxicities of Aβ peptide monomer (DM/M), oligomers (DM S/MS) and fibrils (DF/F) towards the SH-SY5Y neuronal cell in the absence and the presence of SLE after 2 hr, 6 hr, and 24 hr incubations; FIG. 11C shows cytotoxicities of Aβ peptide monomer (DM/M), oligomers (DM S/MS) and fibrils (DF/F) towards the SH-SY5Y neuronal cell in the absence and the presence of SLOH-Pr after 2 hr, 6 hr, and 24 hr incubations; FIG. 11D shows cytotoxicities of Aβ peptide monomer (DM/M), oligomers (DM S/MS) and fibrils (DF/F) towards the SH-SY5Y neuronal cell in the absence and the presence of Me-SLM after 2 hr, 6 hr, and 24 hr incubations.

The following figures shows fluorescence images of transgenic mice brain with tail vein injection of SLOH and co-stained with the Aβ labeling dye, ThT or Aβ antibody with DAB stain: FIG. 12A shows fluorescence image corresponding to SLOH fluorescence captured at 550-630 nm under excitation at 488 nm; FIG. 12B shows ThT fluorescence captured at 470-550 nm under excitation at 458 nm; and FIG. 12C shows overlapped images of previous two images. The overlapped image revealed the colocalization of fluorescence signals of SLOH and ThT in cellular components. FIG. 12D shows Differential Interference Contrast (DIC) image of DAB stained brain slide of transgenic mice. FIG. 12E shows fluorescence image of same slide corresponding to SLOH fluorescence captured at 550-630 nm under excitation at 488 nm; and FIG. 12F shows overlapped images of previous two images. The overlapped image revealed the colocalization of fluorescence signals of SLOH and Aβ antibody in components.

Figure 13A:
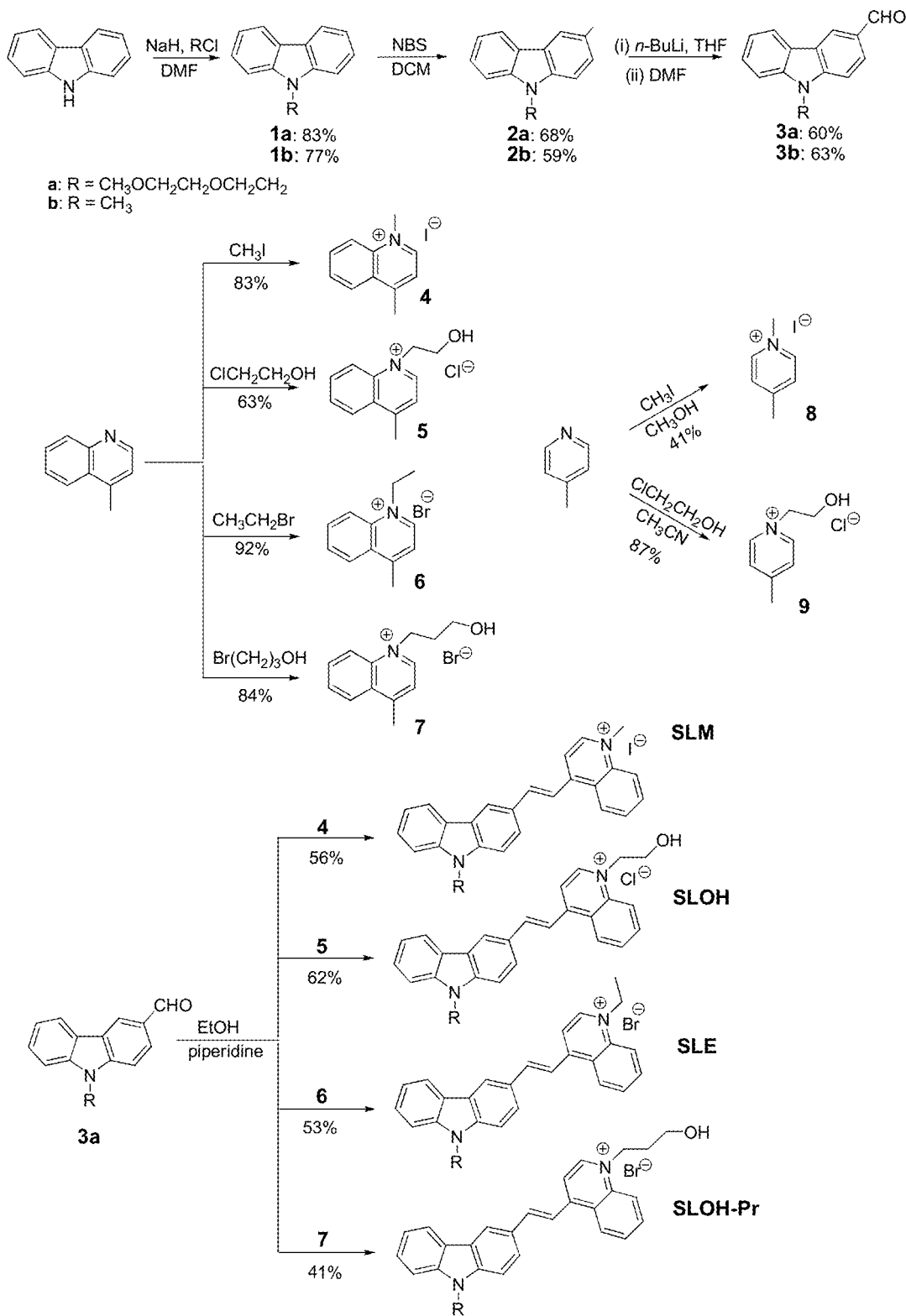
Figure 13B:
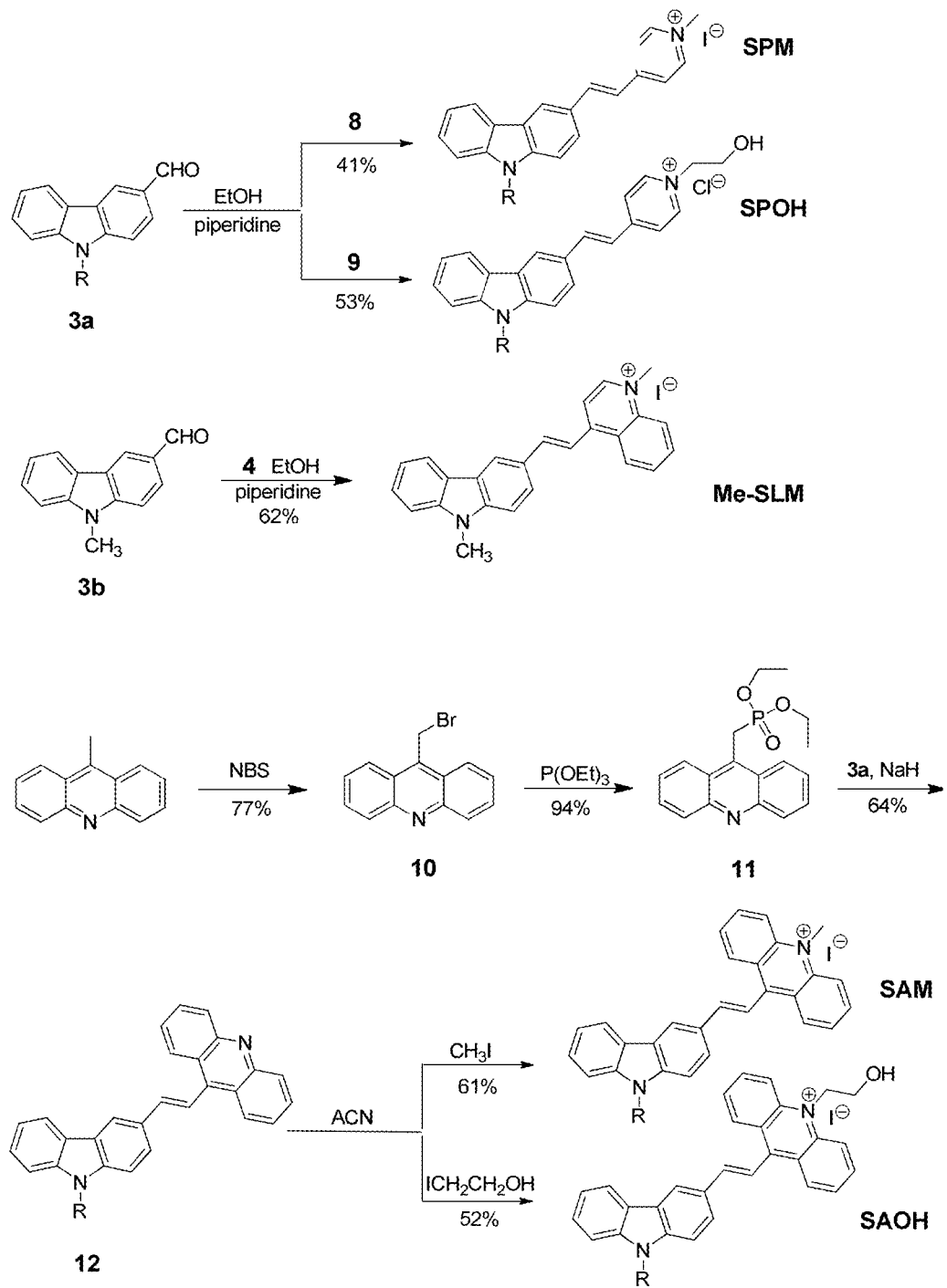

FIG. 13 shows synthesis of carbazole-based fluorophores, SLM, SLOH, SLE, SLOH-Pr (FIG. 13A) and SPM, SPOH, Me-SLM, SAM and SAOH (FIG. 13B).

FIG. 14 shows the general chemical structures of carbazole-based fluorophores, including S series.

Figure 15:
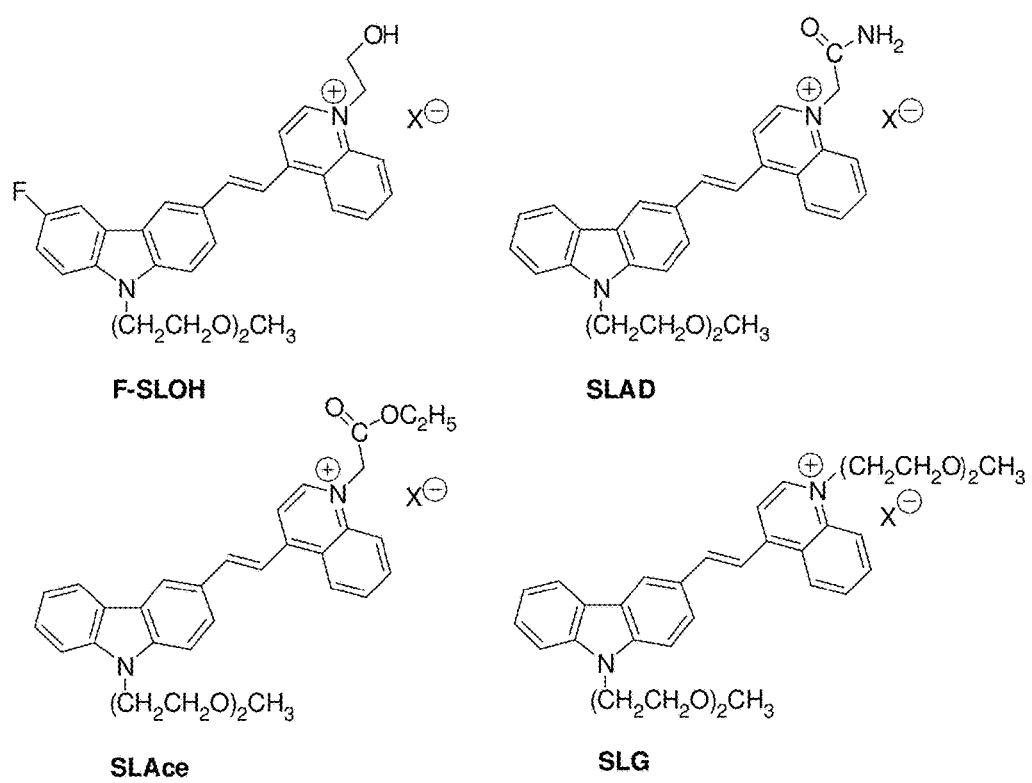
Figure 16A:
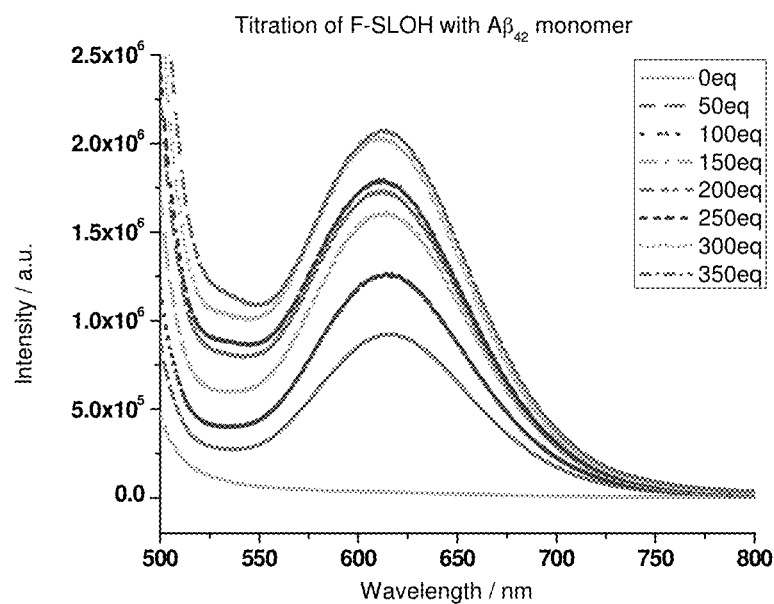
Figure 16B:
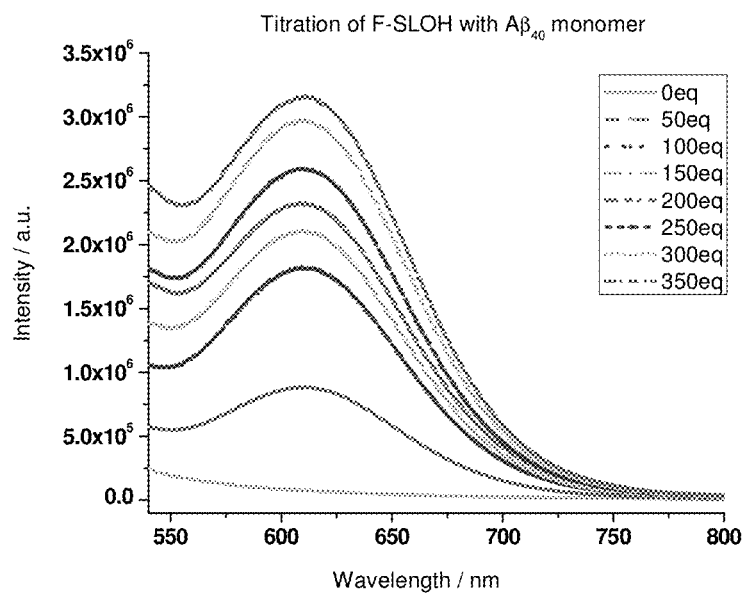
Figure 16C:
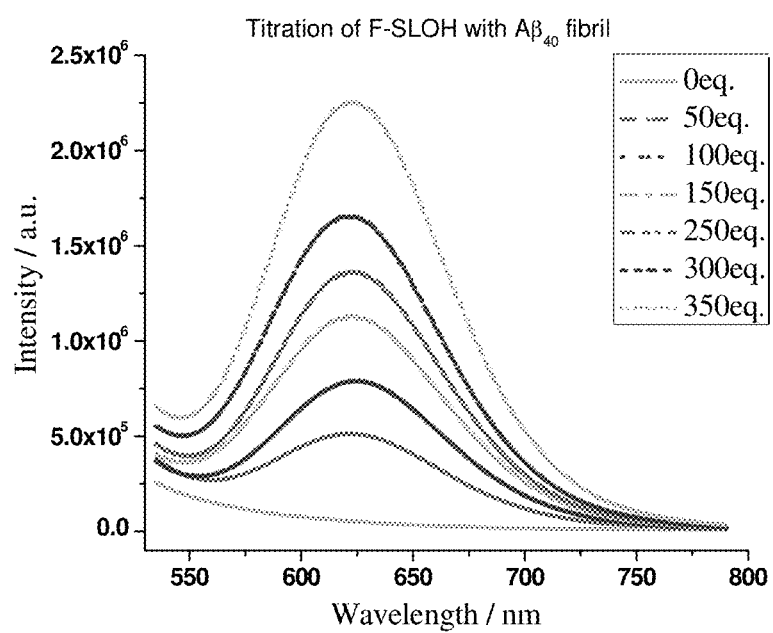
Figure 16D:
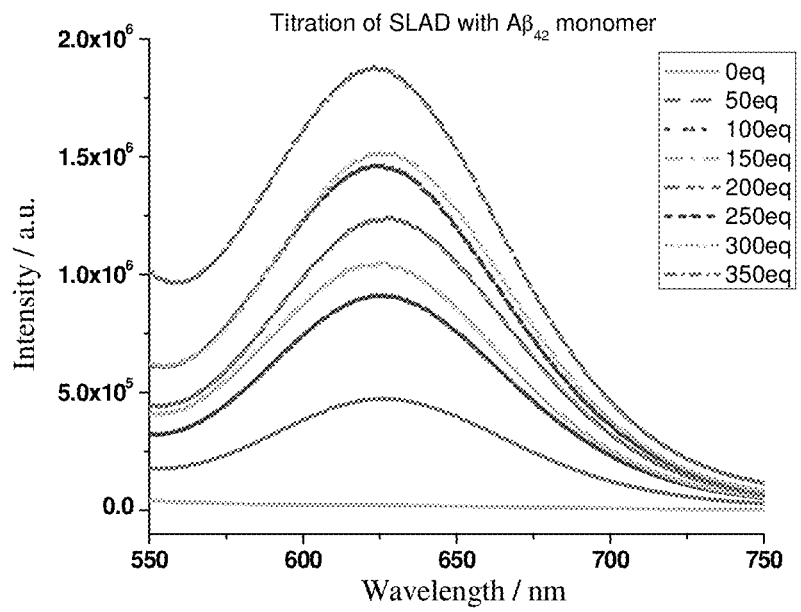
Figure 16E:
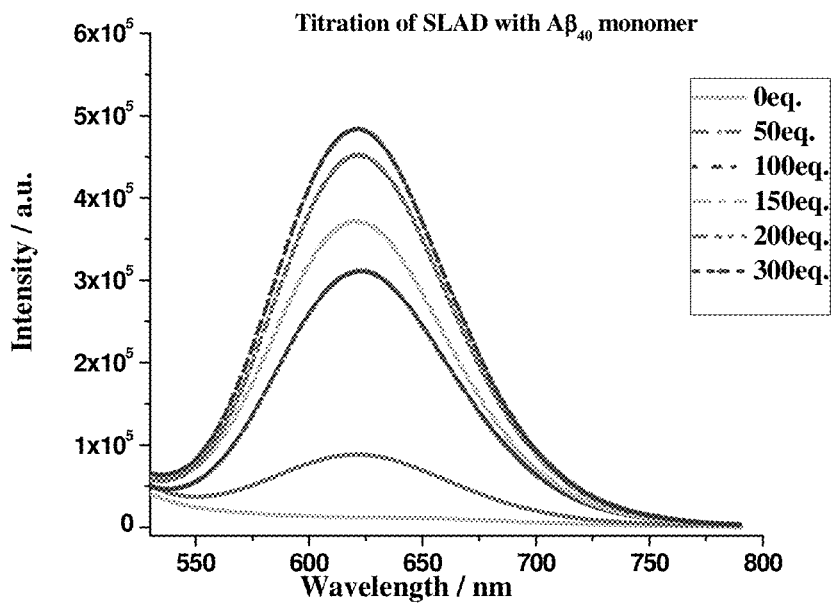
Figure 16F:
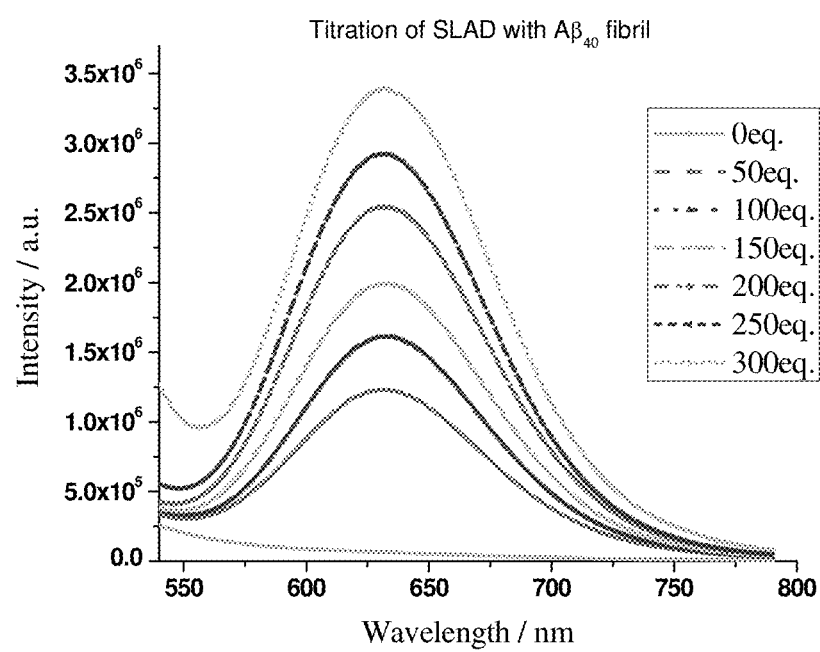
Figure 16G:
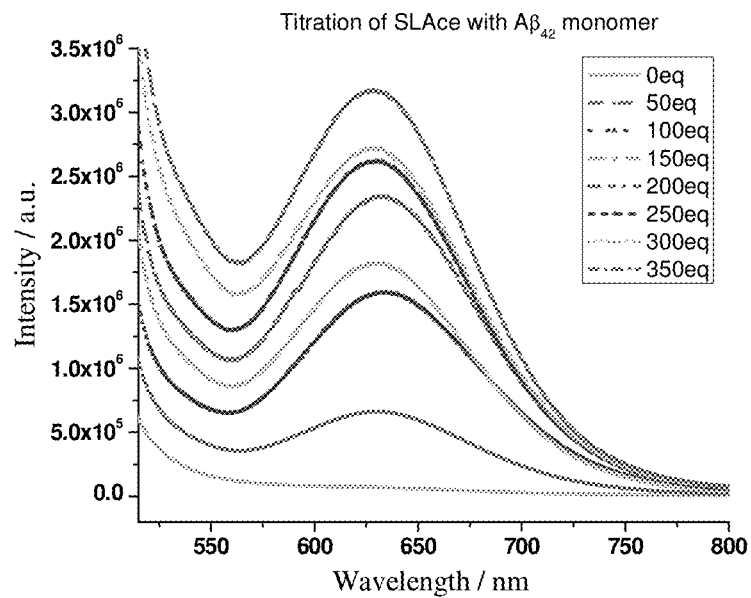
Figure 16H:
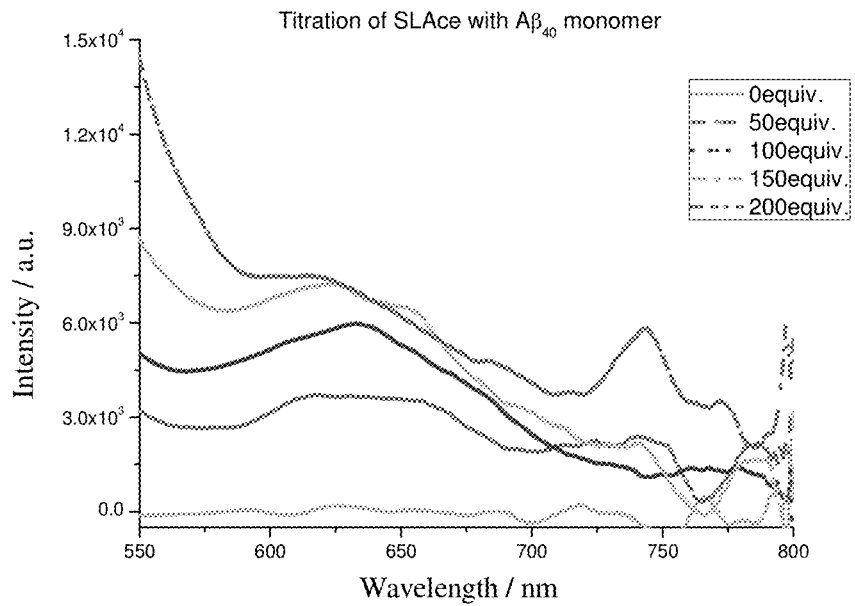
Figure 16I:
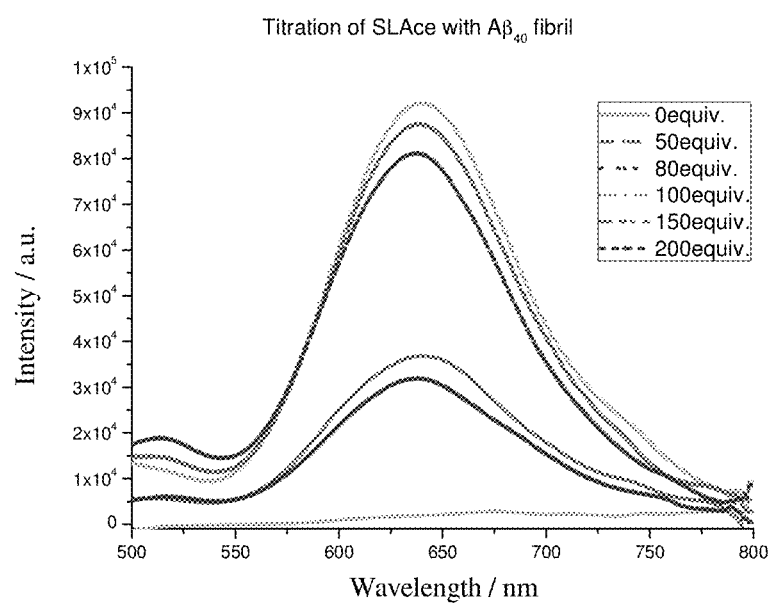
Figure 16J:
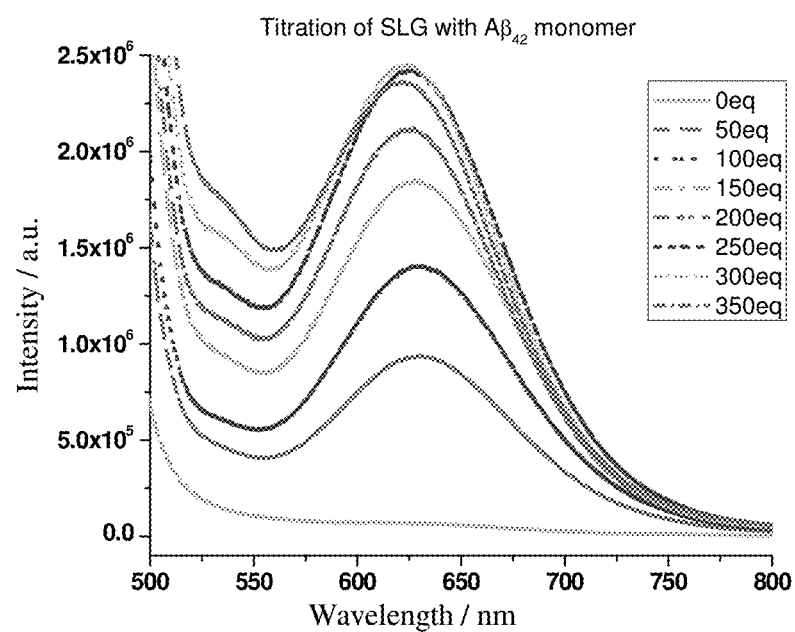
Figure 16K:
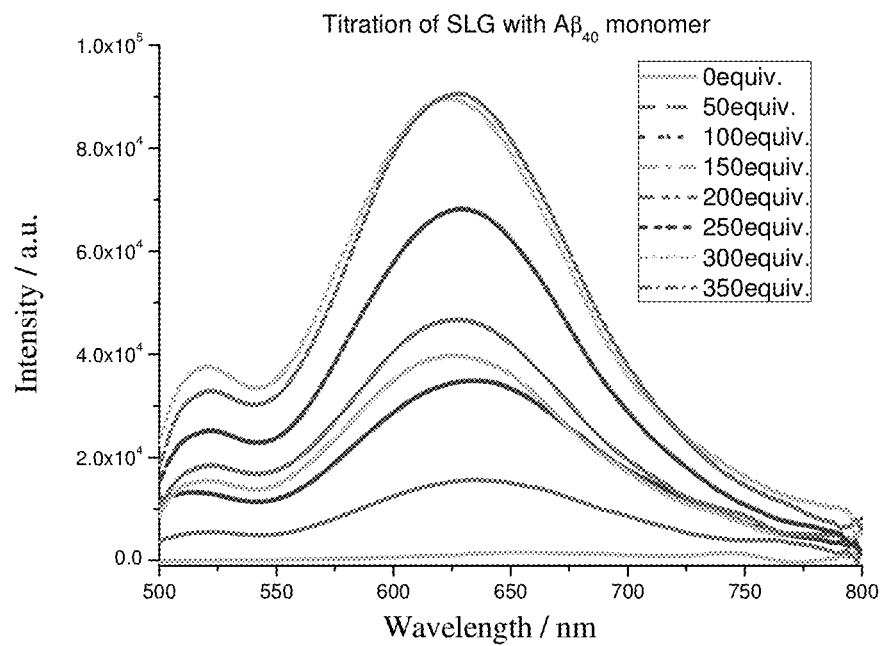
Figure 16L:
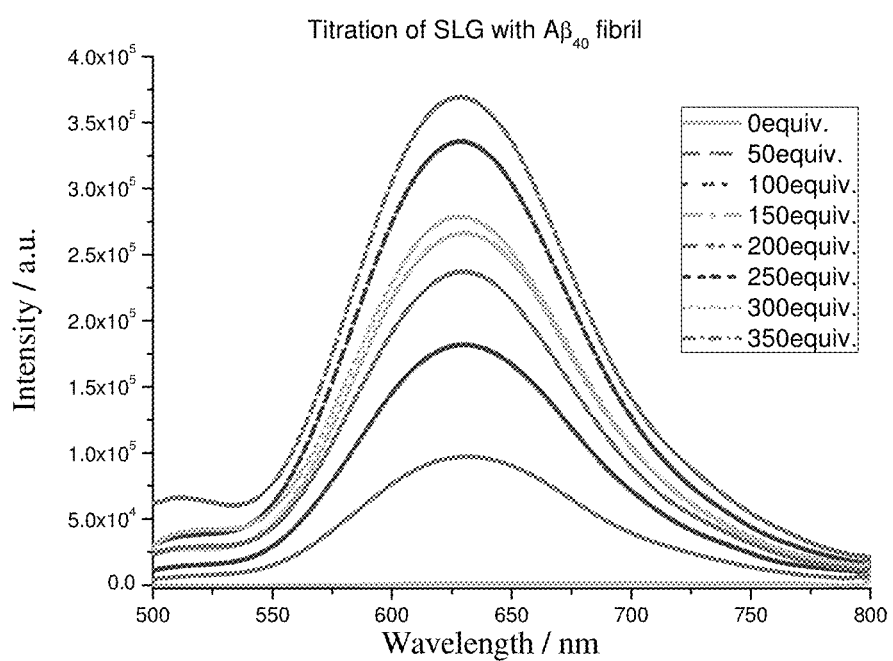

FIG. 15 shows the formula "F-SLOH", "SLAD", "SLAce", and "SLG", respectively.

FIG. 16 shows the fluorescence spectra of F-SLOH in phosphate buffer (1 μM) upon addition of various concentrations of Aβ(1-42) monomer (FIG. 16A), Aβ(1-40) monomer (FIG. 16B) and Aβ(1-40) fibril (FIG. 16C), respectively; the fluorescence spectra of SLAD in phosphate buffer (1 μM) upon addition of various concentrations of Aβ(1-42) monomer (FIG. 16D), Aβ(1-40) monomer (FIG. 16E) and Aβ(1-40) fibril (FIG. 16F), respectively; the fluorescence spectra of SLAce in phosphate buffer (1 μM) upon addition of various concentrations of Aβ(1-42) monomer (FIG. 16G), Aβ(1-40) monomer (FIG. 16H) and Aβ(1-40) fibril (FIG. 16I), respectively; and the fluorescence spectra of SLG in phosphate buffer (1 μM) upon addition of various concentrations of Aβ(1-42) monomer (FIG. 16J), Aβ(1-40) monomer (FIG. 16K) and Aβ(1-40) fibril (FIG. 16L), respectively.

Figure 17:
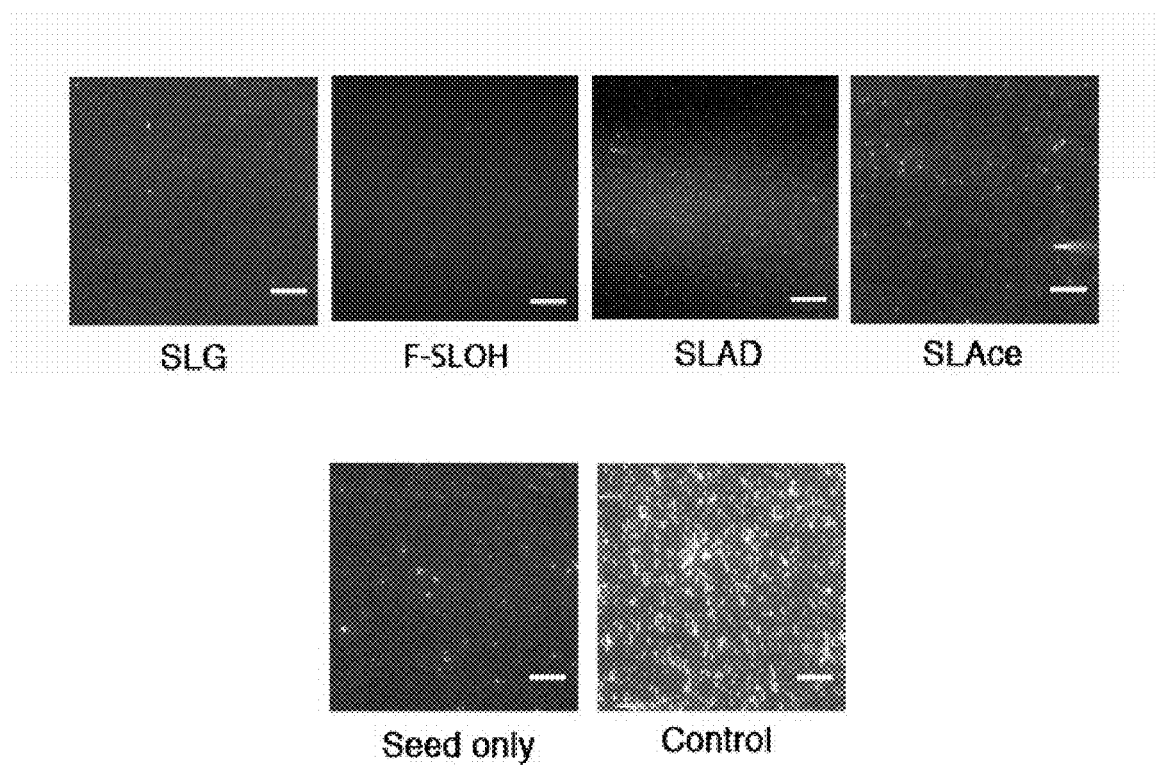

FIG. 17 shows the TIRFM images of Aβ monomer and seeds after incubation with the carbazole-based fluorophores, SLG, F-SLOH, SLAD and SLAce. The panels below show the images of seed only and Aβ fibril formation without the carbazole-based fluorophore for comparison. These images were obtained by an addition of ThT dye excited at 445 nm.

Figure 18A:
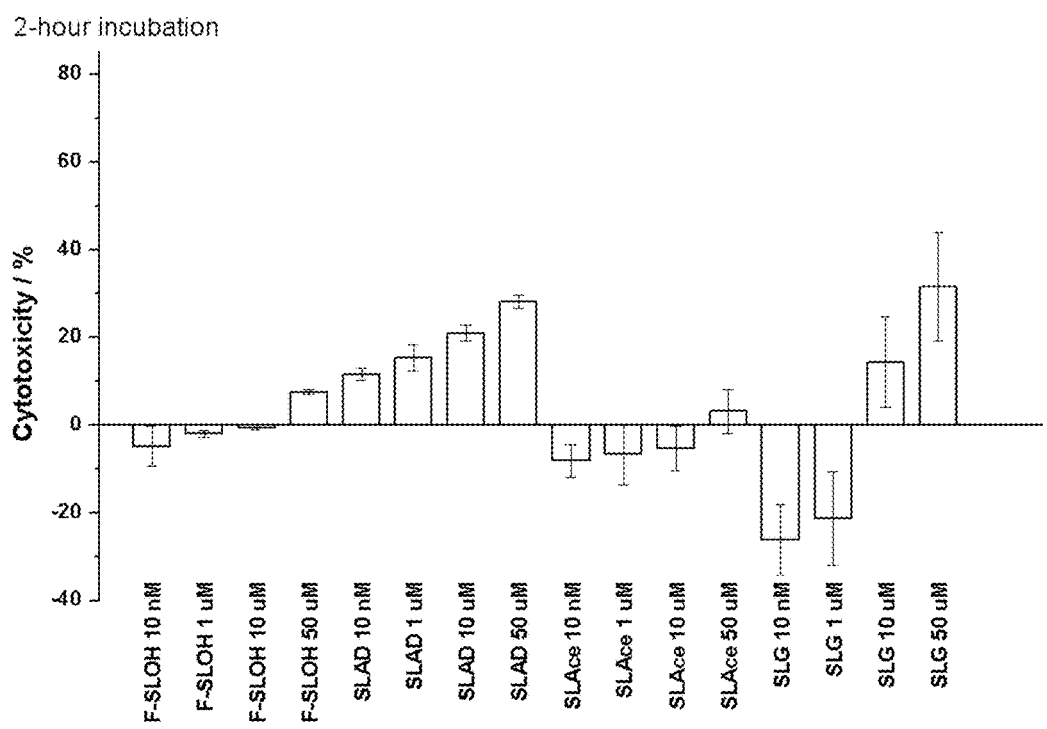
Figure 18B:
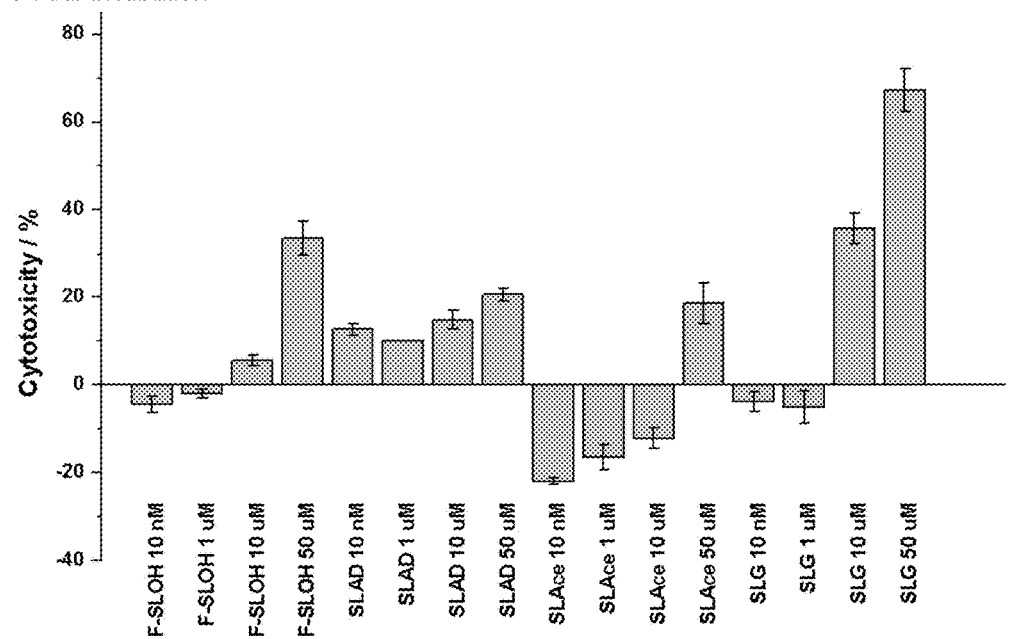
Figure 18C:
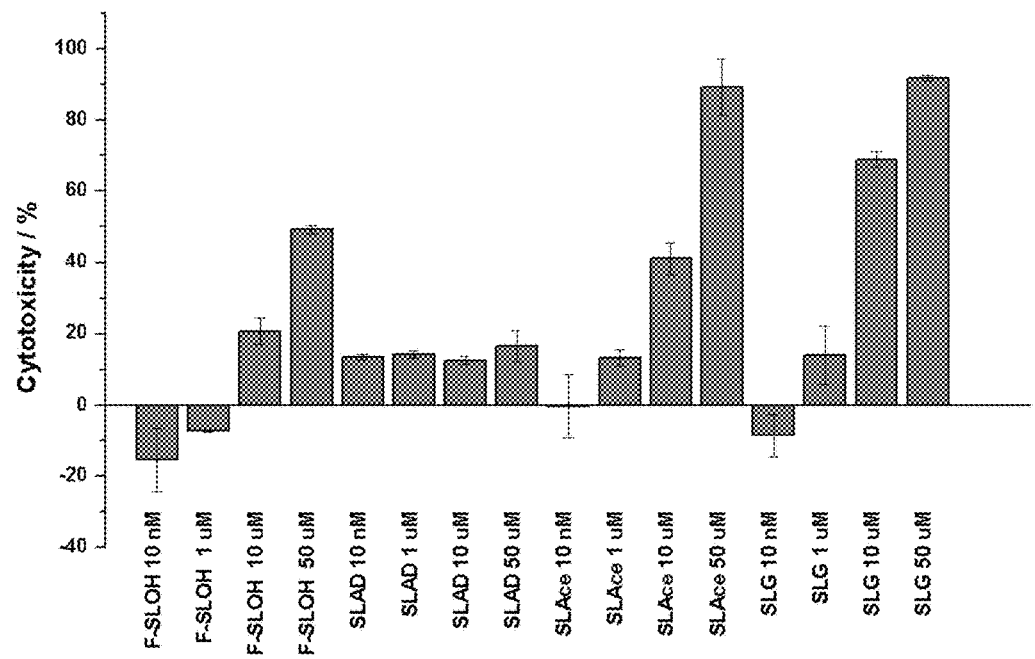

FIG. 18A shows the cytotoxicities of the carbazole-based cyanines, F-SLOH, SLAD, SLAce and SLG towards the SH-SY5Y neuronal cell with MTT assays at 2-hour incubation; FIG. 18B shows the cytotoxicities of the carbazole-based cyanines, F-SLOH, SLAD, SLAce and SLG towards the SH-SY5Y neuronal cell with MTT assays at 6-hour incubation; and FIG. 18C shows the cytotoxicities of the carbazole-based cyanines, F-SLOH, SLAD, SLAce and SLG towards the SH-SY5Y neuronal cell with MTT assays at 24-hour incubation.

Figure 19A:
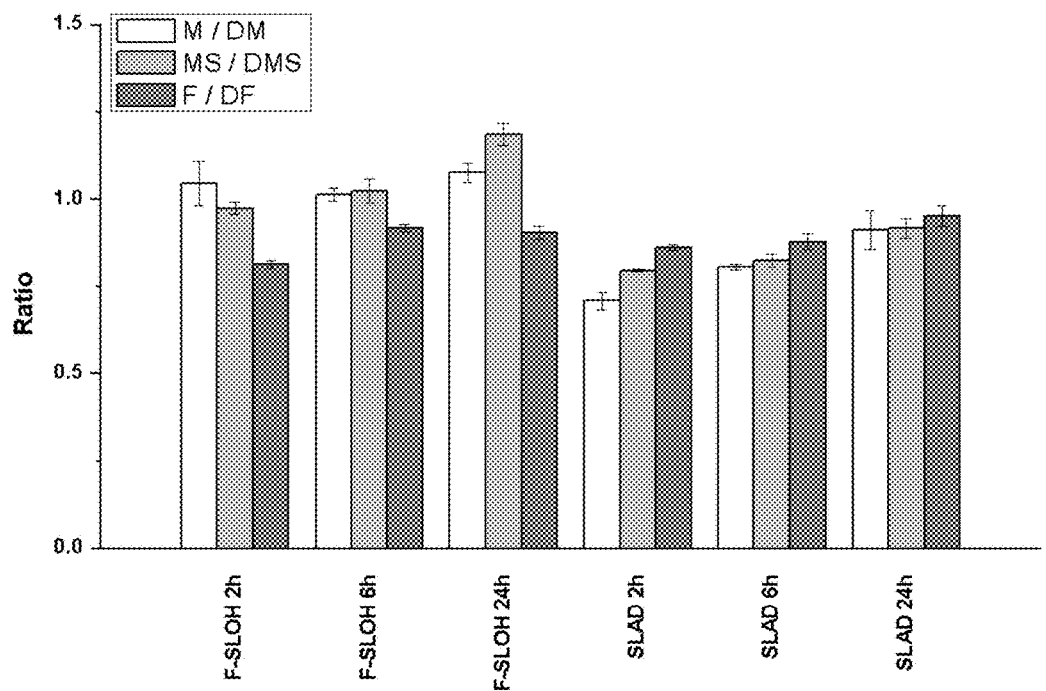
Figure 19B:
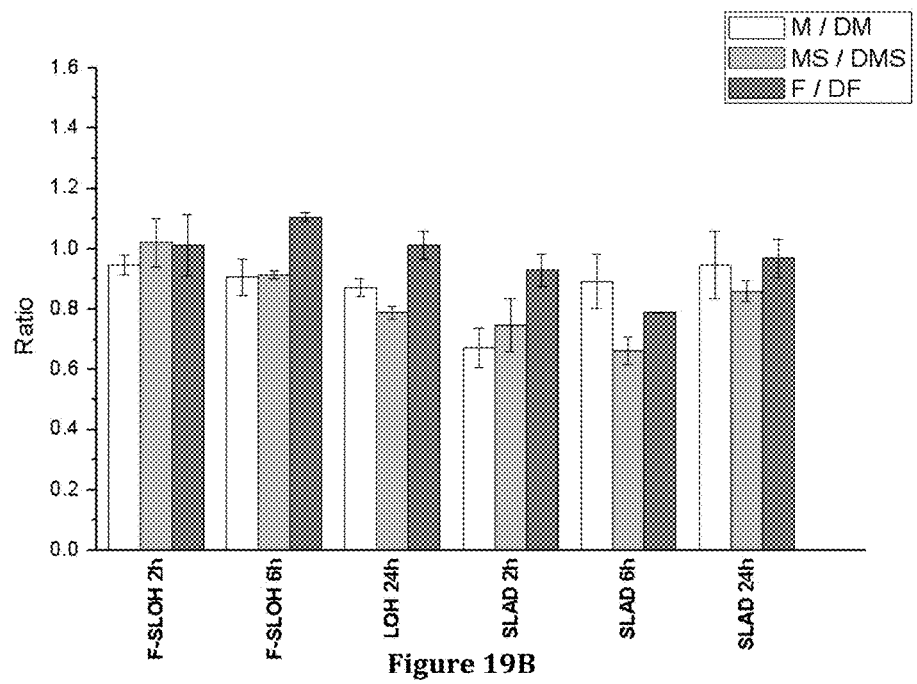

FIG. 19A shows the influence of F-SLOH, and SLAD suppression on the toxicity level against various species of Aβ-induced cytotoxicity towards primary cortical neural cells; FIG. 19B shows the reduction of the ROS induced by the Aβ species in primary cortical neural cells.

Figures 20A, 20B, 20C:
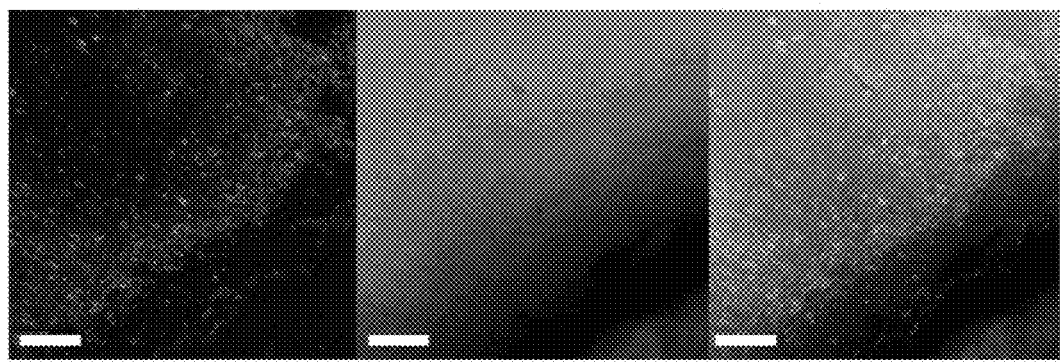
Figures 20D, 20E, 20F:
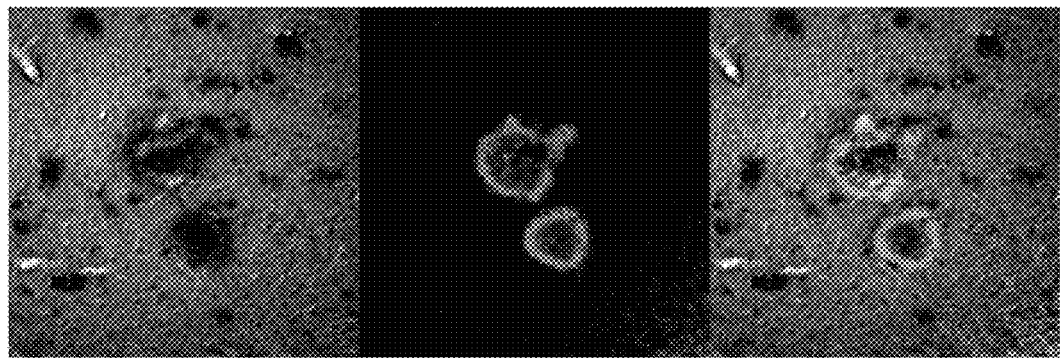

The following figures shows the fluorescence images of mice brain with tail vein injection of SLAD (upper panel) and co-stained with the Aβ labeling dye, and Aβ antibody with DAB stain. FIG. 20A shows fluorescence image corresponding to SLAD fluorescence captured at 550-630 nm under excitation at 488 nm; FIG. 20B shows differential Interference Contrast (DIC) image; and FIG. 20C shows overlapped images of previous two images. FIG. 20D shows differential Interference Contrast (DIC) image of DAB stained brain slide of transgenic mice. FIG. 20E shows fluorescence image of same slide corresponding to SLAD fluorescence captured at 550-630 nm under excitation at 488 nm; and FIG. 20F shows overlapped images of previous two images. The overlapped image revealed the colocalization of fluorescence signals of SLAD and Aβ antibody in cellular components.

Figure 21A:
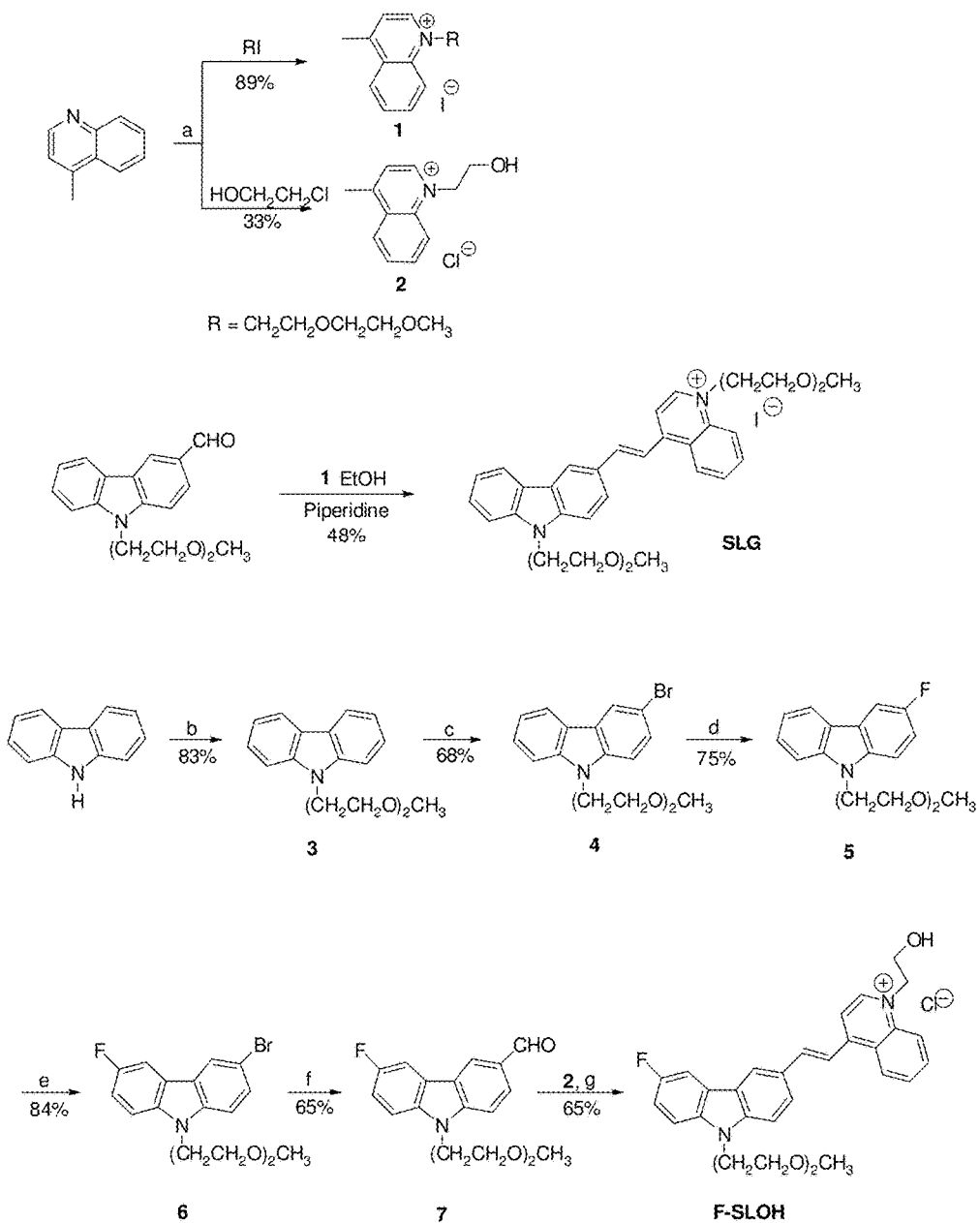
Figure 21B:
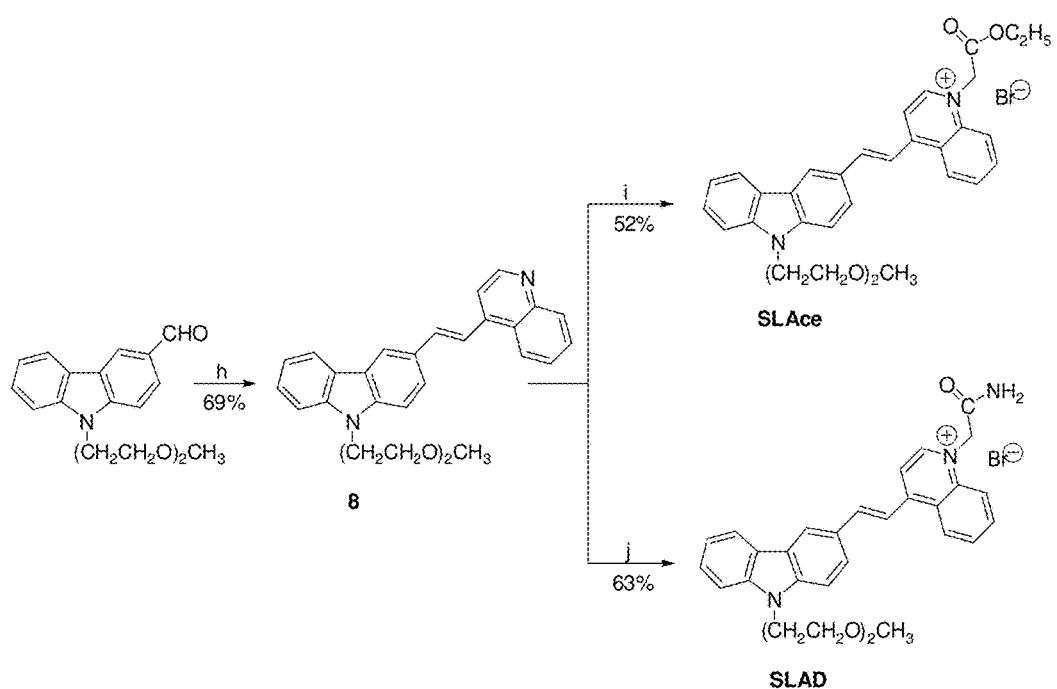

FIG. 21 shows the synthesis of carbazole-based fluorophores, F-SLOH and SLG (FIG. 21A), SLAD and SLAce (FIG. 21B). (Note: Reagents and Conditions: a, MeCN, reflux; b, $ClCH_2CH_2OCH_2CH_2OCH_3$, NaH, DMF, 75° C.; c, NBS, chloroform, 0° C. to r.t.; d, n-BuLi, NFSi, THF, −78° C. to r.t.; e, NBS, chloroform, 0° C. to r.t.; f, n-BuLi, DMF, THF, −78° C. to r.t.; g, MeOH, reflux; h, TMSCl, DMF, 100° C., sealed tube; i, $CH_3CH_2OCOCH_2Br$, ethanol, r.t.; j, $NH_2COCH_2Br$, MeCN, reflux.)

Figure 22A:
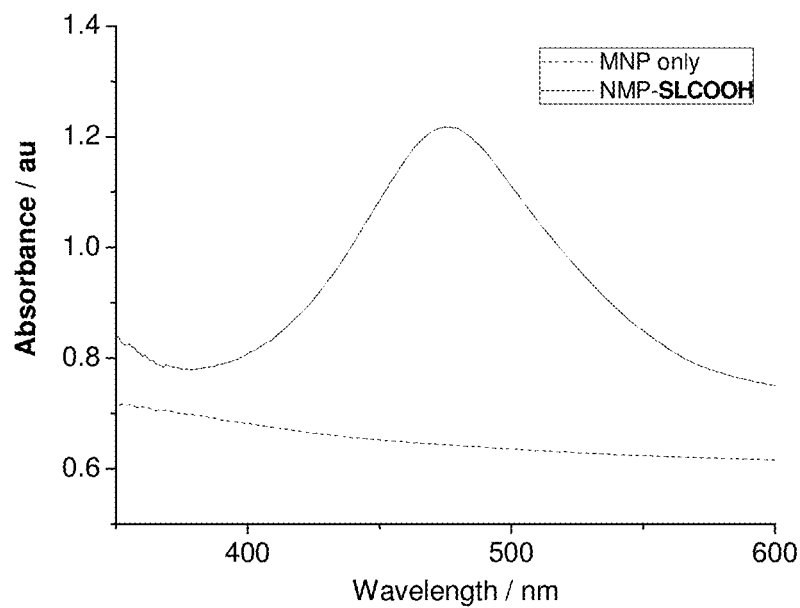
Figure 22B:
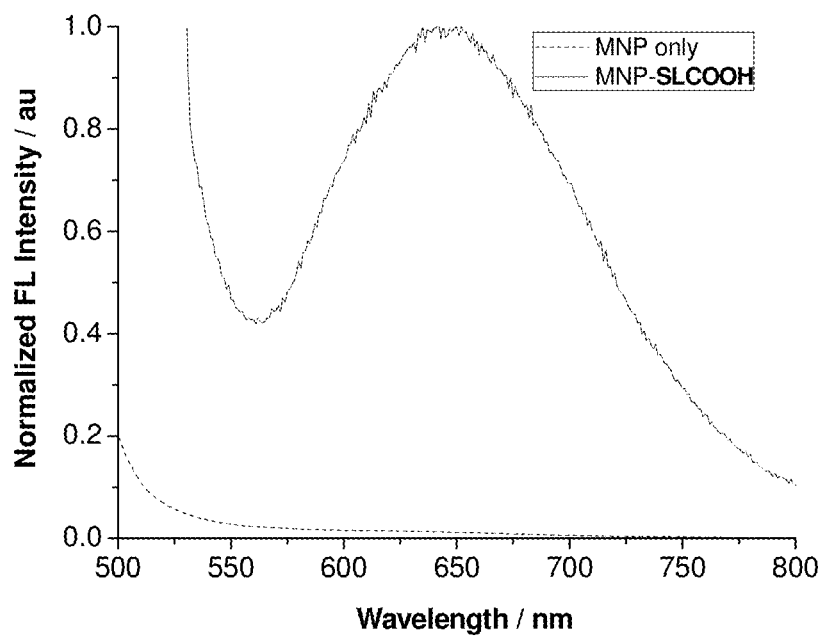
Figure 22C:
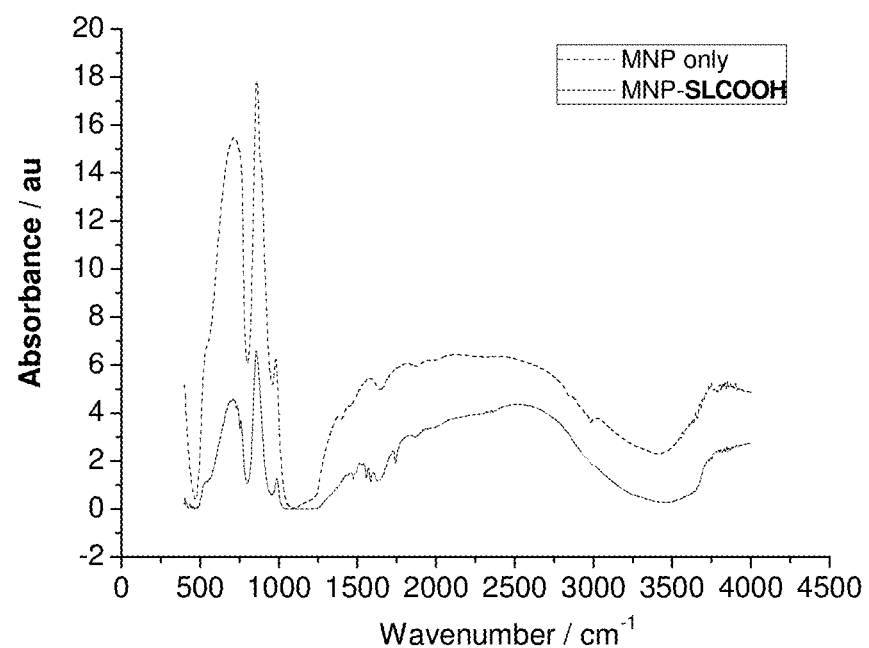

FIG. 22A shows absorption of the magnetic nanoparticles (MNP) before and after the conjugation with SLCOOH; FIG. 22B shows emission of the magnetic nanoparticles (MNP) before and after the conjugation with SLCOOH; and FIG. 22C shows IR spectra of the magnetic nanoparticles (MNP) before and after the conjugation with SLCOOH.

FIG. 23A shows TEM images of $SiO_2@Fe_3O_4$ with Aβ fibrils and FIG. 23B shows TEM images of SLCOOH-conjugated $SiO_2@Fe_3O_4$ nanoparticles with Aβ fibrils.

Figure 24:
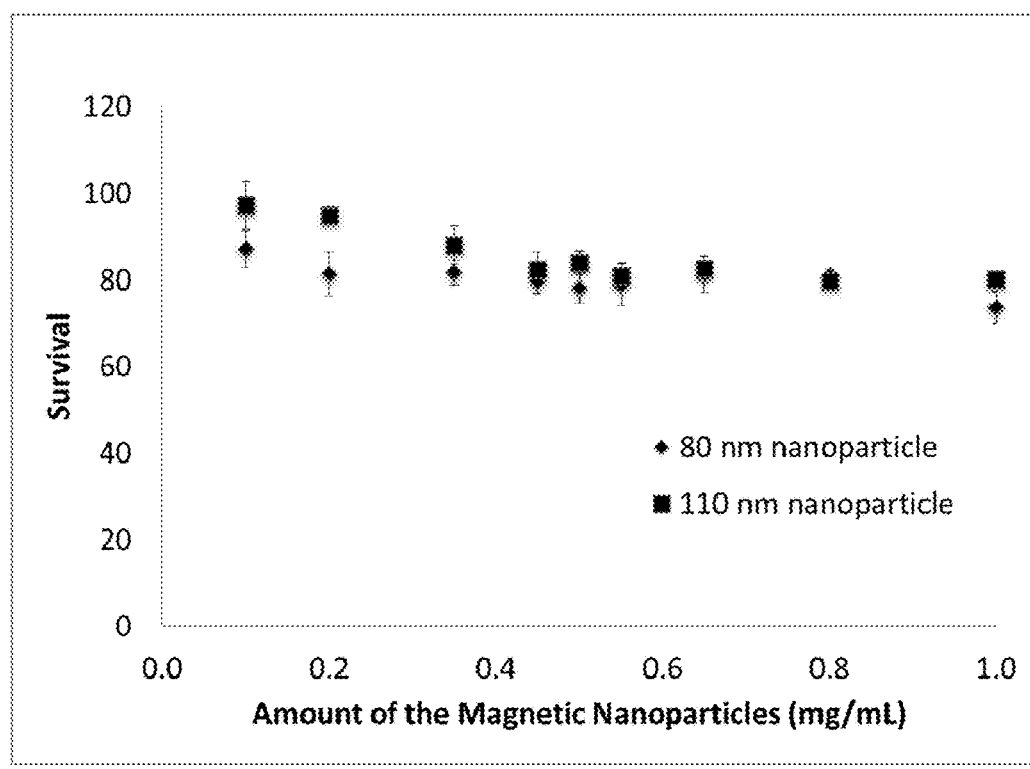

FIG. 24 shows cell viability values (%) of cells treated with different concentrations of nanoparticles in different size, which is assessed by MTT Assays.

Figure 25A:
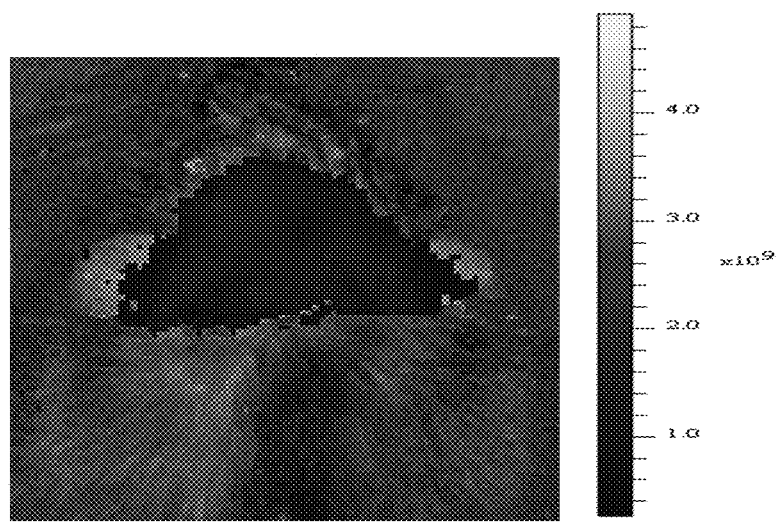
Figure 25B:
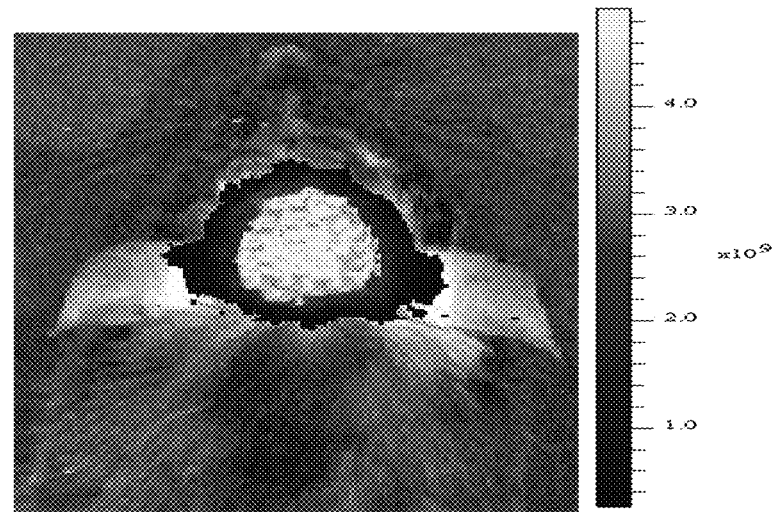
Figure 25C:
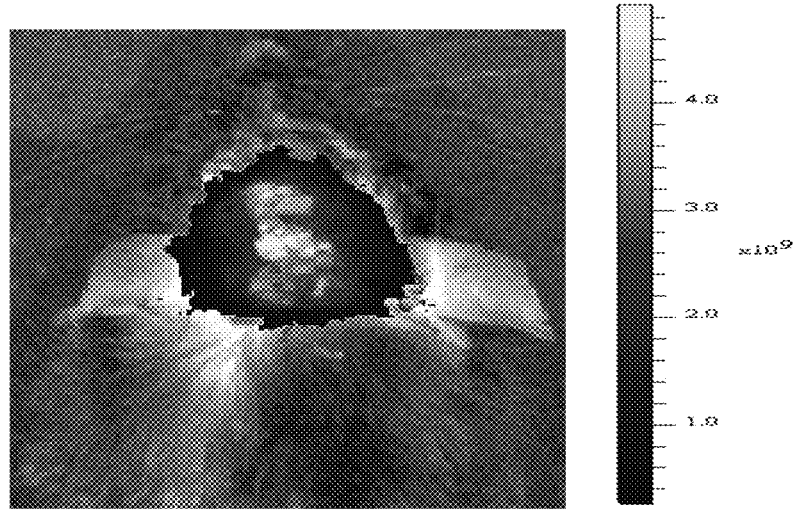
Figure 25D:
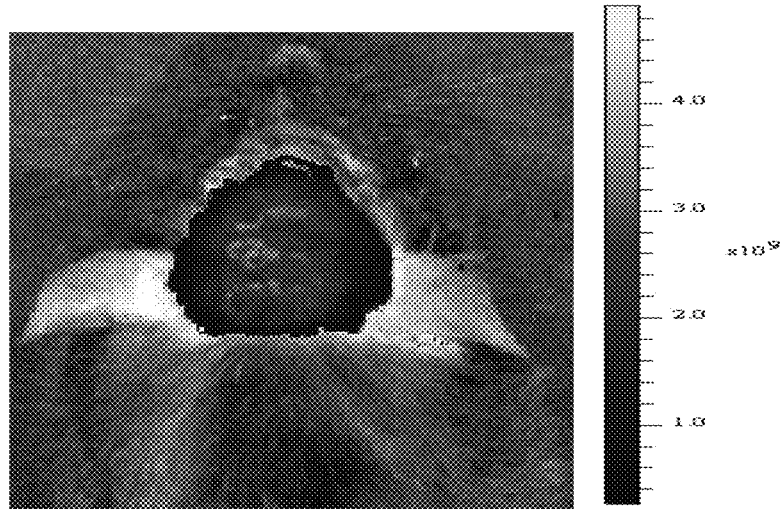

FIG. 25A shows in-vivo NIR fluorescence images of brain region of a 12-month-old APP/PS1 Aβ-over-expressing transgenic mouse before intravenous (IV) injection of 100 μL SLCOOH-conjugated $SiO_2@Fe_3O_4$ nanoparticles (10 mg/kg) and after the IV injection at different time points: FIG. 25B shows the result at 30 min; FIG. 25C shows the result at 60 min; and FIG. 25D shows the result at 180 min. $\lambda_{ex}$=500 nm, $\lambda_{em}$=620-660 nm.

Figure 26A:
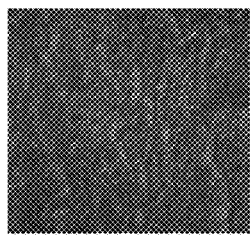
Figure 26B:
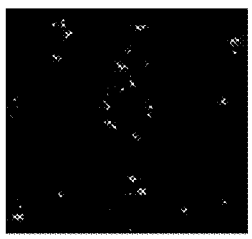
Figure 26C:
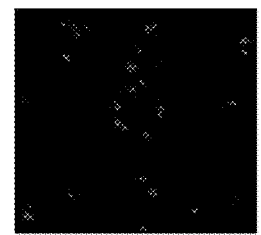
Figure 26D:
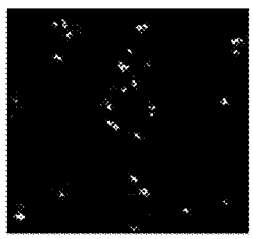

The following figures show histological staining of the brain slice from a 12-month-old APP/PS1 Tg mouse: FIG. 26A shows a phase contrast image; FIG. 26B shows green fluorescent signal from cells labeled with SLCOOH-conjugated SiO$_2$@Fe$_3$O$_4$ nanoparticles ($\lambda_{ex}$=500 nm, $\lambda_{em}$=620-680 nm); and FIG. 26C shows red fluorescent signal from cells labeled with ThT ($\lambda_{ex}$=405 nm, $\lambda_{em}$=460-490 nm); FIG. 26D is the superimposed image of FIG. 26B and FIG. 26C.

Figure 27A:
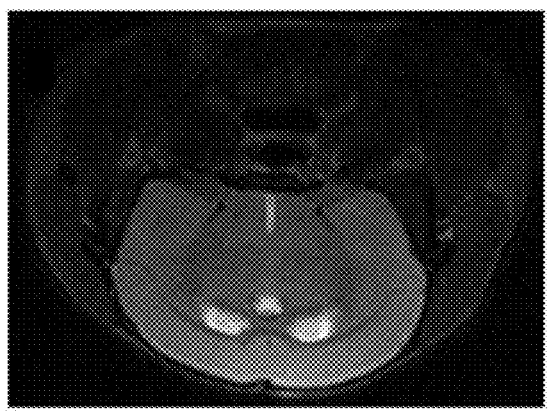
Figure 27B:
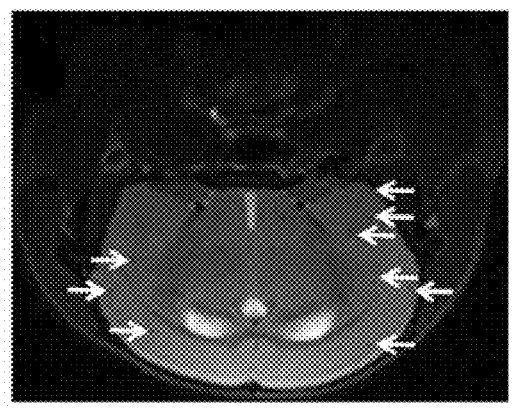

FIG. 27A shows in vivo T$_2$ MRI images of a live 3-month-old APP/PS1 transgenic mouse brain before a tail-vein injection of SLCOOH-conjugated SiO$_2$@Fe$_3$O$_4$ nanoparticles (100 μL, 10 mg/mL); and FIG. 27B shows in vivo T$_2$ MRI images of a live 3-month-old APP/PS1 transgenic mouse brain after a tail-vein injection of SLCOOH-conjugated SiO$_2$@Fe$_3$O$_4$ nanoparticles (100 μL, 10 mg/mL) at 2 hours.

Figure 28A:
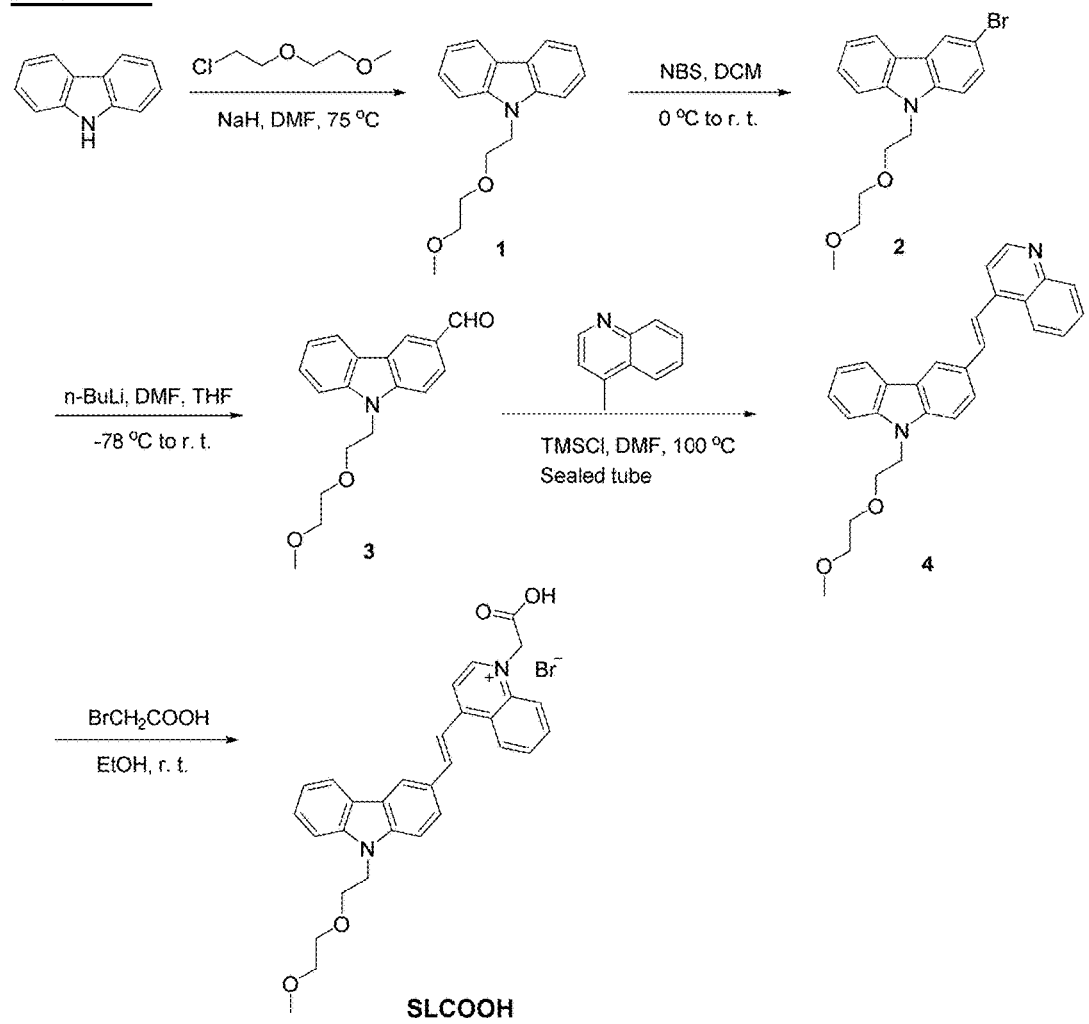
Figure 28B:
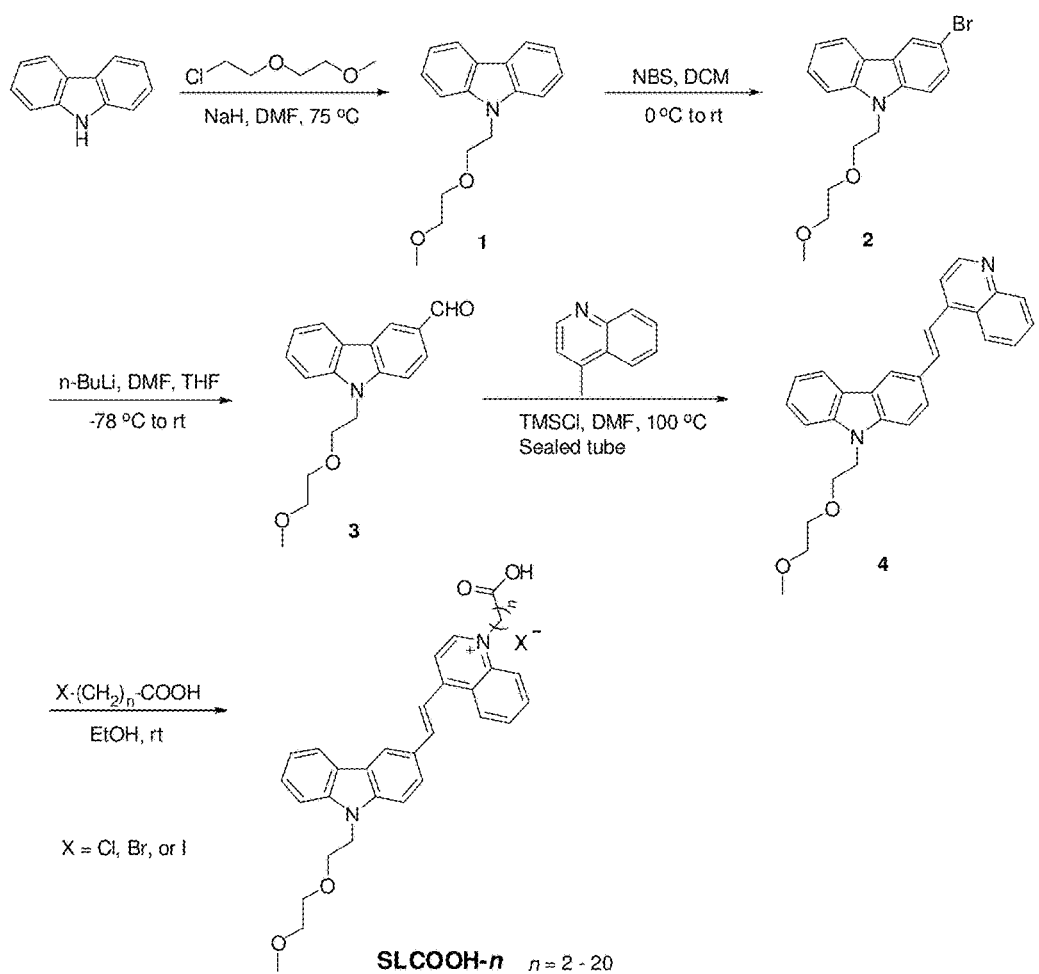

FIG. 28 shows synthesis schemes of the presently claimed carbazole-based fluorophores, SLCOOH (Scheme 1A; FIG. 28A) and SLCOOH-n (Scheme 1B; FIG. 28B), for conjugating with magnetic nanoparticles.

Figure 29A:
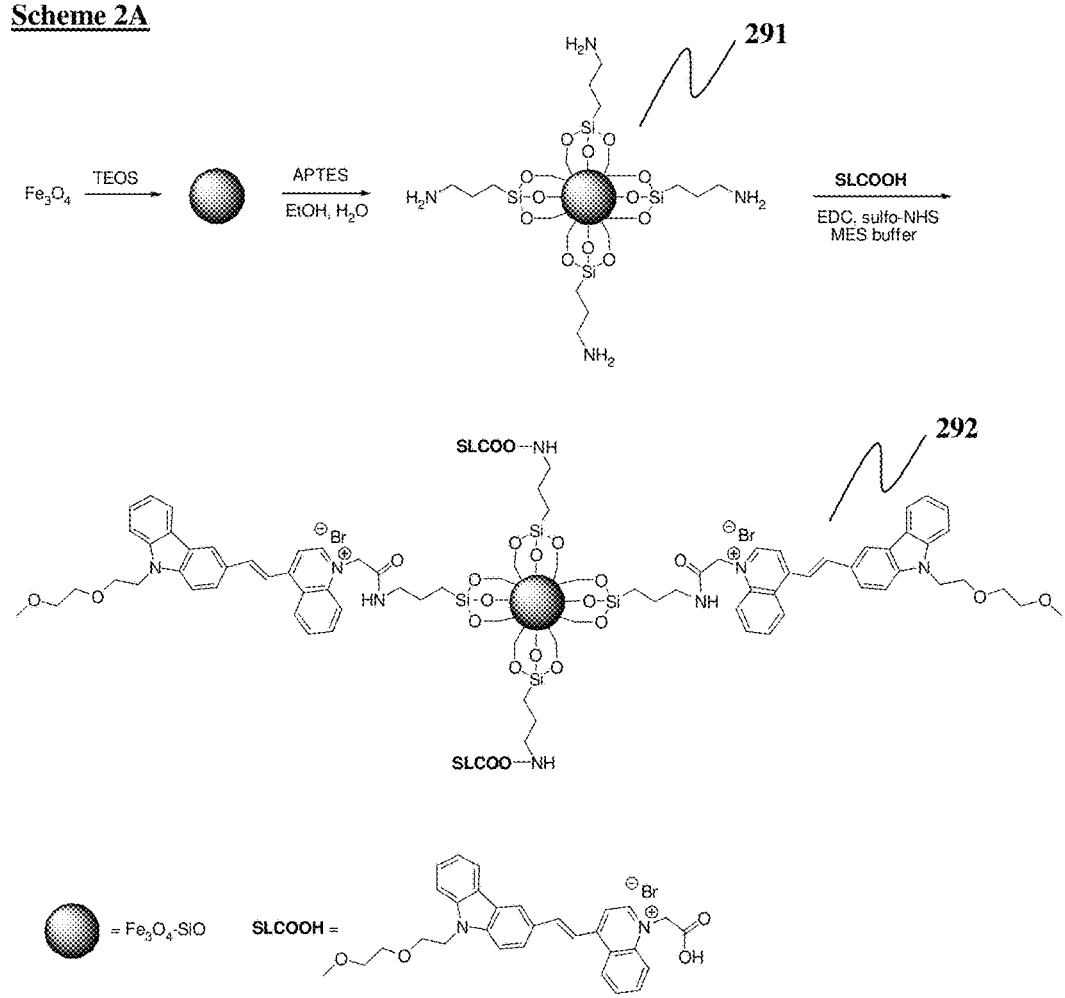
Figure 29B:
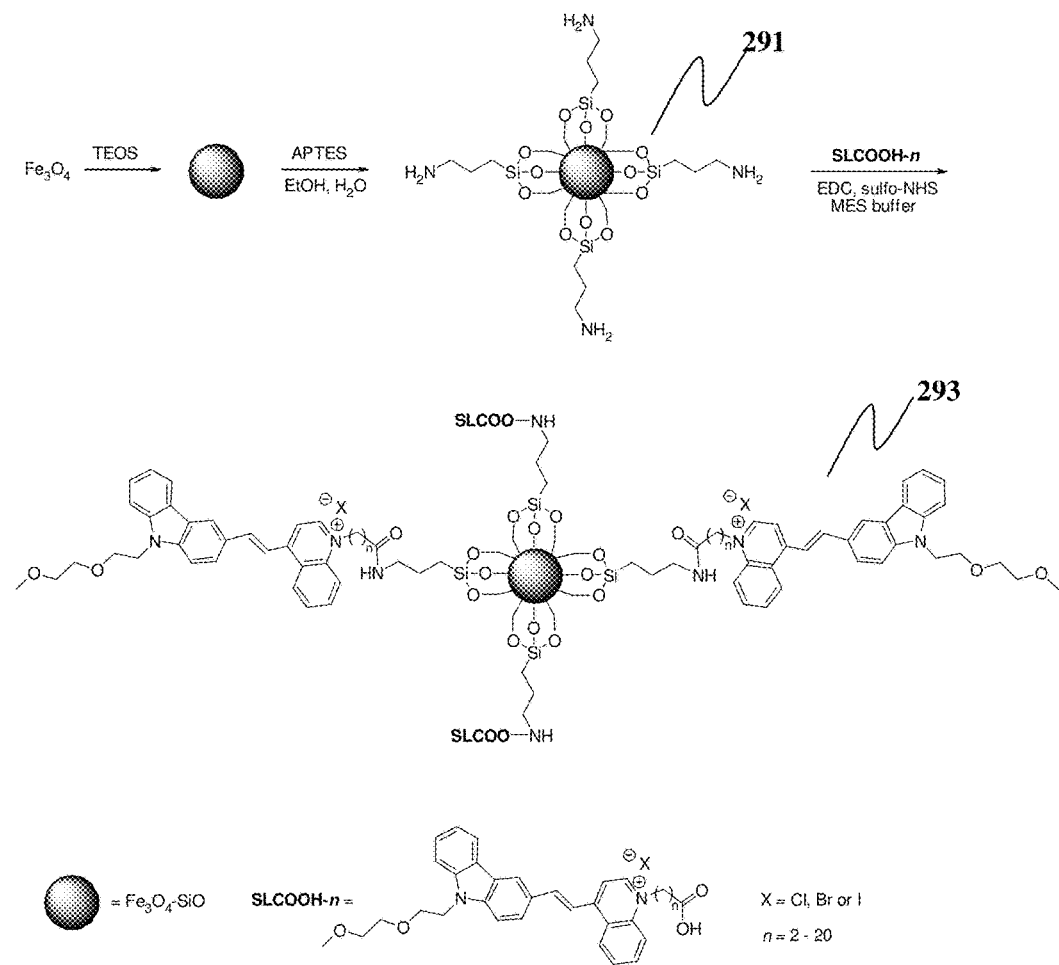

FIG. 29 shows synthesis schemes of the presently claimed conjugate of SiO$_2$@Fe$_3$O$_4$ nanoparticles with SLCOOH (Scheme 2A; FIG. 29A) and SLCOOH-n (Scheme 2B; FIG. 29B) cyanine dyes using amide formation chemistry.

DETAILED DESCRIPTION OF THE INVENTION

The presently claimed invention is further illustrated by the following experiments or embodiments which should be understood that the subject matters disclosed in the experiments or embodiments may only be used for illustrative purpose but are not intended to limit the scope of the presently claimed invention:

The general chemical structures of carbazole-based fluorophores, including S or V series, are shown as follows:

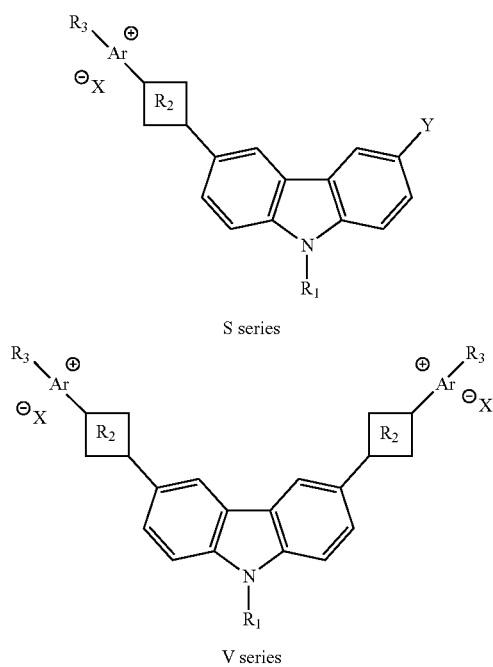

S series

V series

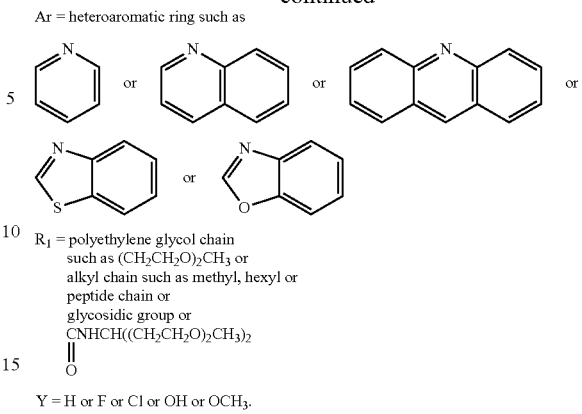

Ar = heteroaromatic ring such as

R$_1$ = polyethylene glycol chain such as (CH$_2$CH$_2$O)$_2$CH$_3$ or alkyl chain such as methyl, hexyl or peptide chain or glycosidic group or CNHCH((CH$_2$CH$_2$O)$_2$CH$_3$)$_2$ ‖ O Y = H or F or Cl or OH or OCH$_3$.

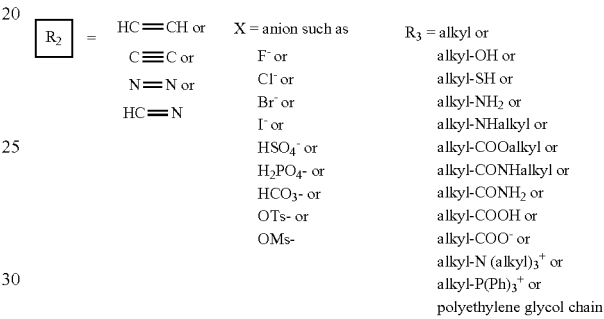

| R$_2$ = | HC=CH or C≡C or N=N or HC=N | X = anion such as F⁻ or Cl⁻ or Br⁻ or I⁻ or HSO$_4$⁻ or H$_2$PO$_4$⁻ or HCO$_3$⁻ or OTs⁻ or OMs⁻ | R$_3$ = alkyl or alkyl-OH or alkyl-SH or alkyl-NH$_2$ or alkyl-NHalkyl or alkyl-COOalkyl or alkyl-CONHalkyl or alkyl-CONH$_2$ or alkyl-COOH or alkyl-COO⁻ or alkyl-N(alkyl)$_3$⁺ or alkyl-P(Ph)$_3$⁺ or polyethylene glycol chain | wherein Ar is a heteroaromatic ring selected from the group consisting of pyridinyl, substituted pyridinyl, quinolinyl, substituted quinolinyl, acridinyl, substituted acridinyl, benzothiazolyl, substituted benzothiazolyl, benzoxazolyl, and substituted benzoxazolyl; R$_1$ is a radical selected from the group consisting of polyethylene glycol chain, alkyl, substituted alkyl, peptide chain, glycosidyl, and C(O)NHCH ((CH$_2$CH$_2$O)$_2$CH$_3$)$_2$; R$_2$ is selected from the group consisting of ethenyl, ethynyl, azo and azomethinyl; R$_3$ is a radical selected from the group consisting of alkyl, HO-alkyl, HS-alkyl, H$_2$N-alkyl, HNalkyl-alkyl, alkyl-COOalkyl, alkyl-CONH$_2$, alkyl-CONHalkyl, HOOC-alkyl, ⁻OOC-alkyl, (alkyl)$_3$N⁺-alkyl, and (Ph)$_3$P⁺-alkyl and polyethylene glycol chain; X is an anion selected from the group consisting of F, Cl, Br, I, HSO$_4$, H$_2$PO$_4$, HCO$_3$, tosylate, and mesylate; Y is selected from the group consisting of H, F, Cl, OH, OCH$_3$, and R$_2$—Ar—R$_3$, wherein Ar is a heteroaromatic ring selected from the group consisting of pyridinyl, substituted pyridinyl, quinolinyl, substituted quinolinyl, acridinyl, substituted acridinyl, benzothiazolyl, substituted benzothiazolyl, benzoxazolyl, and substituted benzoxazolyl; R$_2$ is selected from the group consisting of ethenyl, ethynyl, azo and azomethinyl; R$_3$ is a radical selected from the group consisting of alkyl, HO-alkyl, HS-alkyl, H$_2$N-alkyl, HNalkyl-alkyl, alkyl-COOalkyl, alkyl-CONH$_2$, alkyl-CONHalkyl, alkyl-COOH, alkyl-COO⁻, (alkyl)$_3$N⁺-alkyl, and (Ph)$_3$P⁺-alkyl, and polyethylene glycol chain.

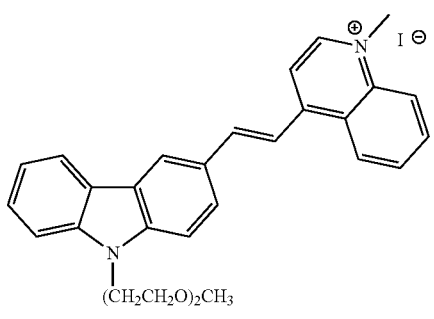

SLM

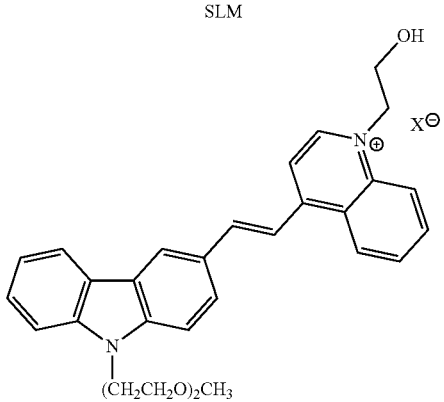

SLOH

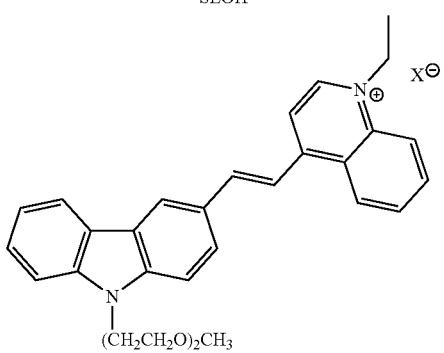

SLE

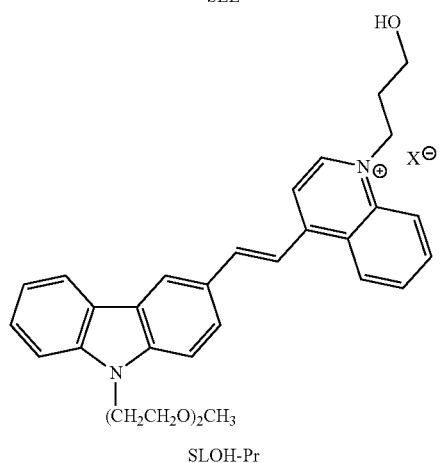

SLOH-Pr

In one embodiment, Ar is a quinolinyl or substituted quinolinyl; $R_1$ is a 2-(2-methoxyethoxy)ethoxy; $R_2$ is an ethenyl; $R_3$ is a methyl, 2-hydroxyethyl, ethyl or 3-hydroxypropyl; and X is a chloride, bromide or iodide, and the compounds of which are represented by the above formula "SLM", "SLOH", "SLE" and "SLOH-Pr", respectively.

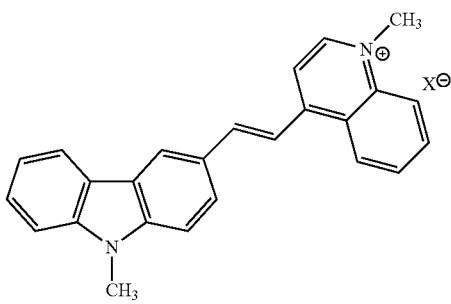

Me-SLM

In another embodiment, Ar is a quinolinyl or substituted quinolinyl; $R_1$ is a methyl; $R_2$ is an ethenyl; $R_3$ is a methyl; and X is a chloride, bromide or iodide, the compounds of which are represented by the above formula Me-SLM.

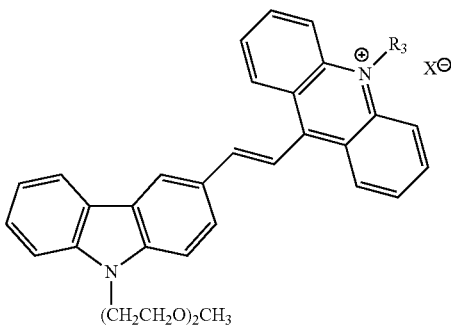

SAM: $R_3$ = $CH_3$
SAOH: $R_3$ = $CH_2CH_3OH$

In a further embodiment, Ar is an acridinyl or substituted acridinyl; $R_1$ is a 2-(2-methoxy-ethoxy)ethoxy; $R_2$ is an ethenyl; $R_3$ is a methyl or 2-hydroxyethyl; and X is selected from a chloride, bromide or iodide, and the fluorophores of which are represented by the above formula SAM and SAOH, respectively, where the difference between the compounds of SAM and SAOH is the substitutent at $R_3$.

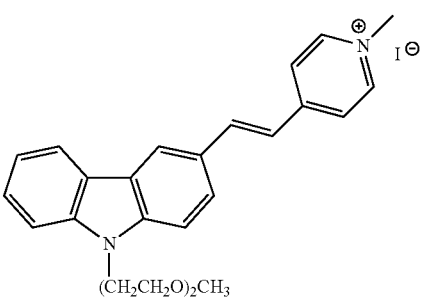

SPM

-continued

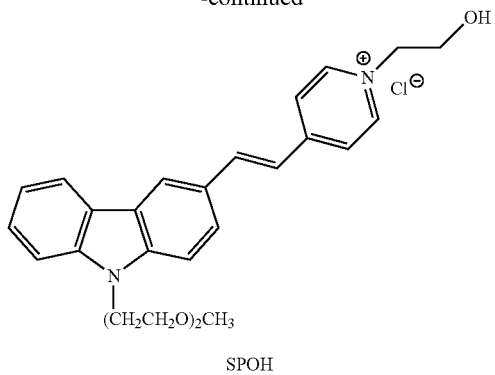

SPOH

In other embodiment, Ar is selected from a pyridinyl or substituted pyridinyl, $R_1$ is a 2-(2-methoxyethoxy)ethoxy; $R_2$ is an ethenyl; $R_3$ is selected from a methyl or 2-hydroxyethyl; and X is selected from a chloride, bromide or iodide, the compounds of which are represented by the formula SPM and SPOH, respectively.

Figure 1A:
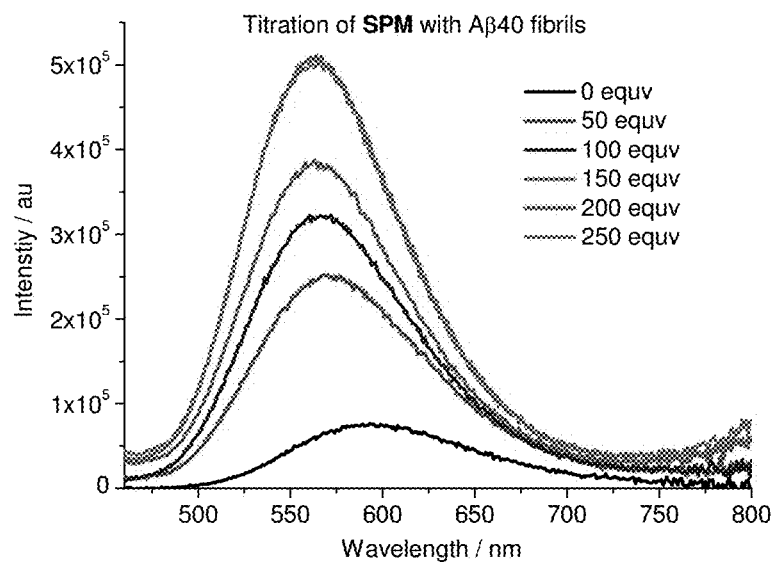
FIG. 1A shows the fluorescence spectra of SPM in various concentrations of Aβ(1-40) fibrils.
Figure 1B:
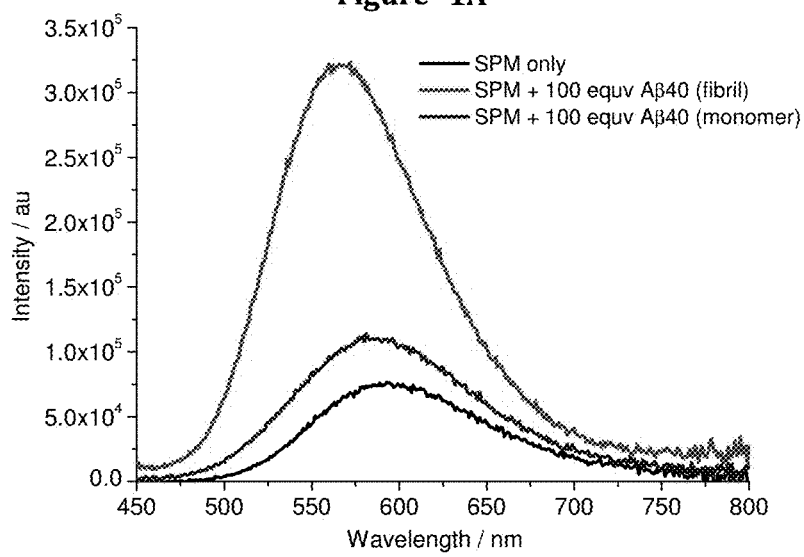
FIG. 1B shows the fluorescence spectra of SPM on its own and in the presence of two different forms of $A\beta_{40}$.
Figure 1C:
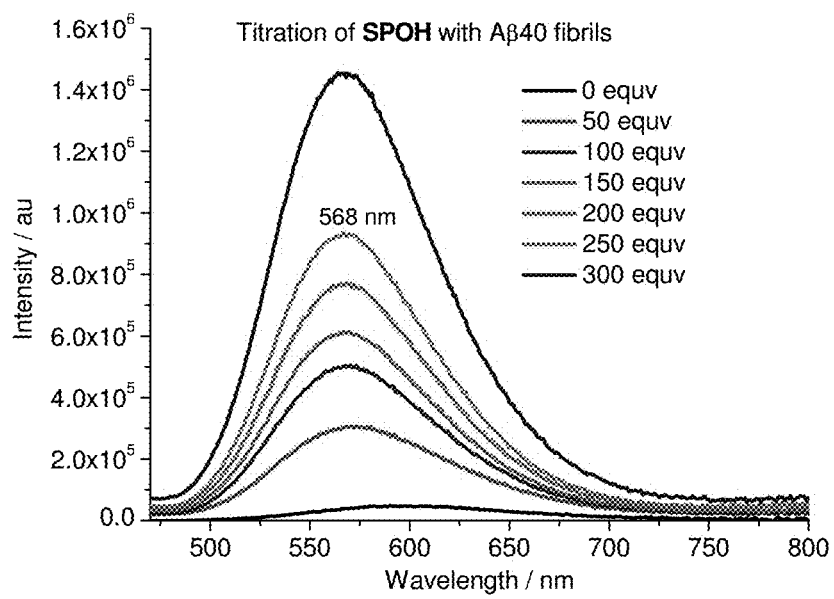
FIG. 1C shows the fluorescence spectra of SPOH in various concentrations of Aβ(1-40) fibrils.
Figure 1D:
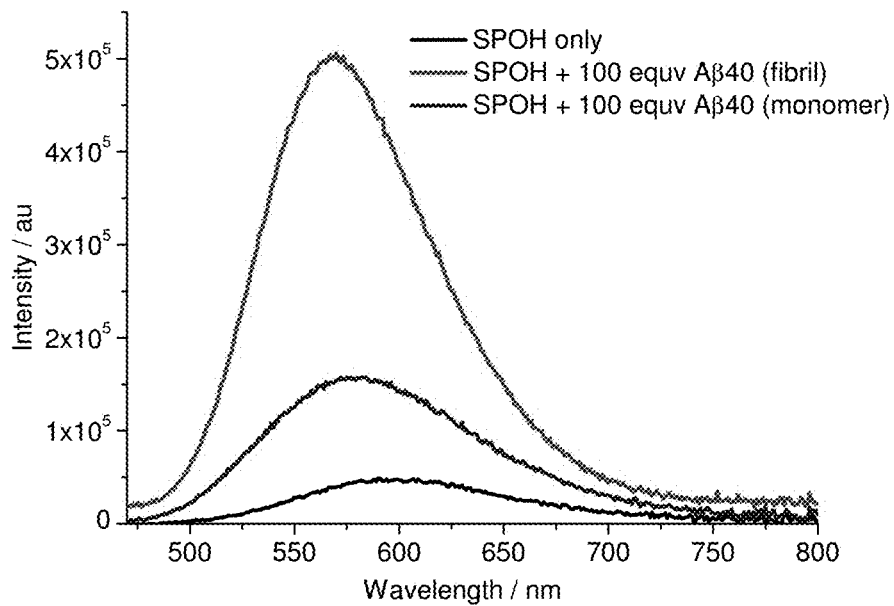
FIG. 1D shows the fluorescence spectra of SPOH on its own and in the presence of two different forms of $A\beta_{40}$.
Figure 1E:
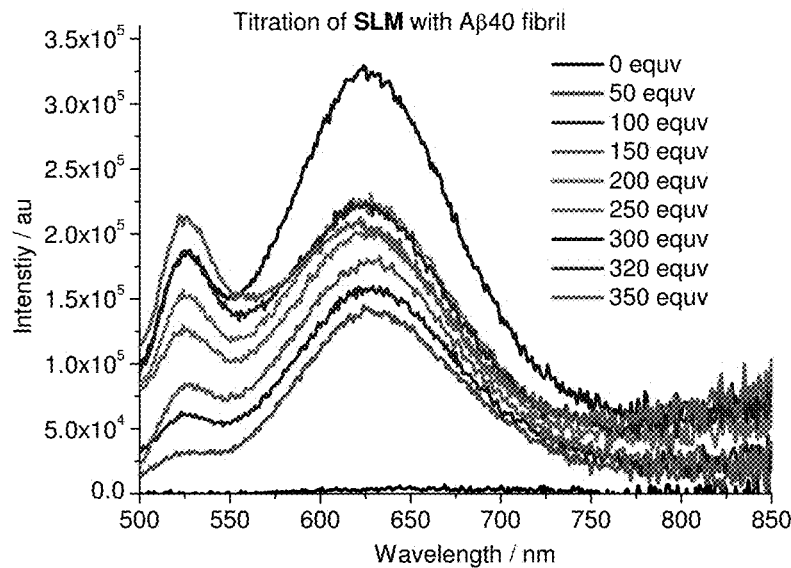
FIG. 1E shows the fluorescence spectra of SLM in various concentrations of Aβ(1-40) fibrils.
Figure 1F:
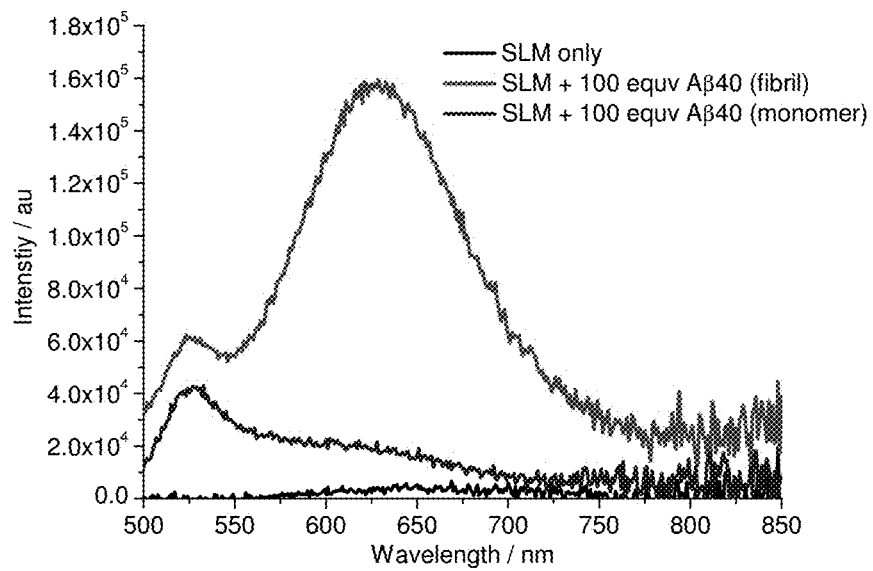
FIG. 1F shows the fluorescence spectra of SLM on its own and in the presence of two different forms of $A\beta_{40}$.
Figure 1G:
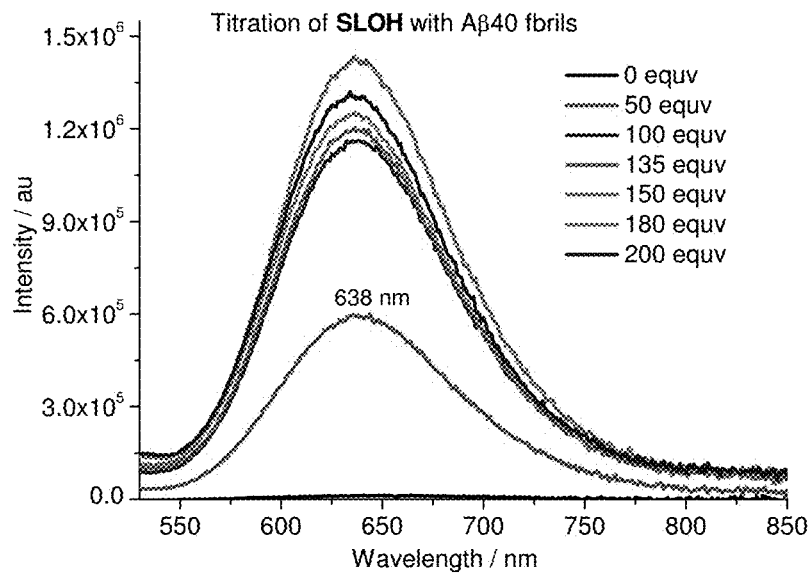
FIG. 1G shows the fluorescence spectra of SLOH in various concentrations of Aβ(1-40) fibrils.
Figure 1H:
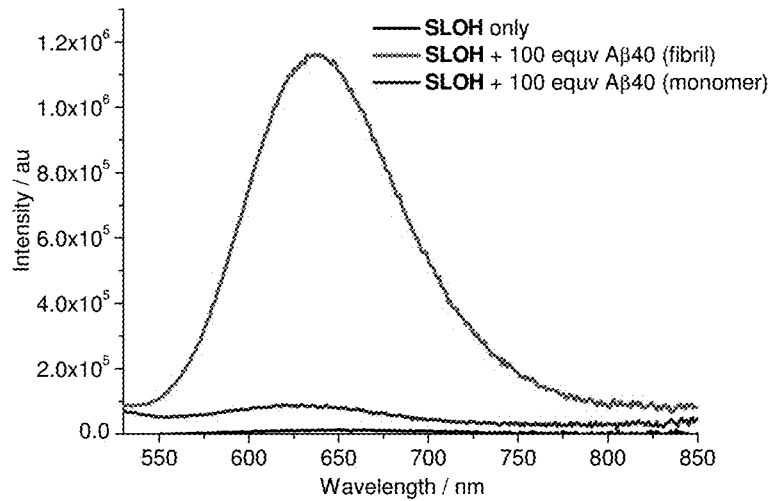
FIG. 1H shows the fluorescence spectra of SLOH on its own and in the presence of two different forms of $A\beta_{40}$.
Figure 1I:
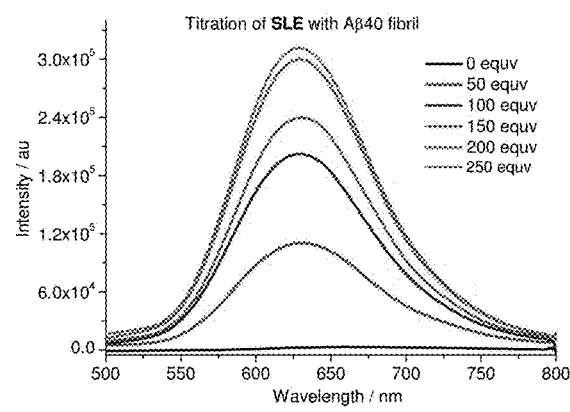
FIG. 1I shows the fluorescence spectra of SLE in various concentrations of Aβ(1-40) fibrils.
Figure 1J:
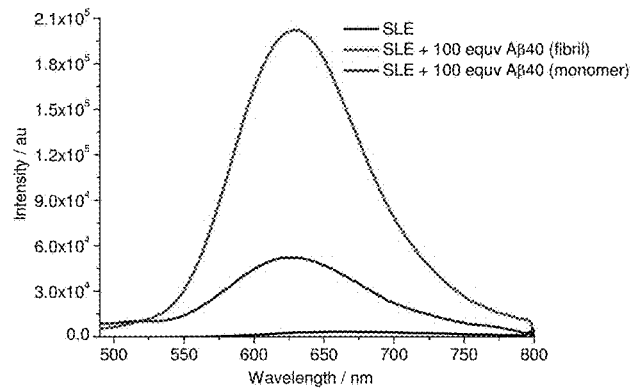
FIG. 1J shows the fluorescence spectra of SLE on its own and in the presence of two different forms of $A\beta_{40}$.
Figure 1K:
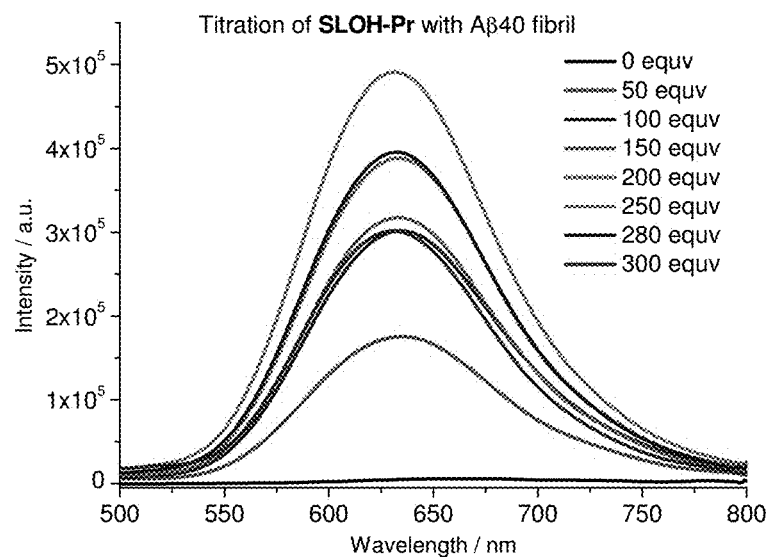
FIG. 1K shows the fluorescence spectra of SLOH-Pr in various concentrations of Aβ(1-40) fibrils.
Figure 1L:
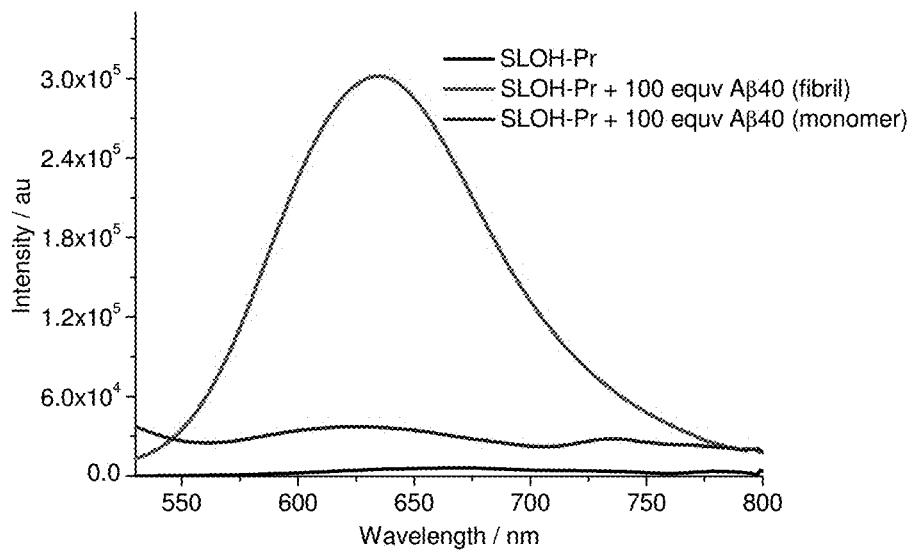
FIG. 1L shows the fluorescence spectra of SLOH-Pr on its own and in the presence of two different forms of $A\beta_{40}$.
Figure 1M:
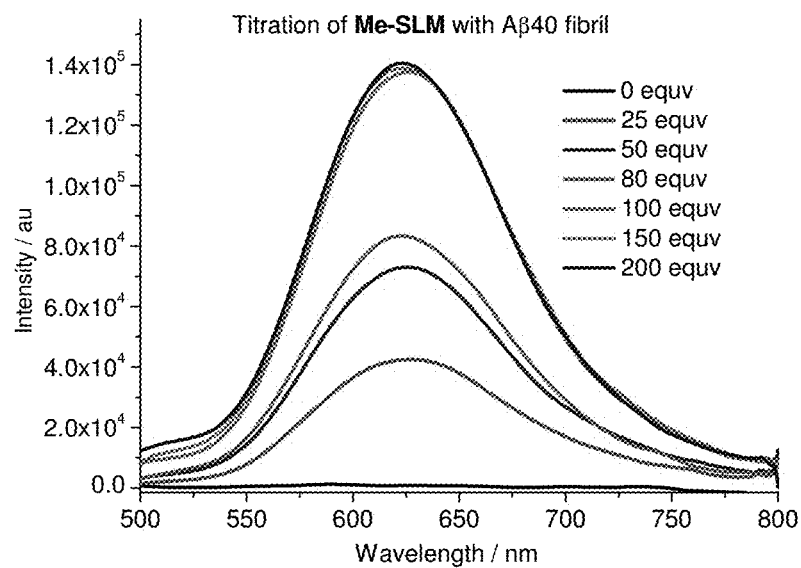
FIG. 1M shows the fluorescence spectra of Me-SLM in various concentrations of Aβ(1-40) fibrils.
Figure 1N:
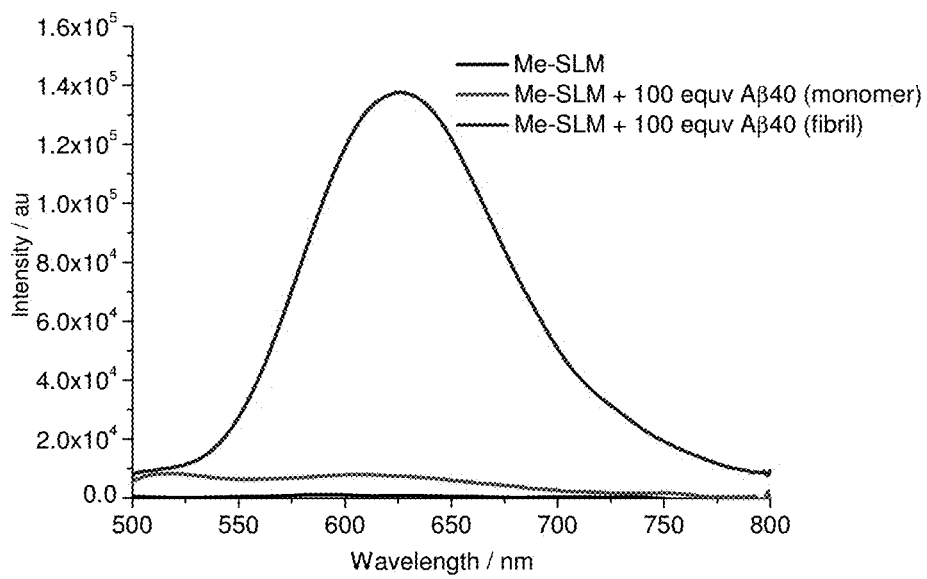
FIG. 1N shows the fluorescence spectra of Me-SLM on its own and in the presence of two different forms of $A\beta_{40}$.
Figure 1O:
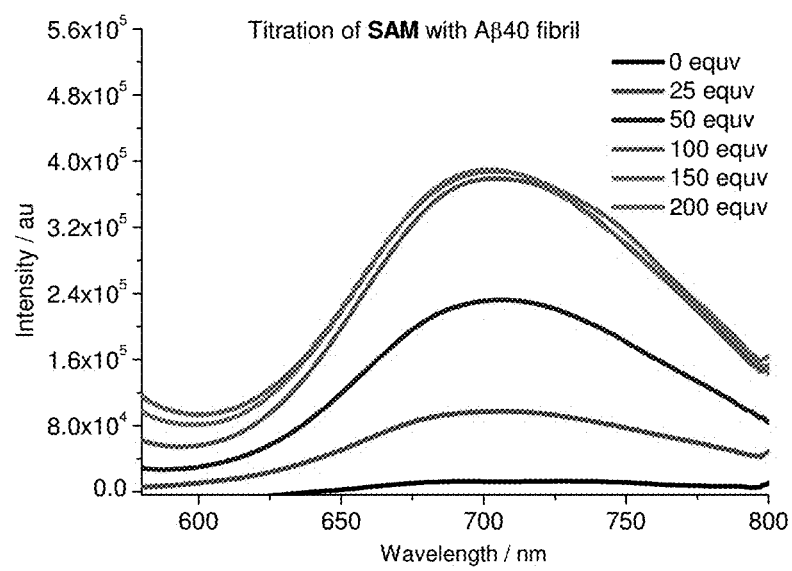
FIG. 1O shows the fluorescence spectra of SAM in various concentrations of Aβ(1-40) fibrils.
Figure 1P:
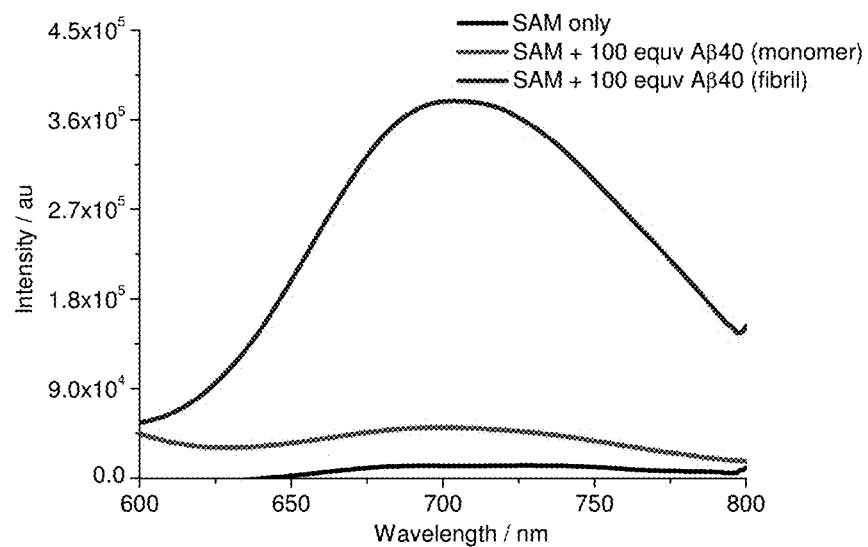
FIG. 1P shows the fluorescence spectra of SAM on its own and in the presence of two different forms of $A\beta_{40}$.
Figure 1Q:
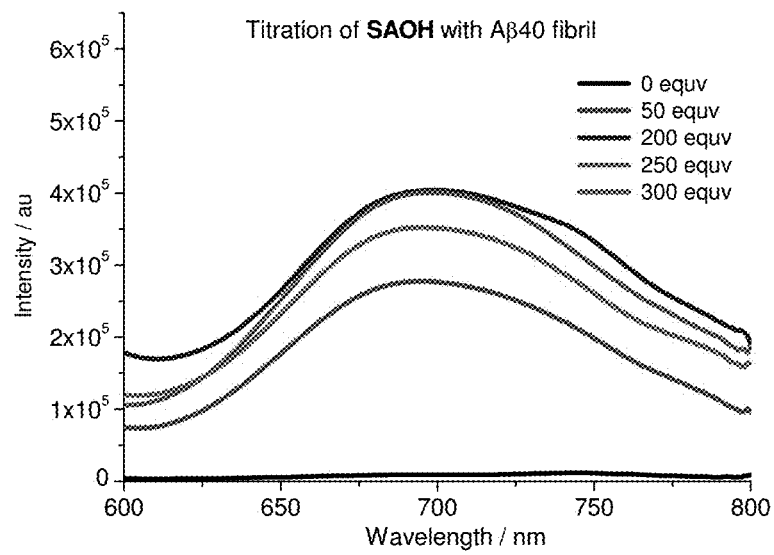
FIG. 1Q shows the fluorescence spectra of SAOH in various concentrations of Aβ(1-40) fibrils. Fluorescence spectra of SPM, SPOH, SLM, SLOH, SLE, SLOH-Pr, Me-SLM, SAM, and SAOH (1 µM) in phosphate buffer itself, in the presence of 100 equv of $A\beta_{40}$ in monomeric form, and in the presence of 100 equv of $A\beta_{40}$ in fibril state in phosphate buffer (right column) are shown.
Figure 1R:
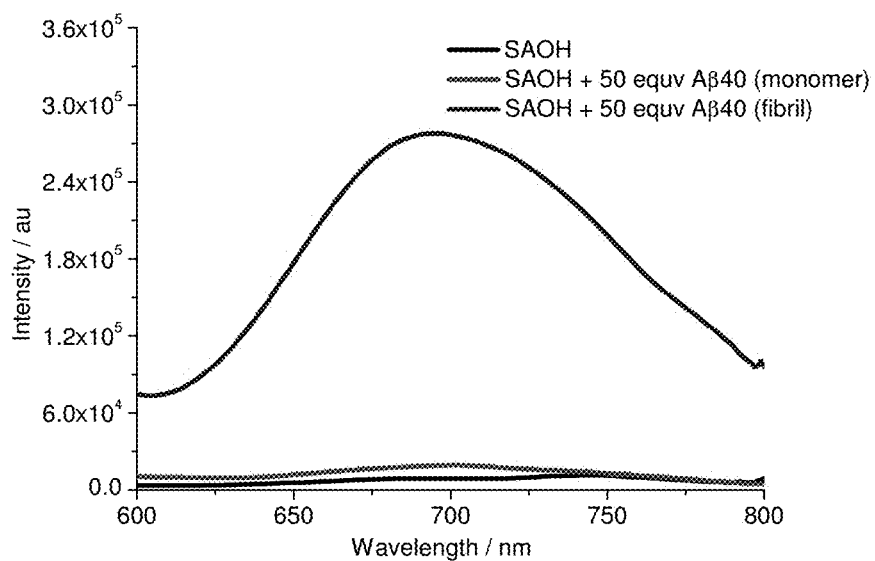
FIG. 1R shows the fluorescence spectra of SAOH on its own and in the presence of two different forms of $A\beta_{40}$.
Figure 2A:
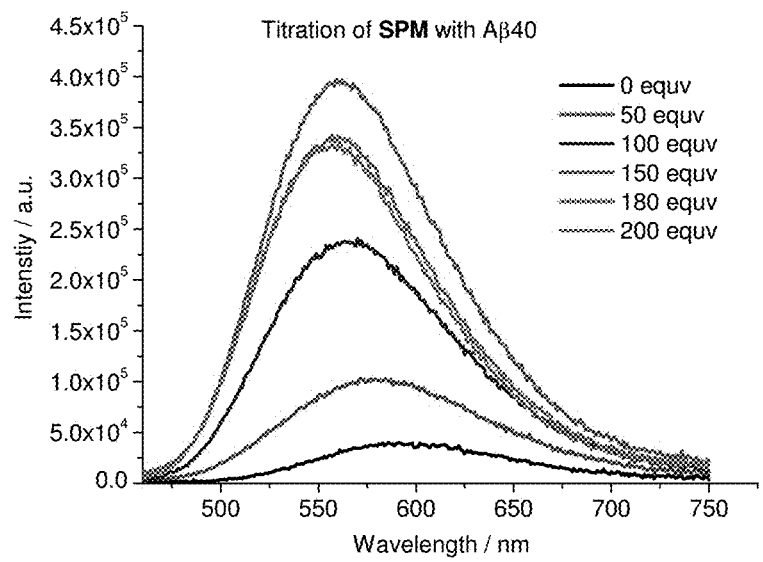
FIG. 2A shows the fluorescence spectra of SPM in various concentrations of Aβ(1-40).
Figure 2B:
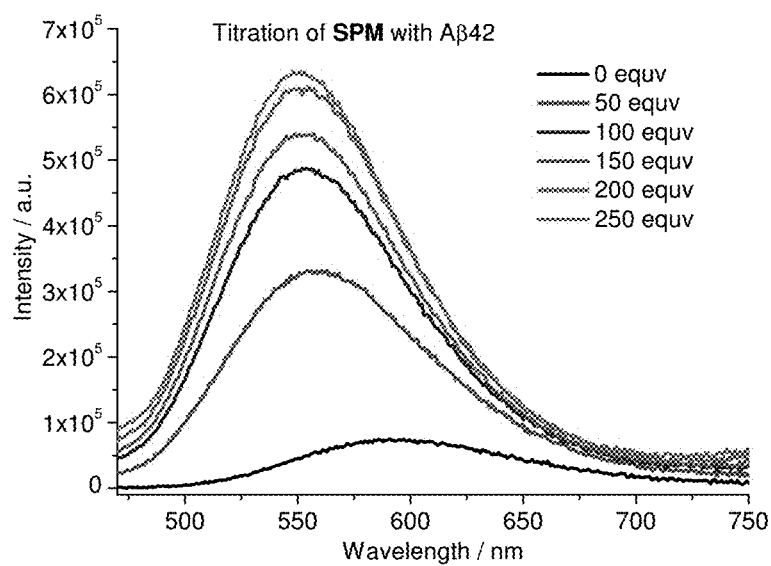
FIG. 2B shows the fluorescence spectra of SPM in various concentrations of Aβ(1-42).
Figure 2C:
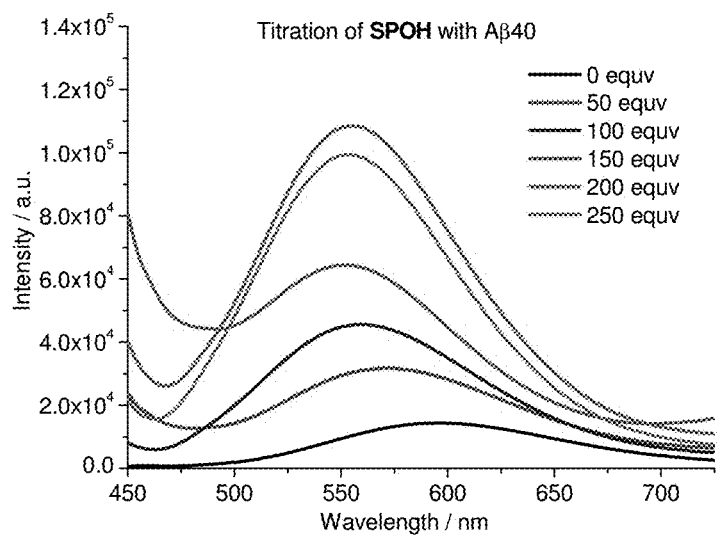
FIG. 2C shows the fluorescence spectra of SPOH in various concentrations of Aβ(1-40).
Figure 2D:
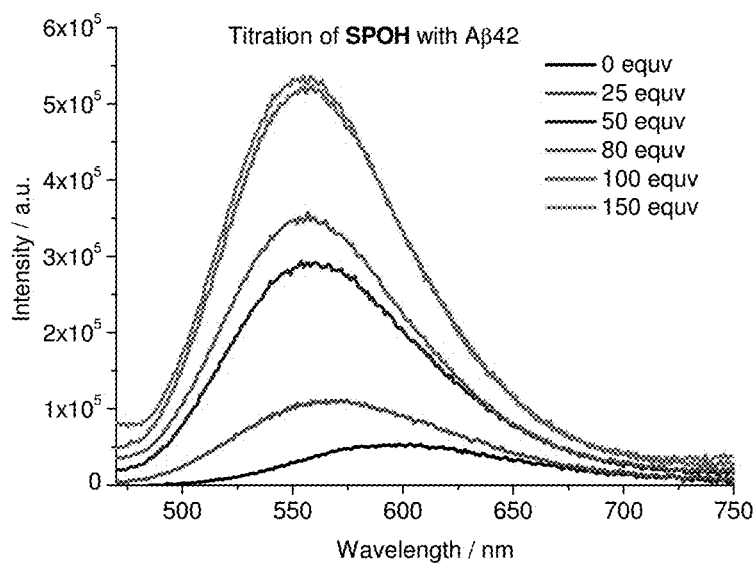
FIG. 2D shows the fluorescence spectra of SPOH in various concentrations of Aβ(1-42).
Figure 2E:
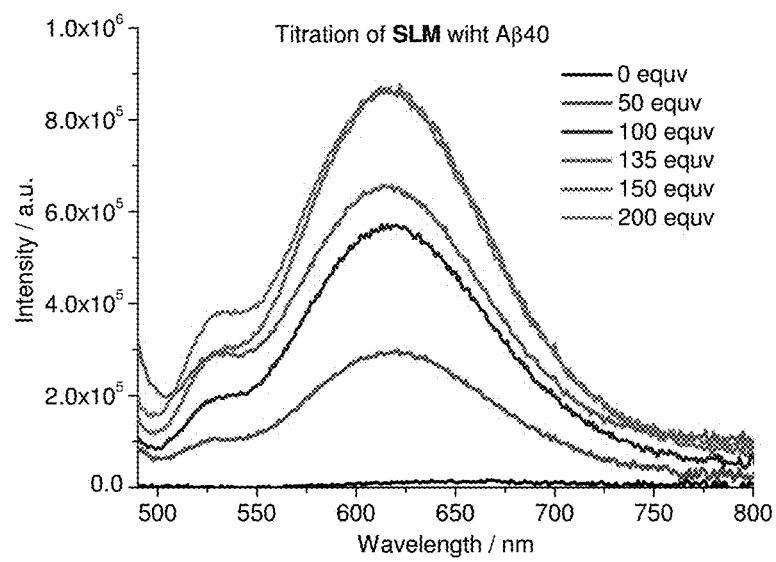
FIG. 2E shows the fluorescence spectra of SLM in various concentrations of Aβ(1-40).
Figure 2F:
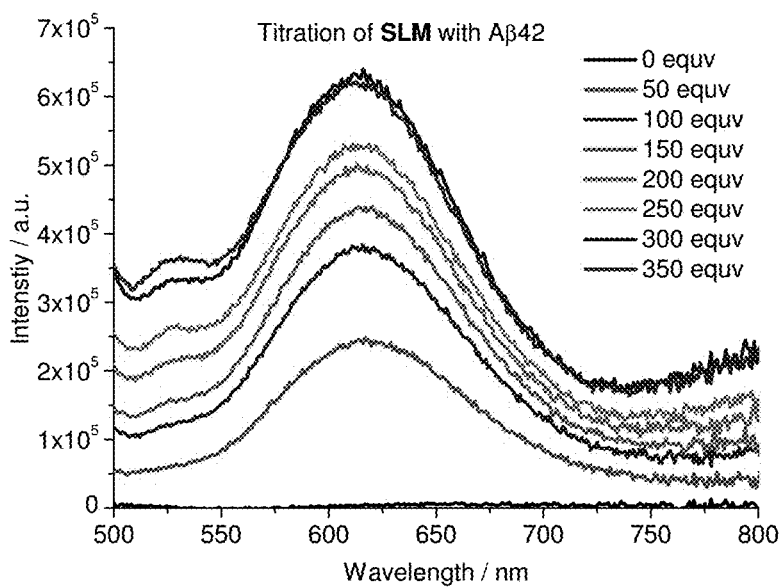
FIG. 2F shows the fluorescence spectra of SLM in various concentrations of Aβ(1-42).
Figure 2G:
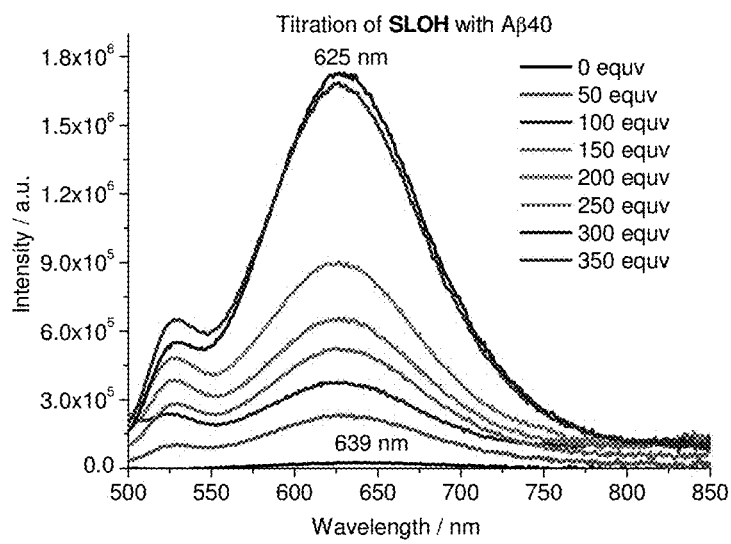
FIG. 2G shows the fluorescence spectra of SLOH in various concentrations of Aβ(1-40).
Figure 2H:
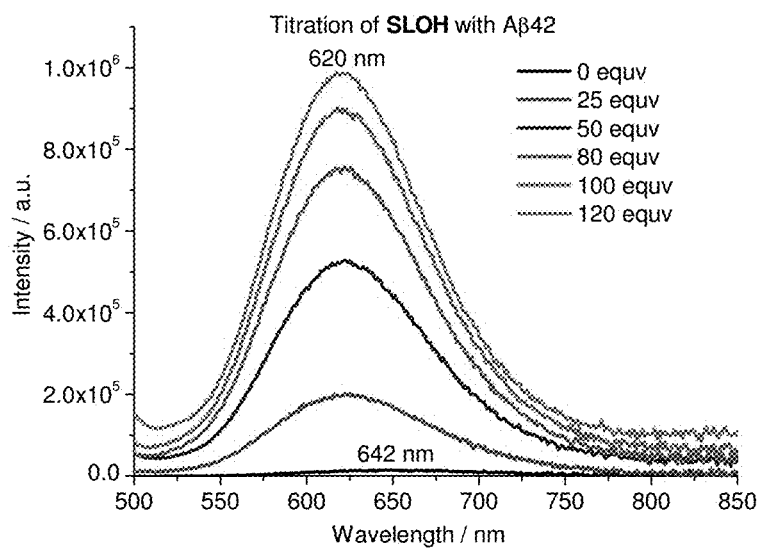
FIG. 2H shows the fluorescence spectra of SLOH in various concentrations of Aβ(1-42).
Figure 3A:
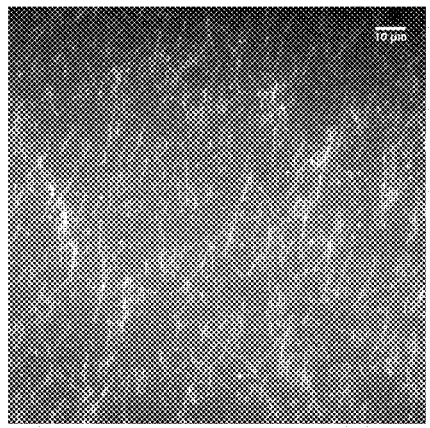
FIG. 3A shows TIRFM images of Aβ fibrils after incubation with the carbazole-based fluorophores, SPM excited at 445 nm.
Figure 3B:
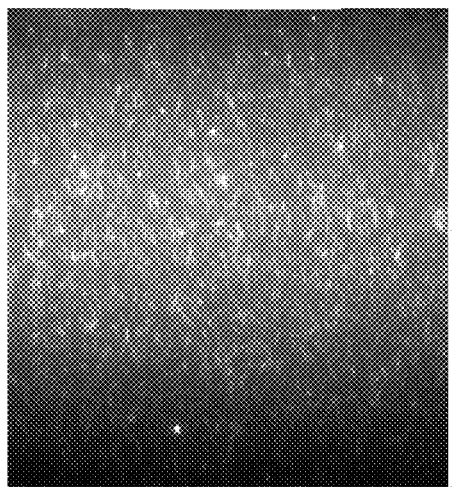
FIG. 3B shows TIRFM image of Aβ fibrils after incubation with the carbazole-based fluorophores, SLM excited at 488 nm.
Figure 3C:
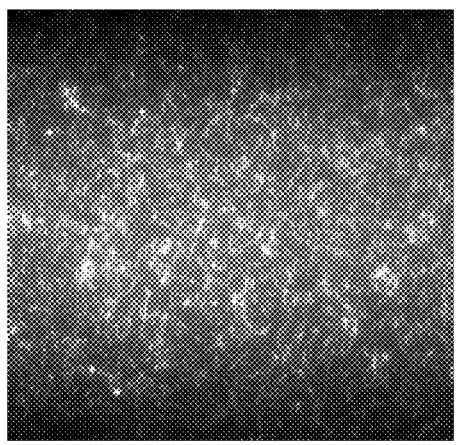
FIG. 3C shows TIRFM image of Aβ fibrils after incubation with the carbazole-based fluorophores, SLOH excited at 488 nm.
Figure 4A:
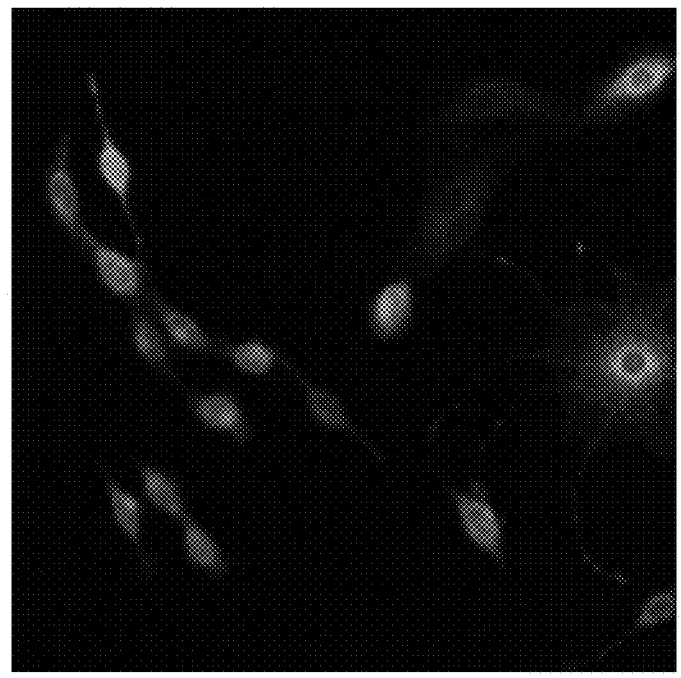
FIG. 4A shows in vitro fluorescence imaging of neuronal cells by using the carbazole-based fluorophore, SLOH.
Figure 4B:
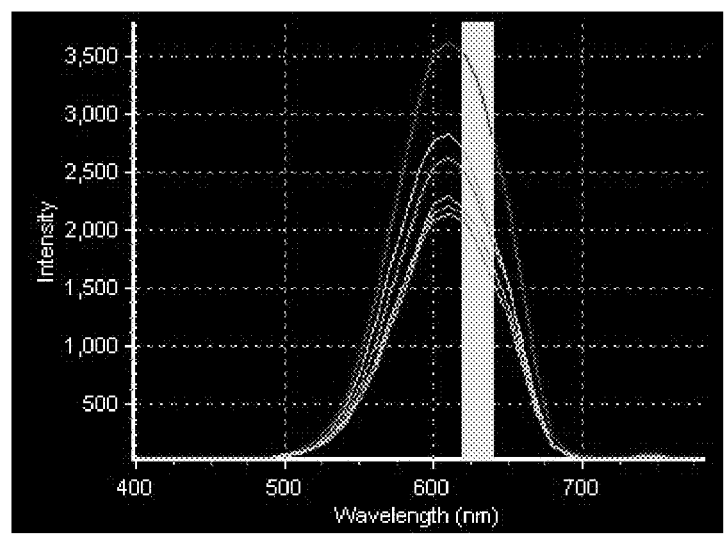
FIG. 4B shows the lambda scans of the images match well with the fluorescence spectrum of the SLOH.
Figure 5A:
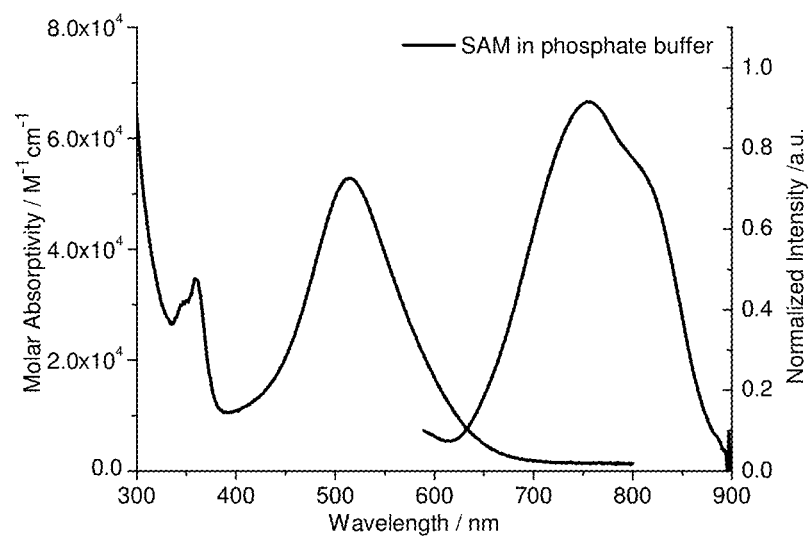
FIG. 5A shows absorption and fluorescence spectra of the carbazole-based fluorophores, SAM in phosphate buffer solution
Figure 5B:
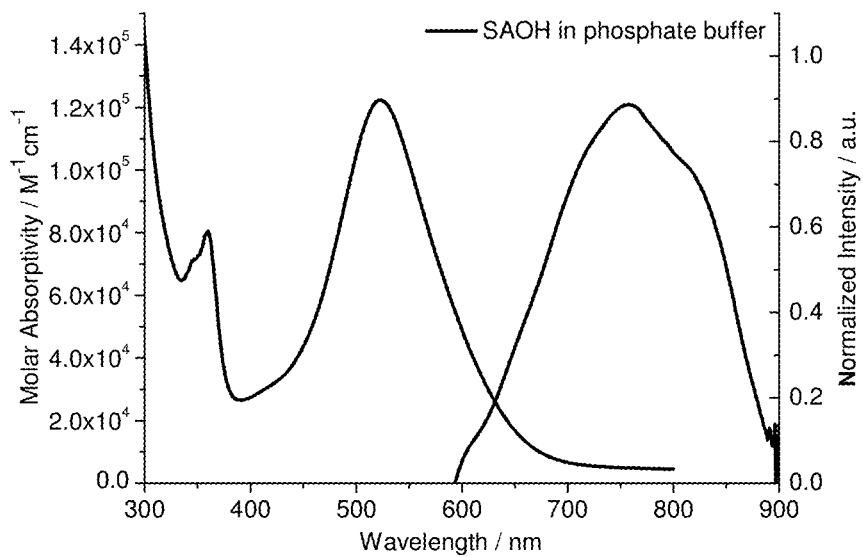
FIG. 5B shows absorption and fluorescence spectra of the carbazole-based fluorophores, SAOH in phosphate buffer solution.
Figure 6A:
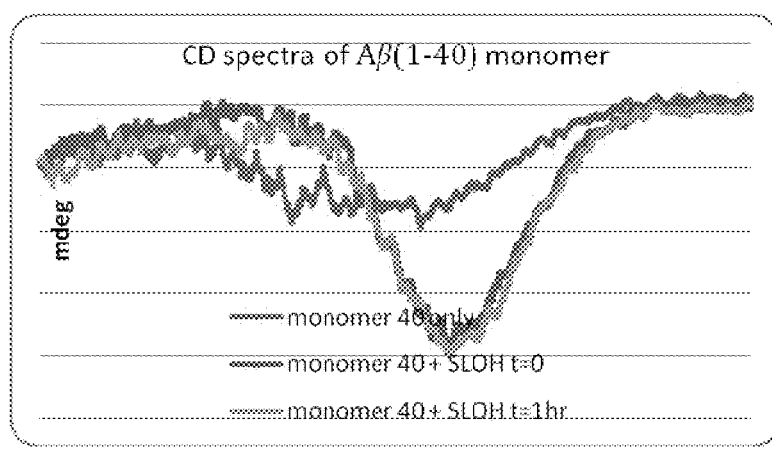
FIG. 6A shows CD spectra of Aβ(1-40) peptide in the absence and presence of SLOH (1:1) (20 µM)
Figure 6B:
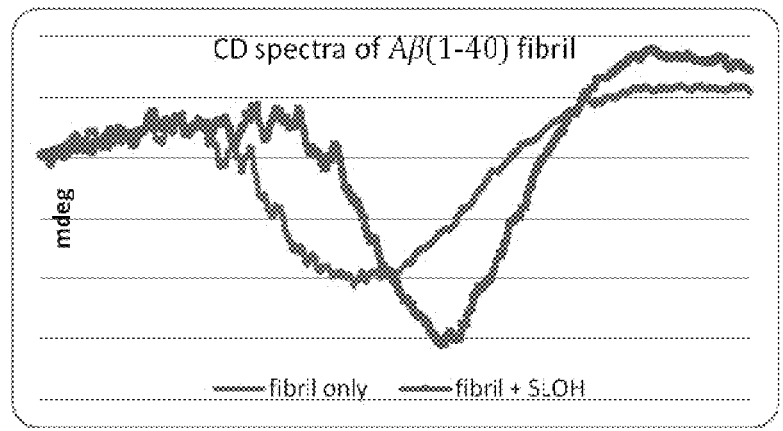
FIG. 6B shows CD spectra of fibrils in the absence and presence of SLOH (1:1) (20 µM).

A novel series of water-soluble carbazole-based fluorophores has been designed and developed. These molecules were found to bind to Aβ(1-40) and Aβ(1-42) peptides and, more specifically, their oligomers, and fibrils with strong fluorescence enhancement, therefore allowing direct imaging and detection for the Aβ peptides, oligomers and their fibrils (FIG. 1A-1R). Upon binding with Aβ peptides, there is about 8- to about 82-fold increase in fluorescence intensity concomitant with the substantial blue shifts (Δλ=14-22 nm) in the emission spectra of the fluorophores (FIG. 2A-2H). Interestingly, the fluorescence enhancement is much stronger for fibrils than peptides. (e.g. $F_{fibril}/F_{SLOH}$=81.5 vs. $F_{peptide}/F_{SLOH}$=6.3). Because of such strong increase in fluorescence, the signal-to-noise ratio is so high that imaging of single fibrils is possible. (FIG. 3A-3C) Compared to common commercial labeling dyes for Aβ such as Thioflavin-T and Congo Red, the carbazole-based fluorophores of the present invention provide an advantage of a wide range of excitation and emission tuning in visible to infra-red region (FIG. 4A-4B). Some of these molecules, e.g., SAM and SAOH, even emit at ~0.760 nm (FIG. 5A-5B), which can potentially be used for near infra-red fluorescence imaging. In addition to fluorescence titration, the binding of Aβ peptide and fibril with the carbazole-based fluorophores of the present invention were further confirmed by circular dichroism spectroscopy (FIG. 6A-6B), and electrospray ionization-mass spectrometry (ESI-MS). Total Internal Reflection Fluorescence Microscope (TIRFM) technique developed by us was used to investigate the inhibition effects of these functional fluorophores on Aβ fibril formation (FIG. 7A-7F). Remarkably, some of these molecules, e.g., SLOH, SLE, SLOH-Pr, Me-SLM, SAM, and SAOH, were found to inhibit Aβ peptide aggregation and prevent fibril growth (FIG. 7A-7F). Such inhibitory effect was further confirmed by Transmission Electron Microscopy (TEM) study (FIG. 8A-8B).

Figure 9A:
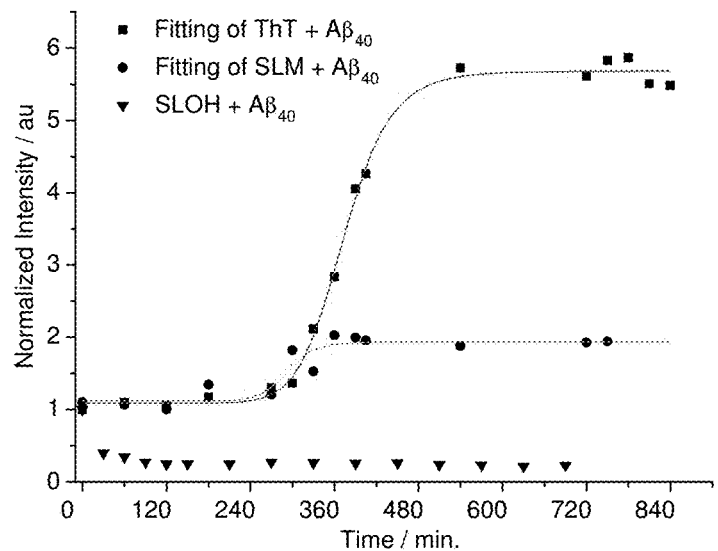
FIG. 9A shows ThT, SLM and SLOH fluorescence binding assays for 50 µM $A\beta_{40}$ fibrillation.
Figure 9B:
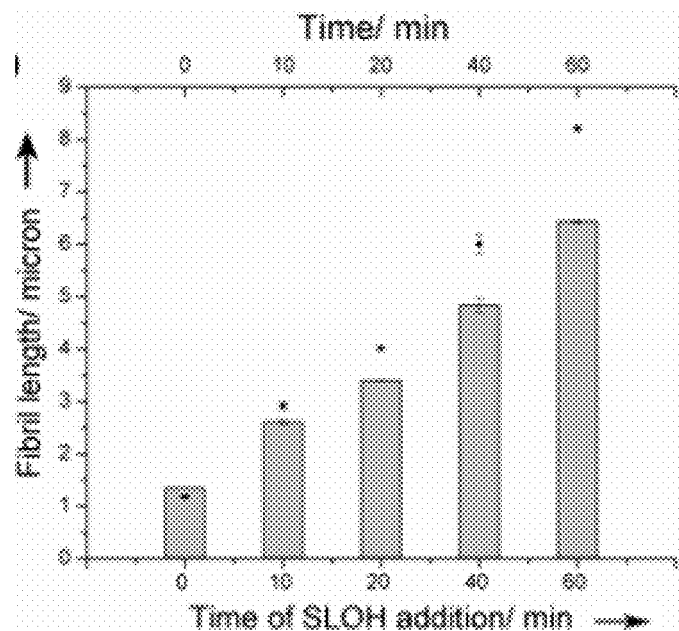
FIG. 9B shows an average length of 1 h incubated Aβ40-fibril measured from TIRFM images after 1 h seed-mediated incubation of Aβ40 monomer with (bottom axis, bars) and without (top axis, scatter point) SLOH (50 μM) added at different time points (0, 10, 20, 40 and 60 min) within an one hour-incubation.

The inhibitory effect of the carbazole-based fluorophores of the present invention on Aβ fibril growth was further investigated by measuring the (average) length of the Aβ fibrils formed after incubation of the Aβ monomers for 60 min with additions of SLOH at different time points during this period (FIG. 9A-9B). Parallel experiments conducted without any addition of SLOH were used as controls. FIG. 9A-9B shows that an addition of SLOH to the Aβ monomer strongly arrests its fibril growth. These results clearly indicate that the inhibitory effect of these carbazole-based fluorophores on Aβ aggregation is instantaneous.

To ascertain its potential clinical application, the cytotoxicities of these carbazole-based molecules, SLOH, SLOH-Pr, Me-SLM, and SAOH towards the neuronal cell, i.e., SH-SY5Y cell line, were investigated by MTT [3-(4,5-dimethylthiazol-2-yl)-2,5-diphenyltetrazolium bromide] reduction assay. The results obtained (FIG. 10A-10D) showed that these molecules were essentially non-toxic (≤20%) to the neuronal cell particularly at low dosage.

Since it is the Aβ oligomers and fibrils that are neurotoxic, further experiments with these carbazole-based molecules conducted in the presence of the Aβ monomer (non-toxic), the neurotoxic Aβ oligomers and fibrils showed that the neuronal cells became protected from the neurotoxic effects of the Aβ oligomers and fibrils when incubated with carbazole-based molecules SLOH and SAOH for 2 and 6 hours (FIG. 11A-11D).

However, in order for the observed neuroprotective effect to be clinically useful, these molecules need to be able to pass through the blood-brain barrier. The ability of these molecules to penetrate the blood-brain barrier was demonstrated in transgenic mice (FIG. 12A-12F). In addition, FIGS. 12D-F shows the selectivity of SLOH towards Aβ plaques as confirmed with Aβ antibody which was used to identify the Aβ plaques in transgenic mice's brain.

In summary, carbazole-based fluorophores of the present invention have been shown to bind to $Aβ_{(1-40)}$ and $Aβ_{(1-42)}$ as well as Aβ aggregates with dramatic fluorescence enhancement, thus allowing their direct imaging and labeling as well as the use of TIRFM technique to study the effects of these molecules on Aβ aggregation/fibrillation. Some embodiments of the carbazole-based fluorophores, for instance, SLOH and SAOH, have been shown to be a potent inhibitor of Aβ aggregation, non-toxic and exhibiting a protective effect against the neurotoxic activities of the Aβ oligomers and fibrils towards neuronal cells. These properties, together with the ability to cross the blood-brain barrier and target the Aβ plaques, render the fluorophores of the present invention a potential neuroprotective and, perhaps, therapeutic agent for Alzheimer's disease.

The following compositions according to the invention were prepared and exemplified as shown in FIG. 13. By adapting the convergent approach established previously, the Knoevenagel reaction of carbazolyl-3-aldehyde and the corresponding 4-methylpyridium or 4-methylquinolinium halide was used as the key step to synthesize various carbazole-based cyanines. Alkylation of carbazole with ethylene glycol chloride and methyl iodide in the presence of NaH in DMF gave alkylated carbazole 1a and 1b respectively. Monobromination of 1a and 1b in the presence of NBS gave alkylated 3-bromocarbazole, 2a and 2b, respectively. Formylation of 2a and 2b via lithiation bromide exchange at low temperature followed by the subsequent quenching with DMF afforded carbazolyl-3-aldehyde, 3a and 3b, respectively, in moderate yield. Alkylation of lepidine or picoline was carried out in methanol or acetonitrile affording the corresponding halide, 4-9 in good to high yield. The Knoevenagel reaction of aldehyde 3a or 3b and the corresponding 4-methylpyridium or 4-methylquinolinium halide in the presence of piperidine in ethanol afforded the corresponding carbazole-based cyanines in a moderate yield. For the acridine-based cyanines dyes, 9-methylacridine was first brominated with NBS affording brominated product 10, which gave phosphonate ester 11 by refluxing with triethyl phosphite. Condensation of phosphonate 11 and aldehyde 3a in the presence of NaH afforded 12, which was alkylated with methyl iodide and 2-iodoethanol to give SAM and SAOH, respectively. All the cyanines were fully characterized with spectroscopic techniques and found to be in good agreement with its structure.

All the solvents were dried by the standard methods wherever needed. $^1$H NMR spectra were recorded using a Bruker-400 NMR spectrometer and referenced to the residue CHCl$_3$ 7.26 ppm or DMSO-d$_6$ 2.5 ppm. $^{13}$C NMR spectra were recorded using a Bruker-400 NMR spectrometer and referenced to the CDCl$_3$ 77 ppm or DMSO-d$_6$ 39.5 ppm. Mass Spectroscopy (MS) measurements were carried out by using fast atom bombardment on the API ASTER Pulser I Hybrid Mass Spectrometer or matrix-assisted laser desorption ionization-time-of-flight (MALDI-TOF) technique. Elemental analysis was carried on the CARLO ERBA 1106 Elemental Analyzer. Compound 8 and SPM were synthesized according to previous procedure.

Although the cause and progression of AD are not well understood yet, early detection and diagnosis allows preventive and delaying measures for the progression to AD. Thus, the development of a powerful imaging technique with sensitivity at the molecular level for AD diagnosis is crucial to assess the disease status as well as the evaluation of effectiveness of potential AD drugs. Various imaging techniques including magnetic resonance imaging, positron emission tomography, near-infrared fluorescence imaging and multiphoton excited imaging have been explored for amyloid plaques imaging. All these techniques require a functional probe that can selectively target the Aβ species.

Apart from the use in direct imaging or labeling of Aβ aggregates, the carbazole-based fluorophores of the present invention is also useful as a magnetic resonance imaging (MRI) contrast agent that bind beta amyloid peptides. By conjugating appropriate paramagnetic metal complexes to these carbazole-based fluorophores, these compounds can potentially be developed into beta-amyloid peptide-specific MRI contrast agents. To convert these Aβ fibril-specific carbazole-based fluorophores dyes into MRI contrast agents, we can attach strongly paramagnetic and kinetically inert metal complexes, such as the gadolinium(III), iron(III), and manganese(II) complexes, via the R$_1$ side chain of the carbazole moiety to these fluorophores. Gd(III)-based chelates, such as [Gd(DTPA)(H$_2$O)]$^{2-}$ (DTPA=diethylenetriaminepentaacetic acid), approved for clinical use in 1988 and commercially known as Magnevist, are attractive candidates. Recently, further enhancement of the MRI contrast properties of these Gd(III) complexes was achieved by allowing the coordination of a second inner-sphere water molecule, which raised the relaxivity of the conventional Gd(III) contrast agents from 4-5 mM$^{-1}$ s$^{-1}$ (at 20 MHz field strength) to 10.5 mM$^{-1}$ s$^{-1}$, in the Gd-TREN-1-Me-3,2-HOPO complex, [1] (where TREN=tris(2-aminoethyl), HOPO=hydroxypyridinone, structure shown below).

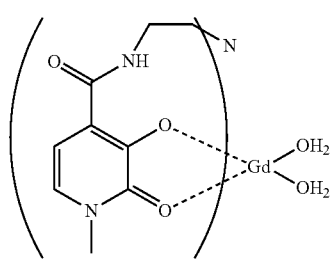

[1]

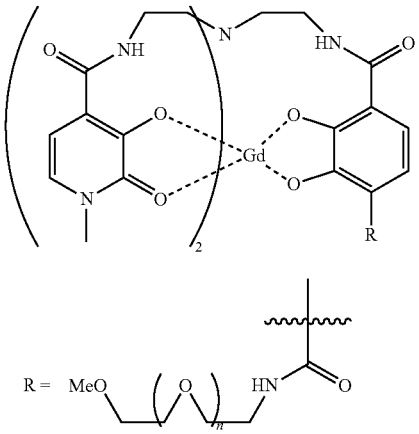

[2]

A slight modification of one of the hydroxypyridinone ligands of the Gd(III) complex, shown in [2], allows flexible attachment to the carbazole moiety of Aβ fibril-specific dyes via, for example, a polyethylene glycol (PEG) linkage.

More recently, a series of $^1$H/$^{19}$F dual MR imaging agents based on CF$_3$-labeled lanthanide(III) complexes (Ln=Gd, Tb, Dy, Ho, Er, Tm) with amide-substituted 1,4,7,10-tetraazacyclododecane ligand have been designed. An example of this ligand system bearing a CF$_3$ reporter group is shown in [3].

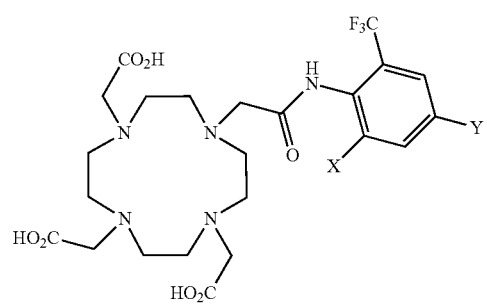

[3]

The advantage of $^{19}$F MRI is the exquisite sensitivity of the $^{19}$F shift of the reporter group to its local chemical environment, thus opening up the possibility of responsive MRI to detect changes in local pH, oxygen stress, etc. The fact that standard MRI instruments can be easily tuned from $^1$H to $^{19}$F nuclei, which have very similar magnetic properties, is an added bonus of this technique. This ligand system is also amenable to coupling (e.g., at the —X or —Y positions indicated) to the carbazole moiety of the carbazole-based fluorophores dyes.

SYNTHESIS EXAMPLES 9-(2-(2-methoxyethoxy)ethyl)-9H-carbazole (1a)

To a solution of carbazole (3.34 g, 20 mmol) in DMF (80 mL) at 0° C. was added NaH (0.72 g, 30 mmol). After heating to 80° C. for 1.5 h, 1-chloro-2-(2-methoxyethoxy) ethane (3.31 g, 24 mmol) was added dropwise. The resulting mixture was kept at 80° C. overnight. After cooling down to 0° C., the reaction mixture was carefully quenched with water and extracted with ethyl acetate three times. The combined organic phase was washed with water and brine. Then the organic layer was dried over anhydrous sodium sulfate and the solvent was removed. The residue was purified by silica gel chromatography using petroleum ether and ethyl acetate as eluent (EA:PE=1:3) to afford alkylated carbazole 1a (4.46 g) as brown oil in 83% yield. $^1$H NMR (400 MHz, CDCl$_3$) δ 8.09 (d, J=7.6 Hz, 2H), 7.46 (m, 4H), 7.23 (m, 2H), 4.51 (t, J=6.4 Hz, 2H), 3.86 (t, J=6.4 Hz, 2H), 3.52 (m, 2H), 3.42 (m, 2H), 3.31 (s, 3H). $^{13}$C NMR (400 MHz, CDCl$_3$) δ 140.5, 125.6, 122.8, 120.2, 118.9, 108.7, 71.8, 70.7, 69.1, 59.0, 43.0. MS (FAB) m/z Calcd for C$_{17}$H$_{19}$NO$_2$ 269.1. Found 269.2 [M]$^+$.

9-methyl-9H-carbazole (1b)

To a solution of carbazole (3.34 g, 20 mmol) in DMF (80 mL) at 0° C. was added NaH (0.72 g, 30 mmol). After heating at 80° C. for 1.5 h, iodomethane (3.4 g, 24 mmol) was added dropwise. The resulting mixture was kept at 80° C. overnight. After cooling down to 0° C., the reaction mixture was carefully quenched with water and extracted with ethyl acetate three times. The combined organic phase was washed with water and brine. Then the organic layer was dried over anhydrous sodium sulfate and the solvent was removed. The residue was purified by silica gel chromatography using petroleum ether and ethyl acetate as eluent (EA:PE=1:5) to afford methylated carbazole 1b (2.78 g) as yellow oil in 77% yield. $^1$H NMR (400 MHz, CDCl$_3$) δ 8.08 (d, J=8.0 Hz, 2H), 7.46 (t, J=8.0 Hz, 2H), 7.36 (d, J=8.0 Hz, 2H), 7.22 (t, J=8.0 Hz, 2H), 3.79 (s, 3H). $^{13}$C NMR (400 MHz, CDCl$_3$) δ 140.9, 125.6, 122.7, 120.2, 118.8, 108.4, 28.9.

3-bromo-9-(2-(2-methoxyethoxy)ethyl)-9H-carbazole (2a)

To a solution of 1a (2 g, 7.4 mmol) in dichloromethane (60 mL) was added NBS (1.3 g, 7.4 mmol) portionwise in an ice-water bath. After complete addition, the solution mixture was warmed to room temperature and stirred overnight. The resulting solution was washed with water and brine. The organic phase was dried over anhydrous sodium sulfate and the solvent was removed. The residue was purified by silica gel chromatography using ethyl acetate and petroleum ether (EA:PE=1:5) as eluent to afford 2a (1.75 g) in 68% yield as an oil that can turn into solid after standing. $^1$H NMR (400 MHz, CDCl$_3$) δ 8.16 (d, J=2.0 Hz, 1H), 8.01 (d, J=8.0 Hz, 1H), 7.51 (dd, J=8.0 Hz, 2.0 Hz, 1H), 7.44 (m, 2H), 7.34 (d, J=8.4 Hz, 1H), 7.22 (m, 1H), 4.46 (t, J=6.0 Hz, 2H), 3.83 (t, J=6.0 Hz, 2H), 3.48 (m, 2H), 3.39 (m, 2H), 3.28 (s, 3H). $^{13}$C NMR (400 MHz, CDCl$_3$) δ 140.7, 139.2, 128.2, 126.3, 124.5, 122.8, 121.8, 120.4, 119.3, 111.7, 110.4, 109.0, 71.8, 70.7, 69.1, 59.0, 43.2. MS (FAB) m/z Calcd for C$_{17}$H$_{18}$BrNO$_2$ 347.0. Found 347.3 [M]$^+$.

3-bromo-9-methyl-9H-carbazole (2b)

To a solution of 1b (2.5 g, 13.8 mmol) in dichloromethane (80 mL) was added NBS (2.4 g, 13.8 mmol) portion-wise in an ice-water bath. After complete addition, the solution mixture was warmed to room temperature and stirred overnight. The resulting solution was washed with water and brine. The organic phase was dried over anhydrous sodium sulfate and the solvent was removed. The residue was purified by silica gel chromatography using ethyl acetate and petroleum ether (EA:PE=1:10) as eluent to afford 2b (2.11 g) in 59% yield. $^1$H NMR (400 MHz, CDCl$_3$) δ 8.19 (d, J=2.0 Hz, 1H), 8.03 (d, J=8.0 Hz, 1H), 7.54 (dd, J=8.8 Hz, J=2.0 Hz, 1H), 7.50 (td, J=8.0 Hz, J=1.2 Hz, 1H), 7.39 (d, J=8.0 Hz, 1H), 7.27-7.22 (m, 2H), 3.82 (s, 3H).

9-(2-(2-methoxyethoxy)ethyl)-9H-carbazole-3-carbaldehyde (3a)

To a solution of 2a (1.5 g, 4.3 mmol) in dried THF (45 mL) was added n-BuLi (3.5 mL 5.2 mmol) at −78° C. The resulting mixture was stirred at −78° C. for 1 h and then added with dried DMF (3 mL) The reaction mixture was allowed to warm to room temperature and stirred overnight before quenched with aqueous ammonia chloride solution. Water was added and extracted with ethyl acetate three times. The combined organic phase was washed with brine and dried over anhydrous sodium sulfate. After removing the solvent, the residue was purified by silica gel chromatography using ethyl acetate and petroleum ether (EA:PE=1:2) as eluent to afford 3a (0.76 g) as yellow solid in 60% yield. $^1$H NMR (400 MHz, CDCl$_3$) δ 10.07 (s, 1H), 8.58 (d, J=0.8 Hz, 1H), 8.13 (d, J=8.0 Hz, 1H), 7.98 (dd, J=8.8 Hz, 0.8 Hz, 1H), 7.51 (m, 3H), 7.30 (m, 1H), 4.53 (t, J=6.0 Hz, 2H), 3.87 (t, J=6.0 Hz, 2H), 3.49 (m, 2H), 3.38 (m, 2H), 3.26 (s, 3H). $^{13}$C NMR (400 MHz, CDCl$_3$) δ 191.8, 144.3, 141.1, 128.5, 127.1, 126.6, 123.7, 123.0, 122.9, 120.6, 120.4, 109.4, 109.3, 71.8, 70.8, 69.1, 59.0, 43.4. MS (FAB) m/z Calcd for C$_{18}$H$_{19}$NO$_3$ 297.1. Found 297.3 [M]$^+$.

9-methyl-9H-carbazole-3-carbaldehyde (3b)

To a solution of 2b (1.8 g, 6.9 mmol) in dried THF (45 mL) was added n-BuLi (3.3 mL 8.3 mmol) at −78° C. The resulting mixture was stirred at −78° C. for 1 h and then added with dried DMF (8 mL). The reaction mixture was allowed to warm to room temperature and stirred overnight before quenched with aqueous ammonia chloride solution. Water was added and extracted with ethyl acetate three times. The combined organic phase was washed with brine and dried over anhydrous sodium sulfate. After removing the solvent, the residue was purified by silica gel chromatography using ethyl acetate and petroleum ether (EA:PE=1:4) as eluent to afford 3b (0.86 g) in 60% yield. $^1$H NMR (400 MHz, CDCl$_3$) δ 9.58 (s, 1H), 7.79 (s, 1H), 7.49 (d, J=7.6 Hz, 1H), 7.41 (d, J=8.8 Hz, 1H), 7.09 (t, J=7.6 Hz,), 6.90 (t, J=7.6 Hz, 1H), 6.77 (d, J=8.0 Hz, 1H), 6.61 (d, J=8.4 Hz, 1H), 3.00 (s, 3H). $^{13}$C NMR (400 MHz, CDCl$_3$) δ 190.9, 143.2, 140.5, 127.4, 125.8, 122.7, 121.7, 119.6, 119.4, 108.3, 107.6, 28.0.

1,4-dimethylquinolinium iodide (4)

A solution mixture of lepidine (0.66 g, 4.65 mmol) and iodomethane (1.32 g, 9.3 mmol) in methanol (30 mL) was heated to reflux in a sealed tube overnight. After cooling to room temperature, methanol was removed under vacuum. Anhydrous acetone was added to the residue and filtered. The resulting solid was washed with acetone and dried to afford iodide 4 (1.1 g) as yellow solid in 83% yield. $^1$H NMR (400 MHz, DMSO-d$_6$) δ 9.35 (d, J=6 Hz, 1H), 8.54 (d, J=8.8 Hz, 1H), 8.49 (d, J=8.8 Hz, 1H), 8.27 (t, J=7.2 Hz, 1H), 8.07 (t, J=4.8 Hz, 1H), 8.05 (d, J=6 Hz, 1H), 4.57 (s, 3H), 3.00 (s, 3H). $^{13}$C NMR (400 MHz, DMSO-d$_6$) δ 158.1, 148.9, 137.6, 134.9, 129.6, 128.4, 126.8, 122.4, 119.5, 44.9, 19.6. MS (FAB) m/z Calcd for C$_{11}$H$_{12}$N$^+$ 158.0. Found 158.2 [M]$^+$.

1-(2-hydroxyethyl)-4-methylquinolinium chloride (5)

A solution mixture of lepidine (0.8 g, 5.6 mmol) and 2-chloroethanol (2.25 g, 28 mmol) in acetonitrile (15 mL) was heated to 120° C. in a sealed tube overnight. After cooling to room temperature, the solvent was removed. The resulting mixture was precipitate from methanol and ethyl acetate to give the desired product 5 (0.79 g) in 63% yield. $^1$H NMR (400 MHz, DMSO-d$_6$) δ 9.24 (d, J=6 Hz, 1H), 8.61 (d, J=7.2 Hz, 1H), 8.55 (d, J=7.2 Hz, 1H), 8.25 (m, 1H), 8.06 (m, 2H), 5.15 (br, 1H), 5.08 (t, J=4.8 Hz, 2H), 3.91 (t, J=4.8 Hz, 2H), 3.01 (s, 3H). $^{13}$C NMR (400 MHz, DMSO-d$_6$) δ 158.8, 149.2, 137.1, 135.1, 129.7, 129.1, 127.2, 122.4, 119.5, 59.4, 59.0, 19.9. MS (FAB) m/z Calcd for $C_{12}H_{14}NO^+$ 188.2. Found 188.2 [M]$^+$.

1-ethyl-4-methylquinolinium bromide (6)

A solution mixture of lepidine (0.5 g, 3.5 mmol) and bromoethane (1.96 g, 18 mmol) in acetonitrile (15 mL) was heated to reflux overnight. After cooling to room temperature, the solvent was removed. The resulting mixture was precipitate from methanol and ethyl acetate to give the desired product 6 (0.81 g) in 92% yield. $^1$H NMR (400 MHz, DMSO-d$_6$) δ 9.44 (d, J=6 Hz, 1H), 8.60 (d, J=9.2 Hz, 1H), 8.54 (dd, J=8.4 Hz, J=1.2 Hz, 1H), 8.26 (td, J=8.0 Hz, J=1.6 Hz, 1H), 8.09-8.04 (m, 2H), 5.06 (tr, J=7.2 Hz, 2H), 3.00 (s, 3H), 1.58 (t, J=7.2 Hz, 3H). $^{13}$C NMR (400 MHz, DMSO-d$_6$) δ 158.4, 148.2, 136.6, 135.1, 129.6, 128.9, 127.2, 122.8, 119.2, 52.5, 19.7, 15.2.

1-(3-hydroxypropyl)-4-methylquinolinium bromide (7)

A solution mixture of lepidine (0.5 g, 3.5 mmol) and 3-bromopropanol (1.9 g, 14 mmol) in acetonitrile (15 mL) was heated to reflux overnight. After cooling to room temperature, the solvent was removed. The resulting mixture was precipitate from methanol and ethyl acetate to give the desired product 7 (0.83 g) in 84% yield. $^1$H NMR (400 MHz, DMSO-d$_6$) δ 9.41 (d, J=6 Hz, 1H), 8.58 (d, J=8.8 Hz, 1H), 8.54 (dd, J=8.8 Hz, J=1.2 Hz, 1H), 8.26 (td, J=8.0 Hz, J=1.2 Hz, 1H), 8.08-8.03 (m, 2H), 5.09 (t, J=6.8 Hz, 2H), 3.52 (t, J=5.6 Hz, 2H), 3.01 (s, 3H), 2.15-2.08 (m, 2H). $^{13}$C NMR (400 MHz, DMSO-d$_6$) δ 158.5, 148.8, 136.8, 135.1, 129.5, 128.9, 127.2, 122.6, 119.3, 57.4, 54.8, 32.0, 19.7.

1-(2-hydroxyethyl)-4-methylpyridinium chloride (9)

A solution mixture of picoline (0.93 g, 10 mmol) and 2-chloroethanol (4.03 g, 50 mmol) in acetonitrile (20 mL) was heated to 120° C. in a sealed tube overnight. After cooling to room temperature, the solvent was removed under vacuum. The resulting mixture was precipitate from methanol and ethyl acetate to give the desired product 9 (1.5 g) in 87% yield. $^1$H NMR (400 MHz, DMSO-d$_6$) δ 8.94 (d, J=6.4 Hz, 2H), 7.98 (d, J=6.4 Hz, 2H), 5.55 (br, 1H), 4.64 (t, J=4.8 Hz, 2H), 3.81 (t, J=4.8 Hz, 2H), 2.60 (s, 3H). $^{13}$C NMR (400 MHz, DMSO-d$_6$) δ 158.7, 144.2, 127.9, 62.1, 60.0, 21.4.

(E)-1-(2-hydroxyethyl)-4-(2-(9-(2-(2-methoxyethoxy)ethyl)-9H-carbazol-3-yl)vinyl)pyridinium chloride (SPOH)

A solution mixture of 3a (0.13 g, 0.75 mmol), 9 (0.27 g, 0.9 mmol) and piperidine (0.1 mL) in ethanol (30 mL) was heated to reflux overnight. After cooling down to room temperature, the organic solvent was removed by rotary evaporation. The residue was purified by recrystallization from methanol affording SPOH (0.18 g) as pale red solid in 53% yield. $^1$H NMR (400 MHz, DMSO-d$_6$) δ 8.88 (d, J=6.8 Hz, 2H), 8.55 (s, 1H), 8.19 (m, 4H), 7.84 (d, J=8 Hz, 1H), 7.65 (m, 2H), 7.49 (m, 2H), 7.25 (t, J=7.2 Hz, 1H), 5.66 (s, 1H), 4.57 (m, 4H), 3.79 (m, 4H), 3.43 (m, 2H), 3.27 (m, 2H), 3.08 (s, 3H). $^{13}$C NMR (400 MHz, DMSO-d$_6$) δ 153.4, 144.4, 142.4, 141.7, 140.8, 126.4, 126.3, 126.2, 122.7, 122.6, 122.1, 121.1, 120.3, 120.0, 119.7, 110.4, 110.2, 71.2, 69.8, 68.8, 61.6, 600.1, 58.1, 42.8. HRMS (MALDI-TOF) m/z Calcd for $C_{26}H_{29}N_2O_3$ 417.2172. Found 417.2184 [M$^+$].

(E)-4-(2-(9-(2-(2-methoxyethoxy)ethyl)-9H-carbazol-3-yl)vinyl)-1-methylquinolinium iodide (SLM)

A solution mixture of 3a (0.14 g, 0.5 mmol), 4 (0.18 g, 0.6 mmol) and piperidine (0.1 mL) in ethanol (40 mL) was heated to reflux overnight. After cooling down to room temperature, the organic solvent was removed. The residue was purified by recrystallization from methanol to afford SLM (0.24 g) as red solid in 56% yield. $^1$H NMR (400 MHz, DMSO-d$_6$) δ 9.28 (d, J=6.4 Hz, 1H), 9.14 (d, J=8.4 Hz, 1H), 8.86 (s, 1H), 8.51 (d, J=6.4 Hz, 1H), 8.42 (m, 3H), 8.28 (m, 2H), 8.13 (d, J=8.8 Hz, 1H), 8.08 (t, J=7.2 Hz, 1H), 7.80 (d, J=8.8 Hz, 1H), 7.71 (d, J=8.0 Hz, 1H), 7.53 (t, J=8.0 Hz, 1H), 7.32 (t, J=7.2 Hz, 1H), 4.64 (t, J=5.2 Hz, 2H), 4.52 (s, 3H), 3.84 (t, J=5.2 Hz, 2H), 3.48 (m, 2H), 3.33 (m, 2H), 3.11 (s, 3H). $^{13}$C NMR (400 MHz, DMSO-d$_6$) δ 153.0, 147., 144.9, 142.1, 140.9, 138.8, 134.9, 129.0, 127.3, 126.7, 126.4, 126.1, 122.8, 122.2, 121.7, 120.4, 119.9, 119.3, 116.2, 115.1, 110.5, 110.4, 71.3, 69.8, 68.9, 58.1, 44.2, 42.9. HRMS (MALDI-TOF) m/z Calcd for $C_{29}H_{29}N_2O_2$ 437.2223. Found 437.2207 [M$^+$].

(E)-1-(2-hydroxyethyl)-4-(2-(9-(2-(2-methoxyethoxy)ethyl)-9H-carbazol-3-yl)vinyl)-quinolinium chloride (SLOH)

A solution mixture of 3a (0.12 g, 0.55 mmol), 5 (0.2 g, 0.66 mmol) and piperidine (0.1 mL) in ethanol (35 mL) was heated to reflux overnight. After cooling down to room temperature, the organic solvent was removed. The residue was purified by recrystallization from methanol to afford SLOH (0.17 g) as red solid in 62% yield. $^1$H NMR (400 MHz, DMSO-d$_6$) δ 9.20 (d, J=6.4 Hz, 1H), 9.15 (d, J=8.8 Hz, 1H), 8.87 (s, 1H), 8.56 (d, J=9.2 Hz, 1H), 8.52 (d, J=6.4 Hz, 1H), 8.40 (m, 2H), 8.24 (m, 2H), 8.13 (d, J=8.8 Hz, 1H), 8.05 (t, J=7.6 Hz, 1H), 7.78 (d, J=8.8 Hz, 1H), 7.71 (d, J=8.4 Hz, 1H), 7.52 (t, J=8.0 Hz, 1H), 7.31 (t, J=7.6 Hz, 1H), 5.27 (t, J=5.6 Hz, 1H), 5.05 (t, J=4.8 Hz, 2H), 4.64 (t, J=4.8 Hz, 2H), 3.94 (m, 2H), 3.84 (t, J=5.2 Hz, 2H), 3.47 (m, 2H), 3.31 (m, 2H), 3.11 (s, 3H). $^{13}$C NMR (400 MHz, DMSO-d$_6$) δ 153.3, 147.8, 145.0, 142.1, 140.9, 138.1, 134.7, 128.7, 127.1, 126.8, 126.7, 126.5, 122.8, 122.2, 121.7, 120.3, 119.8, 119.2, 116.3, 114.8, 110.4, 110.3, 71.2, 69.8, 68.8, 58.9, 58.5, 58.0, 42.9. HRMS (MALDI-TOF) m/z Calcd for $C_{30}H_{31}N_2O_3$ 467.2342. Found 467.2340 [M$^+$]. Calcd for $C_{30}H_{31}ClN_2O_3$: C, 71.53; H, 6.21; N, 5.57. Found: C, 71.04; H, 6.23; N, 5.36.

(E)-1-ethyl-4-(2-(9-(2-(2-methoxyethoxy)ethyl)-9H-carbazol-3-yl)vinyl)quinolinium bromide (SLE)

A solution mixture of 6 (0.20 g, 0.8 mmol), 3a (0.33 g, 1.1 mmol) and piperidine (0.1 mL) in ethanol (40 mL) was heated to reflux overnight. After cooling down to room temperature, the organic solvent was removed. The residue was purified by precipitation from methanol and ethyl acetate to afford SLE (0.22 g) in 53% yield. $^1$H NMR (400 MHz, DMSO-d$_6$) δ 9.34 (d, J=8.4 Hz, 1H), 9.15 (d, J=8.4 Hz, 1H), 8.86 (s, 1H), 8.54-8.51 (m, 2H), 8.44 (d, J=16 Hz, 1H), 8.36 (d, J=16 Hz, 1H), 8.28-8.23 (m, 2H), 8.12 (d, J=8.0 Hz, 1H), 8.05 (t, J=7.6 Hz, 1H), 7.77 (d, J=8.4 Hz, 1H), 7.70 (d, J=8.4 Hz, 1H), 7.52 (t, J=7.6 Hz, 1H), 7.31 (t, J=7.6 Hz, 1H), 4.99 (tr, J=6.8 Hz, 2H), 4.63 (t, J=4.8 Hz, 2H), 3.84 (t, J=4.8 Hz, 2H), 3.48 (t, J=4.8 Hz, 2H), 3.31 (t, J=4.8 Hz, 2H), 3.11 (s, 3H), 1.59 (t, J=6.8 Hz, 3H). $^{13}$C NMR (400 MHz, DMSO-$d_6$) δ 153.2, 146.7, 145.1, 142.2, 140.9, 137.7, 135.0, 128.9, 127.4, 126.8, 126.7, 126.5, 126.4, 122.8, 122.2, 121.8, 120.4, 119.9, 119.0, 116.2, 115.5, 110.4, 110.3, 71.3, 69.8, 68.9, 58.1, 51.9, 15.1. HRMS (MALDI-TOF) m/z Calcd for $C_{30}H_{31}N_2O_2$ 451.2380. Found 451.2362 [M]$^+$.

(E)-1-(3-hydroxypropyl)-4-(2-(9-(2-(2-methoxy-ethoxy)ethyl)-9H-carbazol-3-yl)vinyl)-quinolinium bromide (SLOH-Pr)

A solution mixture of 7 (0.17 g, 0.6 mmol), 3a (0.24 g, 0.8 mmol) and piperidine (0.1 mL) in ethanol (40 mL) was heated to reflux overnight. After cooling down to room temperature, the organic solvent was removed. The residue was purified by precipitation from methanol and ethyl acetate to afford SLOH-Pr (0.14 g) in 41% yield. $^1$H NMR (400 MHz, DMSO-$d_6$) δ 9.29 (d, J=6.8 Hz, 1H), 9.15 (d, J=8.4 Hz, 1H), 8.88 (s, 1H), 8.51 (d, J=6.8 Hz, 1H), 8.45 (d, J=16 Hz, 1H), 8.37 (d, J=16 Hz, 1H), 8.28-8.24 (m, 2H), 8.13 (d, J=8.4 Hz, 1H), 8.05 (t, J=8.0 Hz, 1H), 7.77 (d, J=8.8 Hz, 1H), 7.70 (d, J=8.4 Hz, 1H), 7.52 (t, J=7.6 Hz, 1H), 7.31 (t, J=7.2 Hz, 1H), 5.01 (t, J=7.2 Hz, 2H), 4.86 (t, J=5.2 Hz, 1H), 4.63 (t, J=4.8 Hz, 2H), 3.84 (t, J=5.2 Hz, 2H), 3.55 (tr, J=5.2 Hz, 2H), 3.47 (t, J=5.6 Hz, 2H), 3.31 (t, J=4.8 Hz, 2H), 3.11 (s, 3H), 2.13 (t, J=6.0 Hz, 2H). $^{13}$C NMR (400 MHz, DMSO-$d_6$) δ 153.3, 147.3, 145.1, 142.2, 140.9, 137.9, 135.0, 128.8, 127.4, 126.8, 126.7, 126.5, 126.4, 122.8, 122.2, 121.8, 120.4, 119.9, 119.0, 116.3, 115.2, 110.5, 110.4, 71.3, 69.8, 68.9, 58.1, 57.6, 54.2, 42.9, 32.0. HRMS (MALDI-TOF) m/z Calcd for $C_{31}H_{33}N_2O_3$ 481.2485. Found 481.2458 [M]$^+$.

(E)-1-methyl-4-(2-(9-methyl-9H-carbazol-3-yl)vi-nyl)quinolinium iodide (Me-SLM)

A solution mixture of 1,4-dimethylquinolinium iodide (0.14 g, 0.5 mmol), 3b (0.13 g, 0.6 mmol) and piperidine (0.1 mL) in ethanol (40 mL) was heated to reflux overnight. After cooling down to room temperature, the organic solvent was removed. The residue was purified by precipitation from methanol and ethyl acetate to afford Me-SLM (0.14 g) in 62% yield. $^1$H NMR (400 MHz, DMSO-$d_6$) δ 9.27 (d, J=6.4 Hz, 1H), 9.12 (d, J=8.4 Hz, 1H), 8.86 (s, 1H), 8.49 (d, J=6.4 Hz, 1H), 8.45-8.23 (m, 5H), 8.15 (d, J=8.8 Hz, 1H), 8.06 (t, J=7.6 Hz, 1H), 7.75 (d, J=8.4 Hz, 1H), 7.66 (d, J=8.0 Hz, 1H), 7.55 (t, J=7.6 Hz, 1H), 7.32 (t, J=7.6 Hz, 1H), 4.51 (s, 3H), 3.95 (s, 3H). $^{13}$C NMR (400 MHz, DMSO-$d_6$) δ 152.9, 147.3, 144.8, 142.2, 141.2, 138.7, 134.8, 128.8, 127.4, 126.6, 126.4, 126.3, 126.0, 122.6, 122.0, 121.8, 120.4, 119.7, 119.1, 116.0, 115.0, 109.8, 109.7, 44.3, 29.3. HRMS (MALDI-TOF) m/z Calcd for $C_{25}H_{21}N_2$ 349.1699. Found 349.1694 [M]$^+$.

9-(bromomethyl)acridine (10)

To a solution of 9-methylacridine (1.93 g, 10 mmol) in dichloromethane (100 mL) was added NBS (1.78 g, 10 mmol) portion-wise in an ice-water bath. After complete addition, the solution mixture was warmed to room temperature and stirred overnight. The resulting solution was washed with water and brine. The organic phase was dried over anhydrous sodium sulfate and the solvent was removed. The residue was purified by silica gel chromatography using ethyl acetate and petroleum ether (EA:PE=1:5) as eluent to afford 10 (2.08 g) in 77% yield. $^1$H NMR (400 MHz, CDCl$_3$) δ 8.27 (d, J=8.8 Hz, 4H), 7.81 (t, J=8.0 Hz, 2H), 7.68 (t, J=8.0 Hz, 2H), 5.42 (s, 2H). $^{13}$C NMR (400 MHz, CDCl$_3$) δ 148.9, 138.7, 130.5, 130.1, 126.8, 123.8, 123.4, 23.1. MS (FAB) m/z Calcd for $C_{14}H_{10}BrN$ 272.1. Found 2722. [M]$^+$.

Diethyl acridin-9-ylmethylphosphonate (11)

The mixture of 10 (1.5 g, 5.5 mmol) and triethyl phosphite (2 mL) was heated to reflux for 4 h. After cooling down to room temperature, the excess triethyl phosphite was removed under vacuum to afford 11 (1.7 g) in 94% yield. $^1$H NMR (400 MHz, CDCl$_3$) δ 8.23 (d, J=8.8 Hz, 2H), 8.17 (d, J=8.8 Hz, 2H), 7.72 (t, J=7.2 Hz, 2H), 7.54 (t, J=7.2 Hz, 2H), 4.13 (d, J=24 Hz, 2H), 3.92-3.77 (m, 4H), 1.04 (t, J=7.2 Hz, 6H). $^{13}$C NMR (400 MHz, CDCl$_3$) δ 148.4, 148.3, 135.8, 135.7, 129.9, 129.8, 125.8, 125.3, 125.2, 124.9, 124.8, 62.4, 27.5, 26.1, 16.1.

(E)-9-(2-(9-(2-(2-methoxyethoxy)ethyl)-9H-carba-zol-3-yl)vinyl)acridine (12)

To a solution of 3a (0.45 g, 1.5 mmol) and 11 (0.49 g, 1.5 mmol) in dry THF (45 mL), NaH (45 mg, 1.8 mmol) was added carefully in an ice-water bath. After complete addition, the solution mixture was warmed to room temperature and stirred overnight. After quenching by water, the resulting mixture was extracted with ethyl acetate for three times. The combined organic phase was washed with brine twice and dried over anhydrous sodium sulfate. After removing the solvent, the resulting crude product was purified by silica gel chromatography using DCM and petroleum ether (DCM: PE=1:10) to afford 12 (0.45 g) in 64% yield. $^1$H NMR (400 MHz, CDCl$_3$) δ 8.45 (d, J=8.8 Hz, 2H), 8.37 (s, 1H), 8.26 (d, J=8.8 Hz, 2H), 8.15 (d, J=8.0 Hz, 1H), 7.95 (d, J=8.4 Hz, 1H), 7.85 (d, J=8.8 Hz, 1H), 7.80 (t, J=8.0 Hz, 2H), 7.58-7.51 (m, 5H), 7.31-7.25 (m, 2H), 4.58 (t, J=6.4 Hz, 2H), 3.92 (t, J=6.4 Hz, 2H), 3.57-3.55 (m, 2H), 3.48-3.45 (m, 2H), 3.35 (s, 3H). $^{13}$C NMR (400 MHz, CDCl$_3$) δ 148.9, 143.8, 141.0, 140.6, 129.9, 127.9, 126.1, 125.4, 124.6, 123.4, 122.9, 120.4, 119.5, 119.2, 119.1, 109.4, 109.2, 71.9, 70.9, 69.3, 59.1, 43.3. HRMS (MALDI-TOF) m/z Calcd for $C_{32}H_{29}N_2O_2$ 473.2223. Found 473.2210 [M+H]$^+$.

(E)-9-(2-(9-(2-(2-methoxyethoxy)ethyl)-9H-carba-zol-3-yl) vinyl)-10-methylacridinium iodide (SAM)

A solution of 12 (0.20 g, 0.4 mmol) and methyl iodide (0.57 g, 4 mmol) in acetonitrile (8 mL) was heated to 100° C. in sealed tube for 24 h. After cooling down to room temperature, the solvent was removed and the resulting mixture was purified by precipitation from methanol and ethyl acetate to afford SAM (0.15 g) in 61% yield. $^1$H NMR (400 MHz, CDCl$_3$) δ 8.74 (d, J=8.0 Hz, 2H), 8.49 (s, 1H), 8.46 (d, J=8.8 Hz, 2H), 8.31 (d, J=16 Hz, 1H), 8.26 (t, J=8.0 Hz, 2H), 8.10 (d, J=8.0 Hz, 1H), 7.93 (d, J=8.0 Hz, 1H), 7.83 (t, J=7.2 Hz, 2H), 7.51 (d, J=8.4 Hz, 1H), 7.46 (t, J=6.4 Hz, 2H), 7.44 (d, J=16 Hz, 1H), 7.20 (t, J=6.4 Hz, 1H), 4.82 (s, 3H), 4.46 (t, J=6.0 Hz, 2H), 3.88 (t, J=6.0 Hz, 2H), 3.55-3.53 (m, 2H), 3.44-3.42 (m, 2H), 3.30 (s, 3H). $^{13}$C NMR (400 MHz, CDCl$_3$) δ 157.9, 149.5, 141.8, 140.5, 140.1, 137.8, 129.3, 127.4, 126.9, 126.5, 126.2, 123.9, 123.2, 122.1, 121.2, 121.1, 119.9, 117.9, 117.4, 109.4, 109.0, 71.7, 70.6, 69.0, 58.9, 43.3, 39.5. HRMS (MALDI-TOF) m/z Calcd for $C_{33}H_{31}N_2O_2^+$ 487.2380. Found 487.2387 [M]$^+$.

(E)-10-(2-hydroxyethyl)-9-(2-(9-(2-(2-methoxy-ethoxy)ethyl)-9H-carbazol-3-yl)vinyl)-acridinium iodide (SAOH)

A solution of 12 (0.2 g, 0.4 mmol) and 2-iodoethanol (0.7 g, 4 mmol) in acetonitrile (10 mL) was heated to 120° C. in sealed tube for 24 h. After cooling down to room temperature, the solvent was removed and the resulting mixture was purified by precipitation from methanol and ethyl acetate to afford SAOH (0.13 g) in 52% yield. $^1$H NMR (400 MHz, CDCl$_3$) δ 8.98 (d, J=9.2 Hz, 2H), 8.77 (d, J=8.4 Hz, 2H), 8.44 (s, 1H), 8.36 (t, J=8.0 Hz, 2H), 8.18 (d, J=8.4 Hz, 1H), 8.17 (d, J=16 Hz, 1H), 7.91 (d, J=8.0 Hz, 1H), 7.86 (t, J=8.0 Hz, 2H), 7.62 (d, J=8.8 Hz, 1H), 7.55 (d, J=8.4 Hz, 1H), 7.52 (t, J=6.4 Hz, 2H), 7.48 (d, J=16 Hz, 1H), 7.33 (t, J=6.4 Hz, 1H), 5.63 (t, J=6.0 Hz, 2H), 4.75 (t, J=7.6 Hz, 1H), 4.59 (t, J=6.0 Hz, 2H), 4.51-4.47 (m, 2H), 3.94 (t, J=6.0 Hz, 2H), 3.57-3.55 (m, 2H), 3.47-3.44 (m, 2H), 3.33 (s, 3H). $^{13}$C NMR (400 MHz, CDCl$_3$) δ 158.2, 149.1, 141.9, 140.7, 140.6, 138.1, 129.1, 126.9, 126.5, 126.4, 124.3, 123.3, 122.4, 121.2, 120.9, 120.0, 119.0, 117.0, 109.6, 109.2, 71.8, 70.6, 69.1, 59.3, 58.9, 52.2, 43.3. HRMS (MALDI-TOF) m/z Calcd for $C_{34}H_{33}N_2O_3^+$ 517.2486. Found 517.2476 [M]'.

Another general chemical structures of carbazole-based fluorophores representation, including S series are shown in FIG. 14.

In FIG. 14, Ar is a heteroaromatic ring selected from the group consisting of pyridinyl, substituted pyridinyl, quinolinyl, substituted quinolinyl, acridinyl, substituted acridinyl, benzothiazolyl, substituted benzothiazolyl, benzoxazolyl, and substituted benzoxazolyl;

R$_1$ is a radical selected from the group consisting of polyethylene glycol chain, alkyl, substituted alkyl, peptide chain, glycosidyl, and C(O)NHCH((CH$_2$CH$_2$O)$_2$CH$_3$)$_2$;

R$_2$ is selected from the group consisting of ethenyl, ethynyl, azo and azomethinyl.

R$_3$ is a radical selected from the group consisting of alkyl, HO-alkyl, HS-alkyl, H$_2$N-alkyl, HNalkyl-alkyl, alkyl-COOalkyl, alkyl-CONH$_2$, alkyl-CONHalkyl, alkyl-COOH, alkyl-COO$^-$, (alkyl)$_3$N$^+$-alkyl, and (Ph)$_3$P$^+$-alkyl, and polyethylene glycol chain;

X is an anion selected from the group consisting of F, Cl, Br, I, HSO$_4$, H$_2$PO$_4$, HCO$_3$, tosylate, and mesylate;

Y is selected from the group consisting of H, F, Cl, OH, OCH$_3$ and R$_2$—Ar—R$_3$, wherein Ar is a heteroaromatic ring selected from the group consisting of pyridinyl, substituted pyridinyl, quinolinyl, substituted quinolinyl, acridinyl, substituted acridinyl, benzothiazolyl, substituted benzothiazolyl, benzoxazolyl, and substituted benzoxazolyl; R$_2$ is selected from the group consisting of ethenyl, ethynyl, azo and azomethinyl; R$_3$ is a radical selected from the group consisting of alkyl, HO-alkyl, HS-alkyl, H$_2$N-alkyl, HNalkyl-alkyl, alkyl-COOalkyl, alkyl-CONH$_2$, alkyl-CONHalkyl, alkyl-COOH, alkyl-COO$^-$, (alkyl)$_3$N$^+$-alkyl, and (Ph)$_3$P$^+$-alkyl, and polyethylene glycol chain.

A novel series of water-soluble carbazole-based fluorophores has been designed and developed. These molecules were found to bind to Aβ(1-40) and Aβ(1-42) peptides and, more importantly, their oligomers, and fibrils with strong fluorescence enhancement, therefore allowing direct imaging and detection for the Aβ peptides, oligomers and their fibrils. (FIG. 16) Upon binding with Aβ peptides, there is an increase in fluorescence intensity up to 160-fold enhancement concomitant with the substantial blue shifts in the emission spectra of the fluorophores. Remarkably, these molecules, including F-SLOH, SLAD, SLAce, and SLG were found to inhibit Aβpeptide aggregation and prevent fibril growth. In one embodiment of the present invention, Ar is a quinolinyl or substituted quinolinyl; R$_1$ is a 2-(2-methoxyethoxy)ethoxy; R$_2$ is an ethenyl; R$_3$ is a 2-hydroxyethyl or acetamide or acetate or 2-(2-methoxyethoxy)ethoxy; X is a chloride or iodide and Y is a H or F which are represented by the formula "F-SLOH", "SLAD", "SLAce", and "SLG", respectively, as shown in FIG. 15.

Total Internal Reflection Fluorescence Microscope (TIRFM) technique developed was used to investigate the inhibition effects of these functional fluorophores on Aβ (1-40) fibril formation (FIG. 17). Remarkably, some of these molecules, e.g., F-SLOH, SLAD, SLAce, and SLG were found to inhibit Aβ (1-40) peptide aggregation and prevent fibril growth (FIG. 17).

To confirm its clinical application, the cytotoxicities of these carbazole-based molecules towards the neuronal cell, i.e., SH-SY5Y cell line, are investigated by MTT [3-(4,5-dimethylthiazol-2-yl)-2,5-diphenyltetrazolium bromide] reduction assay. The results obtained (FIG. 18A-18C) show that these molecules are essentially non-toxic (20%) to the neuronal cell. The cytotoxicity of these molecules are low with $LC_{50}$=5-90 μM.

There is growing evidence showing that the soluble Aβ oligomers is the most neurotoxic form, further experiments with these carbazole-based molecules conducted in the presence of the Aβ monomer, Aβ oligomers and fibrils show that the primary cortical cells are protected from the neurotoxic effects of the Aβ species when incubated with the cyanine dyes, F-SLOH, and SLAD (FIG. 19A-19B). The reactive oxygen species (ROS) induced by the Aβ toxicity causes much damage in AD. Remarkably, F-SLOH, and SLAD reduce the ROS induced by the Aβ species in primary cortical cells.

However, in order for the observed neuroprotective effect to be clinically useful, these molecules need to be able to pass through the blood-brain barrier. The ability of these molecules to penetrate the blood-brain barrier was demonstrated in mice (FIG. 20A-20F). The binding of these molecules toward Aβ plaques in the brains of the Alzheimer's disease animal models are also demonstrated. Impressively, F-SLOH, SLAD, SLAce, and SLG show blood-brain permeability.

Further Synthesis Experiments (E)-1-(2-(2-methoxyethoxy)ethyl)-4-(2-(9-(2-(2-methoxyethoxy)ethyl)-9H-carbazol-3-yl)vinyl)quinolinium iodide (SLG)

A solution mixture of 1 (0.30 g, 0.8 mmol), 9-(2-(2-methoxyethoxy)ethyl)-9H-carbazole-3-carbaldehyde (0.33 g, 1.1 mmol) and piperidine (0.1 mL) in ethanol (40 mL) was heated to reflux overnight. After cooling down to room temperature, the organic solvent was removed. The residue was purified by precipitation from methanol and ethyl acetate to afford SLG (0.25 g) in 48% yield. $^1$H NMR (400 MHz, DMSO-d$_6$) δ 9.18 (d, J=6.8 Hz, 1H), 9.14 (d, J=8.0 Hz, 1H), 8.87 (s, 1H), 8.55 (d, J=8.8 Hz, 1H), 8.51 (d, J=6.8 Hz, 1H), 8.45 (d, J=16 Hz, 1H), 8.36 (d, J=16 Hz, 1H), 8.24 (d, J=7.2 Hz, 2H), 8.13 (d, J=7.6 Hz, 1H), 8.05 (t, J=7.6 Hz, 1H), 7.77 (d, J=8.4 Hz, 1H), 7.69 (d, J=8.0 Hz, 1H), 7.52 (t, J=7.2 Hz, 1H), 7.31 (t, J=7.2 Hz, 1H), 5.15 (t, J=5.2 Hz, 2H), 4.63 (t, J=4.8 Hz, 2H), 3.97 (t, J=5.2 Hz, 2H), 3.84 (t, J=4.8 Hz, 2H), 3.53 (t, J=4.8 Hz, 2H), 3.48 (t, J=4.8 Hz, 2H), 3.32-3.29 (m, 4H), 3.11 (s, 3H), 3.06 (s, 3H). $^{13}$C NMR (100 MHz, DMSO-d$_6$) δ 153.5, 147.7, 145.3, 142.2, 140.9, 138.1, 134.8, 128.8, 127.4, 126.7, 126.4, 122.8, 122.2, 121.8, 120.4, 119.8, 119.2, 116.2, 114.8, 110.4, 110.3, 71.2, 71.1, 69.8, 69.6, 68.8, 67.8, 58.1, 58.0, 55.9, 42.9. HRMS (MALDI-TOF) m/z Calcd for $C_{33}H_{37}N_2O_4$ 525.2747. Found 525.2747 [M]$^+$.

3-Fluoro-9-(2-(2-methoxyethoxy)ethyl)-9H-carbazole (5)

To a solution of 3-bromo-9-(2-(2-methoxyethoxy)ethyl)-9H-carbazole (3.23 g, 9.3 mmol) in dry THF (50 ml) was added n-BuLi (1.6 M, 8.7 ml, 13.9 mmol) at −78° C. The resulting mixture was stirred for 50 min at −78° C. and then added with N-fluorobenzenesulfonimide (5.6 g, 18.6 mmol).

The reaction mixture was allowed to warm to rt and stirred for 2 h before quenched with ammonia chloride solution. The organic layer was separated, dried over anhydrous sodium sulfate and evaporated under vacuum. The residue was purified by silica gel column chromatography eluting with 3:1 petroleum ether/ethyl acetate to give compound 5 in 75% yield. $^1$H NMR (400 MHz, CDCl$_3$) δ 8.03 (d, J=7.6 Hz, 1H), 7.73 (dd, J=2.4 Hz, J=8.8 Hz 1H), 7.50-7.44 (m, 2H), 7.39 (dd, J=4.4 Hz, J=8.8 Hz, 1H), 7.25-7.17 (m, 2H), 4.49 (t, J=6.4 Hz, 2H), 3.86 (t, J=6.4 Hz, 2H), 3.52-3.50 (m, 2H), 3.43-3.41 (m, 2H), 3.32 (s, 3H). $^{13}$C NMR (100 MHz, CDCl$_3$) δ 158.6, 156.2, 141.4, 137.1, 126.3, 123.4, 123.3, 122.6, 122.6, 120.6, 119.1, 113.6, 113.3, 109.7, 109.6, 109.2, 106.1, 105.9, 72.1, 71.0, 69.4, 59.2, 43.4. HRMS (MALDI-TOF) m/z Calcd for C$_{17}$H$_{18}$FNO$_2$ 287.1316. Found 287.1314[M]$^+$.

3-Bromo-6-fluoro-9-(2-(2-methoxyethoxy)ethyl)-9H-carbazole (6)

To a solution of 3-fluoro-9-(2-(2-methoxyethoxy)ethyl)-9H-carbazole (1.06 g, 3.71 mmol) in chloroform (20 ml) was added NBS (0.66 g, 3.71 mmol) batch-wise in an ice-water bath. After complete addition, the reaction mixture was allowed to warm to room temperature slowly and stirred overnight. The reaction mixture was washed with water and brine. The organic layer was dried over anhydrous sodium sulfate and evaporated under reduced pressure to give compound 6 in 84% yield. $^1$H NMR (400 MHz, CDCl$_3$) δ 8.09-8.06 (m, 1H), 7.63-7.60 (m, 1H), 7.52-7.50 (m, 1H), 7.36-7.26 (m, 2H), 7.21-7.16 (m, 1H), 4.40 (d, J=5.6 Hz, 2H), 3.82-3.80 (m, 2H), 3.49-3.46 (m, 2H), 3.40-3.38 (m, 2H), 3.29 (s, 3H). $^{13}$C NMR (100 MHz, CDCl$_3$) δ 158.7, 156.3, 140.1, 137.4, 128.9, 124.2, 124.2, 123.2, 122.3, 122.2, 114.4, 114.1, 111.8, 110.8, 110.0, 109.9, 106.2, 106.0. HRMS (MALDI-TOF) m/z Calcd for C$_{17}$H$_{17}$BrFNO$_2$ 366.0499. Found 366.0502[M]$^+$.

6-Bromo-9-(2-(2-methoxyethoxy)ethyl)-9H-carbazole-3-carbaldehyde (7)

To a solution of 3-bromo-6-fluoro-9-(2-(2-methoxyethoxy)ethyl)-9H-carbazole (3.4 g, 9.3 mmol) in dry THF (50 ml) was added n-BuLi (1.6 M, 8.7 ml, 13.9 mmol) at −78° C. The resulting mixture was stirred for 50 min at −78° C. and then added with N-formylmorpholine (1.86 ml, 18.6 mmol). The reaction mixture was allowed to warm to rt and stirred for 2 h before quenched with ammonia chloride solution. The organic layer was separated, dried over anhydrous sodium sulfate and evaporated under vacuum. The residue was purified by silica gel column chromatography eluting with 2:1 petroleum ether/ethyl acetate to give compound 7 in 65% yield. $^1$H NMR (400 MHz, CDCl$_3$) δ 10.08 (s, 1H), 8.53 (s, 1H), 8.02-8.00 (m, 1H), 7.80-7.77 (m, 1H), 7.54 (d, J=8.8 Hz, 1H), 7.45 (dd, J=4.0 Hz, J=9.2 Hz 1H), 7.28-7.23 (m, 1H), 4.52 (t, J=5.6 Hz, 2H), 3.88 (t, J=5.6 Hz, 2H), 3.52-3.50 (m, 2H), 3.40 (d, J=2.8 Hz, 2H), 3.28 (s, 3H). $^{13}$C NMR (100 MHz, CDCl$_3$) δ 191.8, 159.3, 156.9, 145.2, 137.8, 128.8, 127.5, 124.4, 123.7, 123.7, 123.7, 122.8, 114.8, 114.5, 110.6, 110.5, 109.8, 106.7, 106.4, 72.1, 71.0, 69.5, 59.2, 43.9. HRMS (MALDI-TOF) m/z Calcd for C$_{18}$H$_{18}$FNO$_3$ 316.1343. Found 316.1340[M]$^+$.

(E)-4-(2-(6-Fluoro-9-(2-(2-methoxyethoxy)ethyl)-9H-carbazol-3-yl)vinyl)-1-(2-hydroxyethyl)quinolin-1-ium chloride (F-SLOH)

A solution mixture of 2 (0.21 g, 1.2 mmol), 6-bromo-9-(2-(2-methoxyethoxy)ethyl)-9H-carbazole-3-carbaldehyde (0.50 g, 1.6 mmol) and piperidine (0.1 ml) in methanol (40 ml) was heated to reflux overnight. After being cooled down to room temperature, the organic solvent was removed. The residue was purified by precipitation from methanol and ethyl acetate to afford F-SLOH in 65% yield. $^1$H NMR (400 MHz, DMSO-d$_6$) δ 9.22 (d, J=6.8 Hz, 1H), 9.15 (d, J=8.4 Hz, 1H), 8.91 (s, 1H), 8.58 (d, J=9.2 Hz, 1H), 8.53 (d, J=6.8 Hz, 1H), 8.40 (d, J=3.6 Hz, 1H), 8.24 (t, J=7.6 Hz 1H), 8.15-8.13 (m, 1H), 8.08-8.03 (m, 2H), 7.78 (d, J=8.8 Hz, 1H), 7.74-7.71 (m, 1H), 7.40-7.35 (m, 1H), 5.34 (s, 1H), 5.08-5.05 (m, 2H), 4.65-4.62 (m, 2H), 3.94-3.92 (m, 2H), 3.84-3.91 (m, 2H), 3.46-3.45 (m, 2H), 3.31-3.29 (m, 2H), 3.10 (s, 3H). $^{13}$C NMR (100 MHz, DMSO-d$_6$) δ 168.6, 154.3, 145.2, 143.4, 142.1, 142.0, 140.9, 126.5, 126.3, 122.9, 122.8, 122.7, 122.1, 121.4, 120.4, 119.9, 110.6, 110.3, 71.3, 69.9, 68.9, 58.1. HRMS (MALDI-TOF) m/z Calcd for C$_{30}$H$_{30}$FN$_2$O$_3$ 485.2235. Found 485.2211 [M]$^+$.

(E)-1-(2-Ethoxy-2-oxoethyl)-4-(2-(9-(2-(2-methoxyethoxy)ethyl)-9H-carbazol-3-yl)vinyl)quinolin-1-ium bromide (SLAce)

A solution of 8 (0.21 g, 0.5 mmol) and ethyl 2-bromoacetate (0.33 g, 2.0 mmol) in ethanol was stirred overnight at room temperature. After solvent removal, the residue was precipitated from methanol and ethyl acetate to afford SLAce (0.15 g) in 52% yield. $^1$H NMR (400 MHz, DMSO-d$_6$) δ 9.24 (d, J=6.8 Hz, 1H), 9.18 (d, J=8.4 Hz, 1H), 8.89 (s, 1H), 8.61 (d, J=6.8 Hz, 1H), 8.53 (d, J=16 Hz, 1H), 8.42 (d, J=16 Hz, 1H), 8.31 (d, J=8.8 Hz, 1H), 8.26-8.23 (m, 2H), 8.15 (d, J=8.4 Hz, 1H), 8.06 (t, J=7.6 Hz, 1H), 7.80 (d, J=8.4 Hz, 1H), 7.72 (d, J=8.0 Hz, 1H), 7.53 (t, J=8.0 Hz, 1H), 7.33 (t, J=7.2 Hz, 1H), 5.99 (s, 2H), 4.64 (t, J=5.2 Hz, 2H), 4.25 (tr, J=7.2 Hz, 2H), 3.84 (t, J=5.2 Hz, 2H), 3.47 (m, 2H), 3.31 (m, 2H), 3.11 (s, 3H), 1.26 (t, J=5.2 Hz, 3H). $^{13}$C NMR (100 MHz, DMSO-d$_6$) δ 166.5, 154.6, 147.9, 146.5, 142.4, 140.9, 138.7, 128.9, 127.6, 126.7, 126.6, 126.0, 122.8, 122.2, 122.1, 120.4, 119.9, 118.9, 116.2, 115.0, 110.5, 110.4, 71.3, 69.8, 68.8, 62.3, 58.1, 56.4, 42.9, 13.9. HRMS (MALDI-TOF) m/z Calcd for C$_{32}$H$_{33}$N$_2$O$_4$ 509.2446. Found 509.2427 [M]$^+$.

(E)-1-(2-Amino-2-oxoethyl)-4-(2-(9-(2-(2-methoxyethoxy)ethyl)-9H-carbazol-3-yl)vinyl)quinolin-1-ium bromide (SLAD)

A solution of 8 (0.21 g, 0.5 mmol) and 2-bromoacetamide (0.27 g, 2.0 mmol) in acetonitrile was heated to reflux overnight. After removing the solvent, the residue was precipitated from methanol and ethyl acetate to afford SLAD (0.15 g) in 63% yield. $^1$H NMR (400 MHz, DMSO-d$_6$) δ 9.24 (d, J=6.8 Hz, 1H), 9.17 (d, J=8.4 Hz, 1H), 8.89 (s, 1H), 8.58 (d, J=6.8 Hz, 1H), 8.45 (dd, J=33.6 Hz, J=18 Hz, 2H), 8.28-8.25 (m, 2H), 8.18-8.14 (m, 3H), 8.08-8.04 (m, 1H), 7.80 (d, J=8.4 Hz, 2H), 7.72 (d, J=8.4 Hz, 1H), 7.55-7.51 (m, 1H), 7.34-7.31 (m, 1H), 5.68 (s, 2H), 4.66-4.63 (m, 2H), 3.86-3.83 (m, 2H), 3.49-3.47 (m, 2H), 3.31-3.29 (m, 2H), 3.11 (s, 3H). $^{13}$C NMR (100 MHz, DMSO-d$_6$) δ 166.3, 154.0, 148.2, 145.8, 142.3, 140.9, 138.7, 135.2, 128.8, 127.5, 126.7, 126.4, 126.1, 122.8, 122.2, 122.0, 120.4, 118.5, 116.2, 115.0, 110.5, 110.4, 71.3, 69.8, 68.8, 58.1, 57.8, 42.9. HRMS (MALDI-TOF) m/z Calcd for C$_{30}$H$_{30}$N$_3$O$_3$ 480.2281. Found 480.2301 [M]$^+$.

In summary, carbazole-based fluorophores bind to Aβ(1-40) and Aβ(1-42) as well as Aβ aggregates with strong fluorescence enhancement, thus allowing their direct imaging and labeling. TIRFM technique is used to study the effects of these molecules on Aβ aggregation/fibrillation. Some carbazole-based fluorophores, for instance, F-SLOH, and SLAD are non-toxic, potent Aβ aggregation inhibitors and exhibit a protective effect against the neurotoxic activities of the Aβ oligomers and fibrils towards neuronal cells. These properties of F-SLOH, and SLAD together with their ability to cross the blood-brain barrier and target the Aβ plaques, render their application for neuroprotective therapy and as therapeutic agent for Alzheimer's disease.

DETAILED DESCRIPTION OF THE EMBODIMENTS IN THE PRESENTLY CLAIMED INVENTION

Blood-Brain Barrier (BBB) Permeable Cyanine-Conjugated Nanoparticles for Magnetic Resonance and Fluorescence Imaging (a) Motivation for the Presently Claimed Invention Such as the Problems it Solves or Opportunities it Addresses:

Alzheimer's disease (AD) is the most common but still incurable degenerative dementia. Thus, it poses grand challenges in research worldwide in the areas of early detection, diagnostics and therapeutics. As the causes and progression of AD are not well understood yet, early detection of at-risk subjects allows preventive and delaying measures for the progression to AD. Therefore, development of early detection techniques before the onset of clinical symptoms is highly desirable and beneficial. Furthermore, the development of a powerful imaging technique with sensitivity at the molecular level for AD diagnosis is crucial to monitoring the disease's progression and understanding the complex disease processes as well as the evaluation of effectiveness of potential AD drugs.

Neuroimaging represents the most prominent evidence-based approach for the diagnosis of AD and other neurodegenerative disorders. Abnormal brain structures can be revealed using brain imaging technologies. Positron emission tomography (PET) is currently used for beta-amyloid (Aβ) plaques imaging in human brain in which a radiotracer was first approved by the FDA for imaging of cerebral Aβ plaques in 2012. However, the PET imaging suffers from low spatial resolution. Other drawbacks for the use of PET scan include high cost, limited availability, and use of radioactive imaging agent.

On the other hand, magnetic resonance imaging (MRI) offers superior spatial resolution and does not require the use of invasive radioactive tracer. Furthermore, it is widely available and accessible in the clinical setting. Nevertheless, MRI without Aβ-specific contrast agent could only afford limited sensitivity for early AD detection in which only mature and large enough senile plaques could be visualized in an AD mouse model.

(b) General Utility of the Embodiments of the Presently Claimed Invention:

In contrast to gadolinium complex MRI contrast agents, iron oxide nanoparticles have been shown to be effective at relatively low concentrations and can serve better as MRI contrast enhancement agents owing to their superparamagnetic property. Therefore, superparamagnetic iron oxide nanoparticles have recently drawn considerable attention for their diverse diagnostic applications in various biological systems. Among those, the development of non-toxic, low-cost, blood-brain barrier permeable and highly Aβ specific contrast agents for early detection and diagnosis of AD is of particularly appealing with which the successful treatment rate of new potentials in clinical trials could certainly be improved.

(c) Advantages and Disadvantages in Comparison to Current and Potential Alternatives to the Embodiments of the Presently Claimed Invention:

Such MRI contrast agents conjugated with high Aβ-specific targeting cyanine groups not only is non-toxic and non-invasive but also affords superior spatial resolution.

(d) Best Ways of Using the Presently Claimed Invention as Well as Possible Variations:

There are challenges in utilizing nanoparticles for biological applications including biocompatibility and particle agglomeration. The high surface area-to-volume ratio of the nanoparticles often leads to a high tendency of self-aggregation and interaction with plasma proteins, resulting in fast clearance by the reticuloendothelial system. Therefore, nanoparticles are often coated with a biocompatible and hydrophilic protecting material to improve their dispersity and stability.

The present inventors have successfully conjugated their proprietary carbazole-based cyanines compounds such as SLCOOH (FIG. 22A-22C and FIG. 23) synthesized according to Scheme 1A (FIG. 28), which are (i) non-toxic (as assessed by the MTT assay shown in FIG. 24) and BBB penetrable; and (ii) able to target the Aβ species in-vivo with high affinity, to the magnetic nanoparticles (MNPs) (superparamagnetic and anti-ferromagnetic) as a surface-modifying material, resulting in safe and effective non-invasive MRI contrast agents (CAs), cyanine@MNP, for cerebral Aβ species imaging. Their results also show that the functionalized cyanine@MNP CAs are not only non-toxic but also highly BBB permeable and selective to the Aβ aggregates/fibrils as demonstrated by the in vivo fluorescence imaging of transgenic mice (FIG. 25A-25D and FIG. 26A-26D).

The conjugation of the MNPs and carbazole-based cyanines can be easily carried out by a wide range of well-established chemistries and protocols including the amide formation chemistry (as shown in Scheme 2, FIG. 29), carboxylic acid derivatives chemistry, sulfhydryl chemistry, click chemistry, Schiff-base condensation, and Mannich reaction.

The SLCOOH-conjugated $SiO_2@Fe_3O_4$ nanoparticles are shown to be successfully applied for MRI imaging of a live 3-month-old APP/PS1 transgenic mouse brain. The presence of Aβ deposition is thus evidenced by the localization of the dark spots of the SLCOOH-conjugated $SiO_2@Fe_3O_4$ nanoparticles (FIG. 27A-27B).

Synthesis of (E)-1-(carboxymethyl)-4-(2-(9-(2-(2-methoxyethoxy)ethyl)-9H-carbazol-3-yl)vinyl)quinolin-1-ium bromide (SLCOOH)

According to Scheme 1A in FIG. 28, a solution of 4 (0.21 g, 0.5 mmol) and bromoacetic acid (0.28 g, 2.0 mmol) in ethanol is stirred overnight at room temperature. After solvent removal, the residue is precipitated from methanol and ethyl acetate to afford the desirable product (0.13 g) in 46% yield. $^1H$ NMR (400 MHz, DMSO-$d_6$) δ 9.27 (d, J=6.8 Hz, 1H), 9.18 (d, J=8.0 Hz, 1H), 8.90 (s, 1H), 8.62 (d, J=7.2 Hz, 1H), 8.60 (d, J=6.8 Hz, 1H), 8.52 (d, J=16 Hz, 1H), 8.42 (d, J=16 Hz, 1H), 8.32 (d, J=8.4 Hz, 1H), 8.26-8.23 (m, 2H), 8.15 (d, J=8.8 Hz, 1H), 8.06 (t, J=7.6 Hz, 1H), 7.79 (d, J=8.4 Hz, 1H), 7.71 (d, J=8.0 Hz, 1H), 7.53 (t, J=7.2 Hz, 1H), 7.32 (t, J=7.2 Hz, 1H), 5.89 (s, 2H), 4.64 (t, J=5.2 Hz, 2H), 3.84 (t, J=5.2 Hz, 2H), 3.49-3.46 (m, 2H), 3.32-3.29 (m, 2H), 3.11 (s, 3H). $^{13}C$ NMR (100 MHz, DMSO-$d_6$) δ 167.9, 154.4, 147.9, 146.3, 142.4, 141.0, 138.7, 135.4, 128.9, 127.6, 126.5, 126.1, 122.9, 122.2, 122.1, 120.4, 120.0, 119.0, 116.2, 115.1, 110.6, 110.5, 71.3, 69.8, 68.9, 58.1, 42.9. HRMS (MALDI-TOF) m/z Calcd for $C_{30}H_{29}N_2O_4$ 481.2122. Found 481.2156 $[M]^+$.

Other applicable derivatives of SLCOOH is represented by the formula SLCOOH-n, where n=2-20:

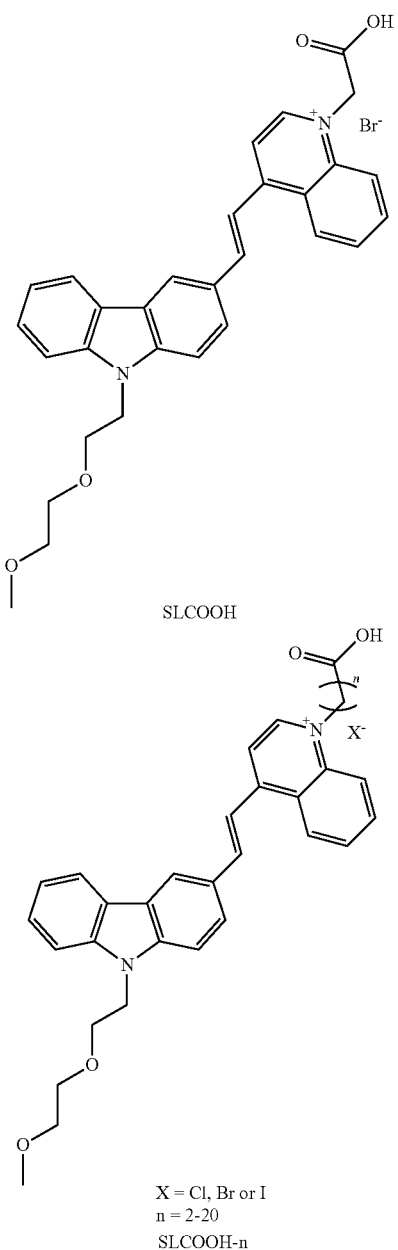

X = Cl, Br or I
n = 2-20
SLCOOH-n

The detailed synthesis scheme of SLCOOH-n is also shown in scheme 1B (FIG. 28)

Preparation of SLCOOH-Conjugated $SiO_2$@$Fe_3O_4$ Nanoparticles

According to Scheme 2A in FIG. 29, the $Fe_3O_4$@$SiO_2$@APTES nanoparticles (12 mg) (291) are added to a solution of SLCOOH (6 mg), EDC (22 mg) and sulfo-NHS (7 mg) in 0.1 M MES buffer (2.4 mL; pH=6.5). The mixture is sonicated at 40 W and 4° C. for 10 min and shaken at room temperature for 48 h. The SLCOOH-conjugated $SiO_2$@$Fe_3O_4$ nanoparticles (292) are magnetically separated and washed with a MES buffer.

Similarly, SLCOOH-n-conjugated $Fe_3O_4$@$SiO_2$@APTES nanoparticles (293) can also be synthesized according to Scheme 2B in FIG. 29 and based on the corresponding reagents and conditions applied in Scheme 2A, except that the solution of SLCOOH is replaced by SLCOOH-n solution.

FIG. 22 shows the absorption, emission and IR spectra of the magnetic nanoparticles (MNP) before and after the conjugation with SLCOOH. The absorption and emission properties of the SLCOOH-conjugated $SiO_2$@$Fe_3O_4$ nanoparticles are similar to those the SLCOOH. The fluorescence property of the cyanine compound allows near-infrared in-vivo fluorescence imaging. The IR spectra suggest the successful conjugation of SLCOOH onto the $SiO_2$@$Fe_3O_4$ nanoparticles.

FIG. 23A-23B shows TEM images of $SiO_2$@$Fe_3O_4$ and SLCOOH-conjugated $SiO_2$@$Fe_3O_4$ nanoparticles with Aβ fibrils. The $SiO_2$@$Fe_3O_4$ nanoparticles are round in shape with narrow size distribution. Upon mixing with the preformed Aβ fibrils, the nanoparticles readily attach to the fibrils, suggesting the high affinity of the SLCOOH-conjugated $SiO_2$@$Fe_3O_4$ nanoparticles towards Aβ fibrils.

FIG. 24 shows the cell viability values (%) assessed by MTT Assays. Human neuroblastoma SH-SY5Y neuronal cells were incubated with different concentrations of SLCOOH-conjugated $SiO_2$@$Fe_3O_4$ nanoparticles at 37° C. for 24 h. The nanoparticles are of no significant cytotoxicity (survival >80%) over the concentration within a range of 0-1 mg/mL.

FIG. 25A-25D shows in-vivo NIR fluorescence images of brain region of a 12-month-old APP/PS1 Aβ-over-expressing transgenic mouse before and after IV injection of 100 μL SLCOOH-conjugated $SiO_2$@$Fe_3O_4$ nanoparticles (10 mg/kg) at different time points (30, 60, 180 min). $\lambda_{ex}$=500 nm, $\lambda_{em}$=620-660 nm. This result supports that the SLCOOH-conjugated $SiO_2$@$Fe_3O_4$ nanoparticles are able to cross the blood-brain barrier and reach the brain. The uptake by the brain is fast and within 30 min. The clearance of the nanoparticles is also fast which is shorter than 180 min after the administration of the nanoparticles.

FIG. 26A-26D shows the fluorescence images of a brain slice of transgenic mice which was administrated with SLCOOH-conjugated $SiO_2$@$Fe_3O_4$ nanoparticles via tail vein injection and the brain slice was co-stained with Aβ-targeting Thioflavin T (ThT). (A) Differential Interference Contrast (DIC) image of the brain slice of a 12-month-old APP/PS1 Tg mouse. (B) Histological staining of the brain slice with SLCOOH-conjugated $SiO_2$@$Fe_3O_4$ nanoparticles ($\lambda_{ex}$=500 nm, $\lambda_{em}$=620-680 nm). (C) ThT fluorescence images of the brain slice captured with $\lambda_{ex}$=405 nm, $\lambda_{em}$=460-490 nm (D) The superimposed images of (B) and (C). The overlaid image evidence the selective Aβ-targeting capability of the SLCOOH-conjugated $SiO_2$@$Fe_3O_4$ nanoparticles.

FIG. 27A-27B shows in vivo $T_2$ MRI images of a live 3-month-old APP/PS1 transgenic mouse brain (a) before and (b) after a tail-vein injection of SLCOOH-conjugated $SiO_2$@$Fe_3O_4$ nanoparticles (100 μL, 10 mg/mL) at 2 hours. The dark spots (indicated by the white arrows) observed in the MRI image inside the transgenic mouse's brain after administration of SLCOOH-conjugated $SiO_2$@$Fe_3O_4$ nanoparticles indicate the presence of the SLCOOH-conjugated $SiO_2$@$Fe_3O_4$ nanoparticles. The presence of Aβ deposition is thus evidenced by the localization of the dark spots of the SLCOOH-conjugated $SiO_2$@$Fe_3O_4$ nanoparticles.

It is noteworthy that "SLCOOH-conjugated $SiO_2$@$Fe_3O_4$ nanoparticles" is only one of the examples of the modified carbazole-based fluorophore of the presently claimed invention for better illustration of the presently claimed invention but without the intention to limit the present method to the use of this particular nanoparticle. Other derivatives derived from the compound of formula S or V, e.g., SLCOOH-n, can also be used to conjugate with the magnetic nanoparticles according to the present invention to form a conjugate that exerts similar or even better efficiency, accuracy and/or specificity in imaging, detecting, and/or targeting aggregation of Aβ or the like in the subject being introduced therewith.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extent. All publications recited herein are hereby incorporated by reference in their entirety.

INDUSTRIAL APPLICABILITY

The presently claimed carbazole-based fluorophores which are conjugated with magnetic nanoparticles are useful in labeling, imaging and detecting the beta-amyloid (Aβ) peptides, oligomers, and fibrils in vitro and in vivo via magnetic resonance and florescence imaging. The presently claimed carbazole-based fluorophores conjugated with the magnetic nanoparticles are also useful in developing drugs or being applied in the treatment for reducing and preventing aggregation of beta-amyloid peptides for Alzheimer's disease (AD), thereby treating Alzheimer's disease and/or preventing the onset thereof. The presently claimed conjugate is also useful as a bimodal imaging contrast agent for MRI and fluorescent imaging of the presence and location of aggregation of Aβ peptides or the like.

What is claimed is:

1. A method for imaging and detection of beta-amyloid (Aβ) peptides aggregation via magnetic resonance imaging (MRI) based on modified carbazole-based fluorophores comprising a formula S series:

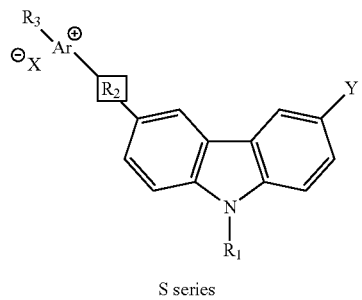

S series said method comprising:
conjugating said carbazole-based fluorophores to magnetic nanoparticles to form a conjugate of said carbazole-based fluorophores and said magnetic nanoparticles;
introducing said conjugate to a subject with beta-amyloid (Aβ) peptides aggregation; and applying magnetic resonance imaging (MRI) to image and detect said conjugate bound to the beta-amyloid (Aβ) peptides aggregation in said subject;

wherein Ar is a heteroaromatic ring selected from the group consisting of pyridinyl, substituted pyridinyl, quinolinyl, substituted quinolinyl, acridinyl, substituted acridinyl, benzothiazolyl, substituted benzothiazolyl, benzoxazolyl, and substituted benzoxazolyl;

$R_1$ is a radical selected from the group consisting of polyethylene glycol chain, alkyl, substituted alkyl, peptide chain, glycosidyl, and $C(O)NHCH((CH_2CH_2O)_2CH_3)_2$;

$R_2$ is selected from the group consisting of ethenyl, ethynyl, azo and azomethinyl.

$R_3$ is a radical selected from the group consisting of alkyl, HO-alkyl, HS-alkyl, $H_2$N-alkyl, HNalkyl-alkyl, alkyl-COOalkyl, alkyl-$CONH_2$, alkyl-CONHalkyl, alkyl-COOH, alkyl-COO$^-$, (alkyl)$_3$N$^+$-alkyl, and (Ph)$_3$P$^+$-alkyl and polyethylene glycol chain;

X is an anion selected from the group consisting of F, Cl, Br, I, $HSO_4$, $H_2PO_4$, $HCO_3$, tosylate, and mesylate;

Y is selected from the group consisting of H, F, Cl, OH, $OCH_3$, and $R_2$—Ar—$R_3$.

2. The method according to claim 1, wherein when Y is substituted by $R_2$—Ar—$R_3$, said carbazole-based fluorophores are represented by a formula V series:

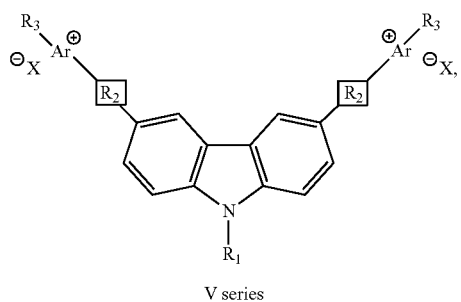

V series wherein Ar is a heteroaromatic ring selected from the group consisting of pyridinyl, substituted pyridinyl, quinolinyl, substituted quinolinyl, acridinyl, substituted acridinyl, benzothiazolyl, substituted benzothiazolyl, benzoxazolyl, and substituted benzoxazolyl; $R_2$ is selected from the group consisting of ethenyl, ethynyl, azo and azomethinyl; $R_3$ is a radical selected from the group consisting of alkyl, HO-alkyl, HS-alkyl, $H_2$N-alkyl, HNalkyl-alkyl, alkyl-COOalkyl, alkyl-$CONH_2$, alkyl-CONHalkyl, alkyl-COOH, alkyl-COO$^-$, (alkyl)$_3$N$^+$-alkyl, and (Ph)$_3$P$^+$-alkyl, and polyethylene glycol chain.

3. The method according to claim 1, wherein when Ar is substituted by quinolinyl, $R_1$ is substituted by polyethylene glycol chain, $R_2$ is substituted by ethenyl, $R_3$ is substituted by alkyl-COOH, X is substituted by Br, Cl or I, and Y is substituted by H, said carbazole-based fluorophores are represented by the formula SLCOOH and the derivatives therefore are represented by the formula SLCOOH-n:

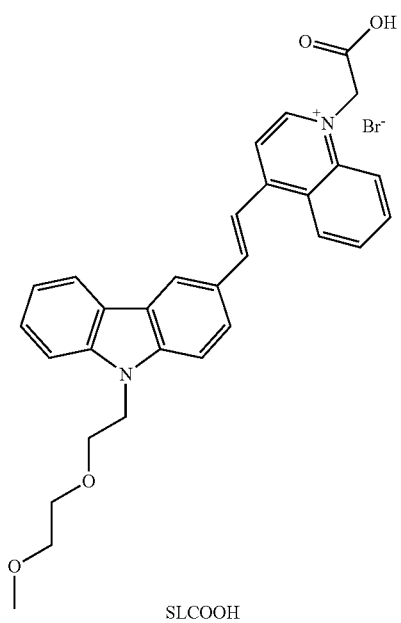

SLCOOH

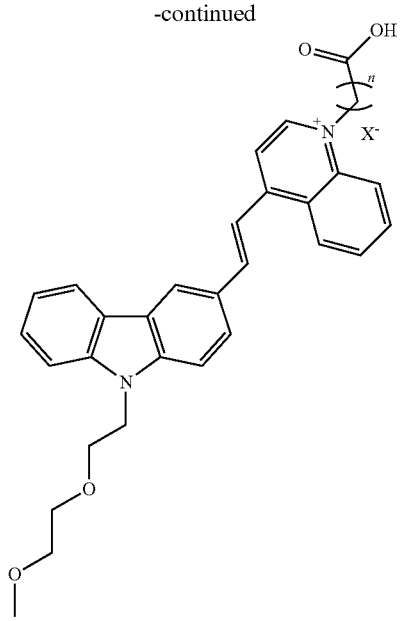

SLCOOH-n wherein n=2-20.

4. The method according to claim 1, wherein said conjugate is permeable to blood-brain barrier.

5. The method according to claim 1, wherein the magnetic nanoparticles are superparamagnetic and anti-ferromagnetic.

6. The method according to claim 3, wherein the magnetic nanoparticles comprising $SiO_2@Fe_3O_4$, and said conjugate is represented by one of the following formulae:

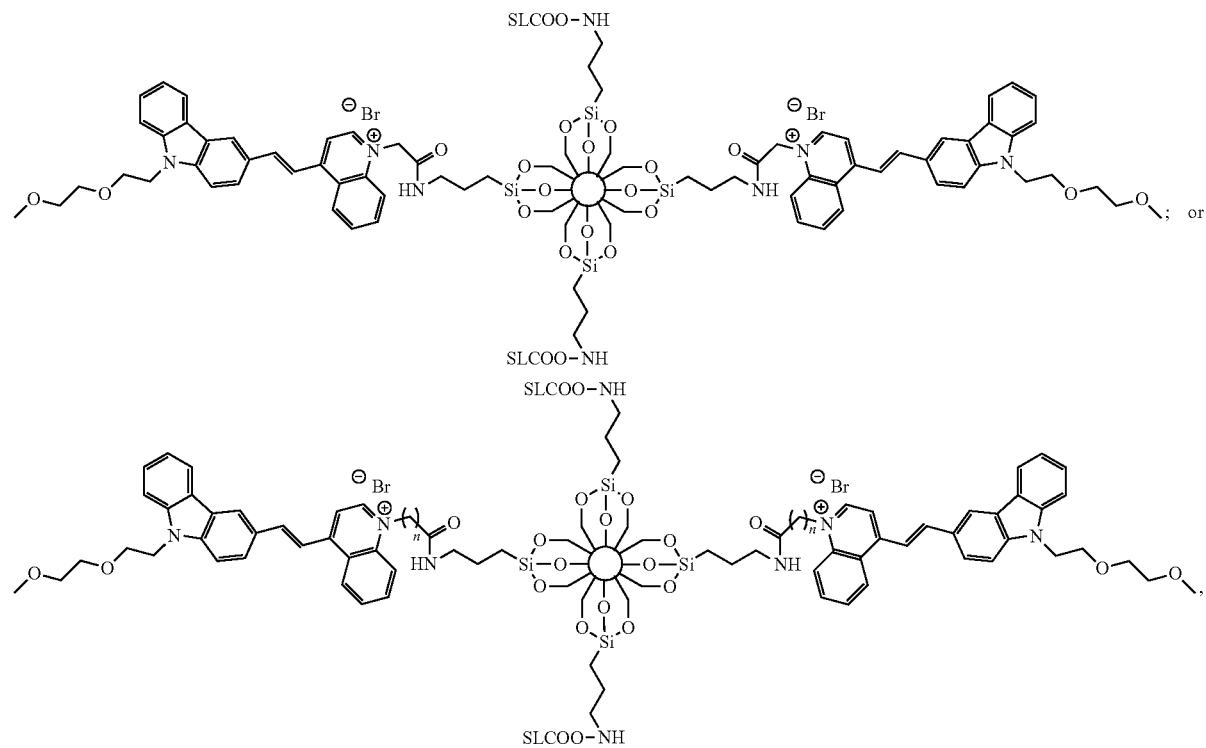

wherein

represents said SiO$_2$ @Fe$_3$O$_4$; X represents Br, I, or Cl.

7. The method according to claim 1, further comprising administering said conjugate to said subject in vivo.

8. The method according to claim 1 wherein said beta-amyloid (Aβ) peptides aggregation is associated with Alzheimer's disease.

9. The method according to claim 1 wherein said conjugate is introduced to said subject with beta-amyloid (Aβ) peptides aggregation via intravenous injection.

10. The method according to claim 1, wherein said conjugate is introduced at about 10 mg/kg to the body weight of said subject.

11. A method for imaging and detection of beta-amyloid (Aβ) peptides aggregation via fluorescence imaging based on modified carbazole-based fluorophores comprising a formula S series:

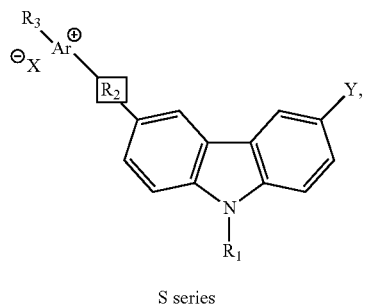

S series said method comprising:
conjugating said carbazole-based fluorophores to magnetic nanoparticles to form a conjugate of said carbazole-based fluorophores and said magnetic nanoparticles;
introducing said conjugate to a subject with beta-amyloid (Aβ) peptides aggregation; and
applying fluorescence imaging to image and detect said conjugate bound to the beta-amyloid (Aβ) peptides aggregation in said subject;
wherein Ar is a heteroaromatic ring selected from the group consisting of pyridinyl, substituted pyridinyl, quinolinyl, substituted quinolinyl, acridinyl, substituted acridinyl, benzothiazolyl, substituted benzothiazolyl, benzoxazolyl, and substituted benzoxazolyl;
R$_1$ is a radical selected from the group consisting of polyethylene glycol chain, alkyl, substituted alkyl, peptide chain, glycosidyl, and C(O)NHCH((CH$_2$CH$_2$O)$_2$CH$_3$)$_2$;
R$_2$ is selected from the group consisting of ethenyl, ethynyl, azo and azomethinyl.
R$_3$ is a radical selected from the group consisting of alkyl, HO-alkyl, HS-alkyl, H$_2$N-alkyl, HNalkyl-alkyl, alkyl-COOalkyl, alkyl-CONH$_2$, alkyl-CONHalkyl, alkyl-COOH, alkyl-COO$^-$, (alkyl)$_3$N$^+$-alkyl, and (Ph)$_3$P$^+$-alkyl and polyethylene glycol chain;
X is an anion selected from the group consisting of F, Cl, Br, I, HSO$_4$, H$_2$PO$_4$, HCO$_3$, tosylate, and mesylate;
Y is selected from the group consisting of H, F, Cl, OH, OCH$_3$, and R$_2$—Ar—R$_3$.

12. The method according to claim 11, wherein when Y is R$_2$—Ar—R$_3$, said carbazole-based fluorophores are represented by a formula V series:

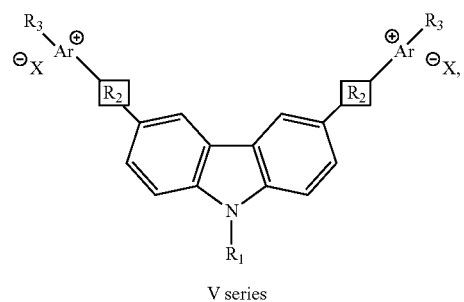

V series wherein Ar is a heteroaromatic ring selected from the group consisting of pyridinyl, substituted pyridinyl, quinolinyl, substituted quinolinyl, acridinyl, substituted acridinyl, benzothiazolyl, substituted benzothiazolyl, benzoxazolyl, and substituted benzoxazolyl; R$_2$ is selected from the group consisting of ethenyl, ethynyl, azo and azomethinyl; R$_3$ is a radical selected from the group consisting of alkyl, HO-alkyl, HS-alkyl, H$_2$N-alkyl, HNalkyl-alkyl, alkyl-COOalkyl, alkyl-CONH$_2$, alkyl-CONHalkyl, alkyl-COOH, alkyl-COO$^-$, (alkyl)$_3$N$^+$-alkyl, and (Ph)$_3$P$^+$-alkyl, and polyethylene glycol chain.

13. The method according to claim 11, wherein when Ar is substituted by quinolinyl, R$_1$ is substituted by polyethylene glycol chain, R$_2$ is substituted by ethenyl, R$_3$ is substituted by alkyl-COOH, X is substituted by Br, Cl or I, and Y is substituted by H, said carbazole-based fluorophores are represented by the formula SLCOOH and the derivatives thereof are represented by the formula SLCOOH-n:

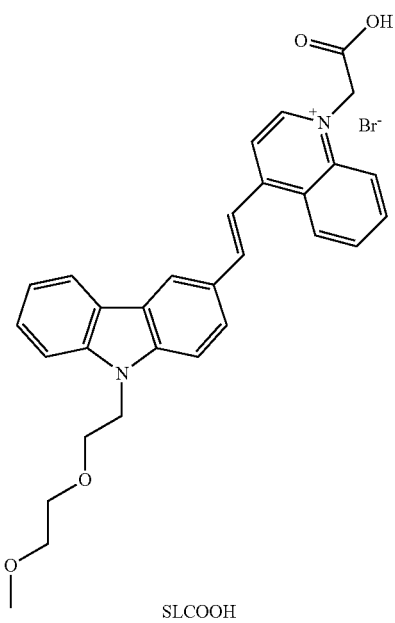

SLCOOH

-continued

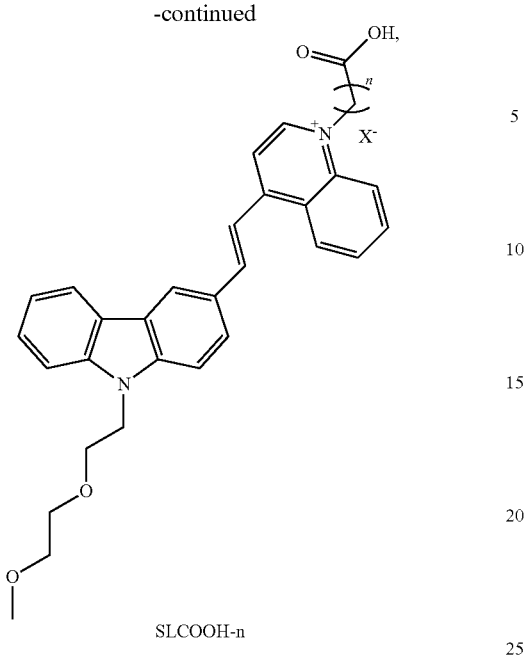

SLCOOH-n wherein n=2-20.

14. The method according to claim 11, wherein said conjugate is permeable to blood-brain barrier.

15. The method according to claim 11, wherein the magnetic nanoparticles are superparamagnetic and anti-ferromagnetic.

16. The method according to claim 13, wherein the magnetic nanoparticles comprising $SiO_2@Fe_3O_4$, and said conjugate is represented by one of the following formulae:

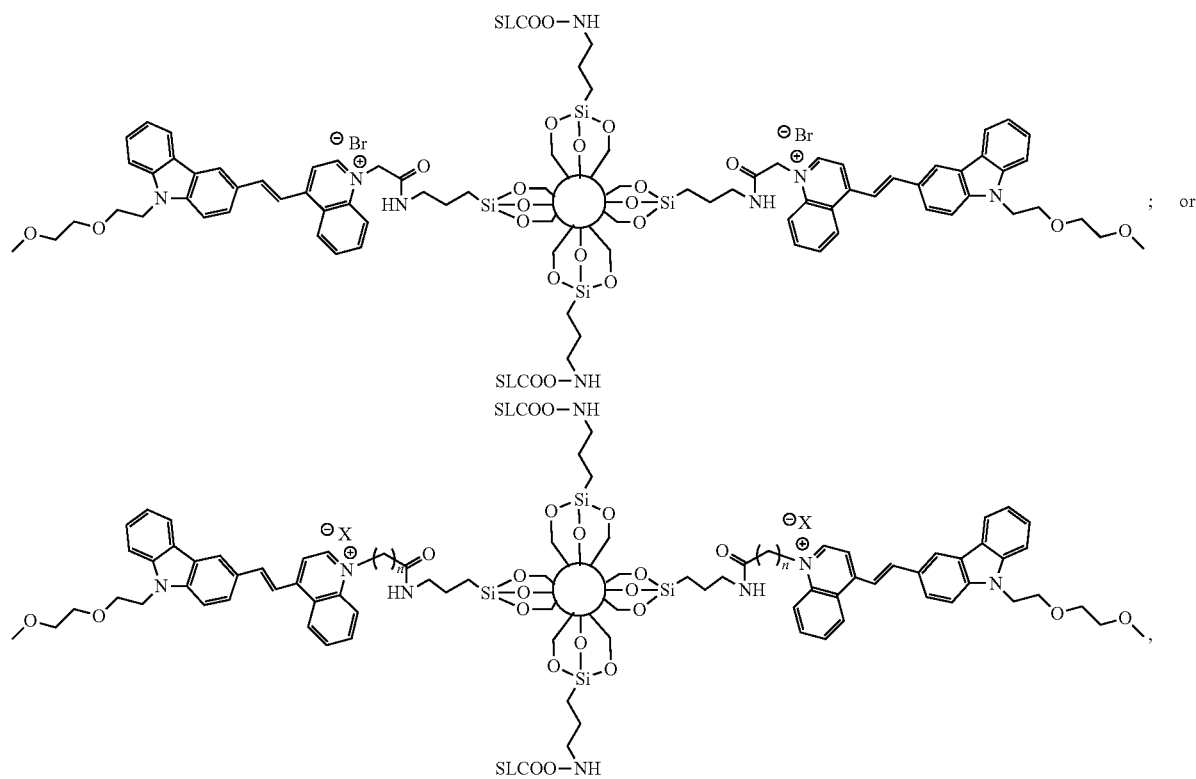

wherein

represents said $SiO_2@Fe_3O_4$; X represents Br, I, or Cl.

17. The method according to claim 11, further comprising introducing said conjugate to Aft peptides, oligomers and/or fibrils thereof in vitro.

18. The method according to claim 11, further comprising administering said conjugate to said subject in vivo.

19. The method according to claim 11 wherein said beta-amyloid (Aβ) peptides aggregation is associated with Alzheimer's disease.

20. The method according to claim 11 wherein said conjugate is introduced to said subject with beta-amyloid (Aβ) peptides aggregation via intravenous injection.

21. The method according to claim 11, wherein said conjugate is introduced at about 10 mg/kg to the body weight of said subject.

* * * * *